United States Patent [19]

Zhitetsky et al.

[11] 4,088,974

[45] May 9, 1978

[54] DIGITAL DEVICE FOR AUTOMATICALLY CHECKING CARBON CONTENT IN METAL WITH REFERENCE TO TEMPERATURE STOPS ON COOLING CURVE

[76] Inventors: Leonid Sergeevich Zhitetsky, ulitsa Vernadskogo, 61, kv. 8/4; Leonid Solomonovich Fainzilberg, prospekt 40-letia Oktyabrya, 142/144, both of Kiev, U.S.S.R.

[21] Appl. No.: 614,532

[22] Filed: Sep. 18, 1975

[30] Foreign Application Priority Data

Jan. 21, 1975  U.S.S.R. .................................. 210027

[51] Int. Cl.$^2$ ...................... G06F 15/20; G01N 25/02
[52] U.S. Cl. .................................. 364/472; 73/17 R; 75/130 R; 364/499; 364/557
[58] Field of Search .................. 235/151.3, 151.35; 73/17 R, 341, 359, 360, 361; 75/129, 130, 132

[56] References Cited

U.S. PATENT DOCUMENTS

| | | | |
|---|---|---|---|
| 3,375,106 | 3/1968 | McKissick et al. | 75/130 R |
| 3,670,558 | 6/1972 | Ryntz, Jr. et al. | 73/17 R |
| 3,766,772 | 10/1973 | Kern et al. | 73/17 R |
| 3,824,837 | 7/1974 | Nagaoka et al. | 73/17 R |
| 3,891,834 | 6/1975 | Warsinski | 235/151.3 |

*Primary Examiner*—Joseph F. Ruggiero
*Attorney, Agent, or Firm*—Lackenbach, Lilling & Siegel

[57] ABSTRACT

According to the invention, the proposed digital device for automatically checking the carbon content in a metal with reference to the temperature stops on the cooling curves comprises a converter which converts the actual temperature of the metal into a numerical pulse code, said converter having applied to its input a signal carrying information on the metal's temperature, said converter having outputs consisting of code pulses corresponding to positive and negative temperature increments on the cooling curve; a reversible counter which converts the numerical pulse code into a parallel code, said reversible counter having its add and subtract inputs electrically coupled to the outputs of the converter; a clock pulse generator; a time interval discriminator whose code pulse inputs are electrically connected to the outputs of the converter, said discriminator's clock pulse input being electrically connected to the output of the clock pulse generator; a code storage register to store the codes corresponding to the temperature stops on the cooling curve, said register's information inputs being connected to digit outputs of the reversible counter, said register's control input being electrically coupled to an output of the time interval discriminator, a pulse being applied to said register at the moment when a temperature stop on the cooling curve is detected; and a digital display unit whose information inputs are electrically connected to digit outputs of the register.

The device according to the present invention eliminates subjective errors which are bound to occur in any visual readout of data and makes it possible to fully automate the checking of the carbon content in a metal with reference to the crystallization temperature.

63 Claims, 38 Drawing Figures

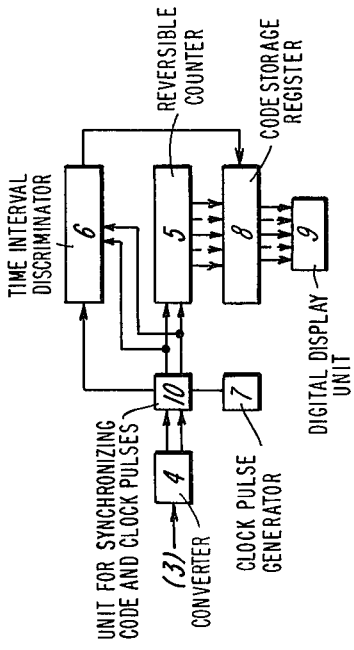
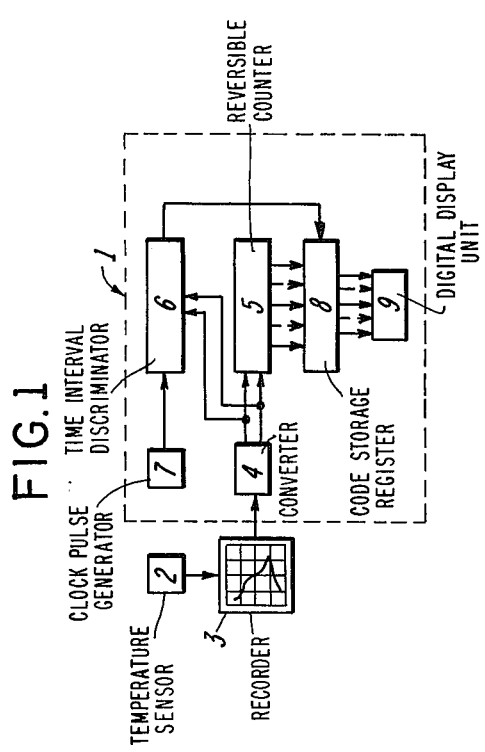
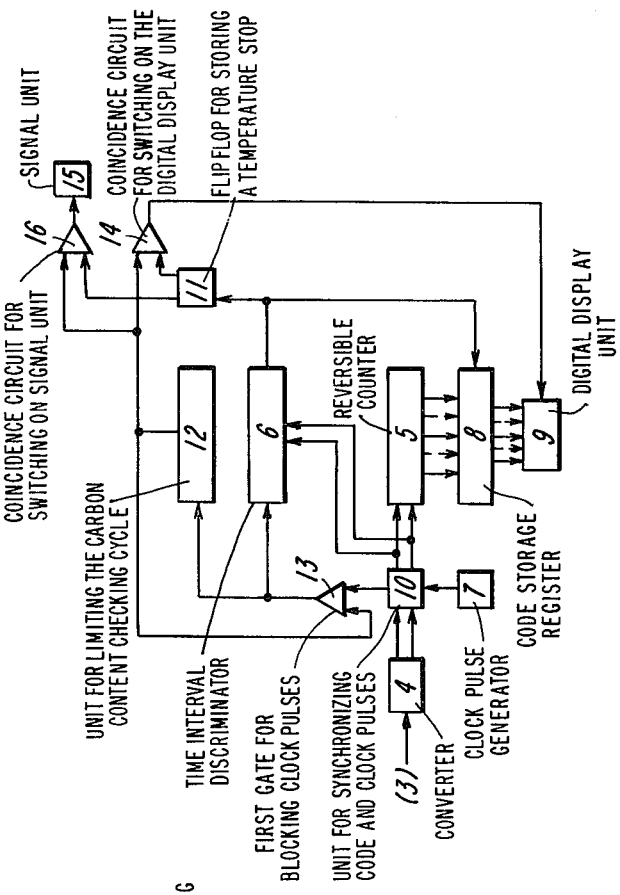
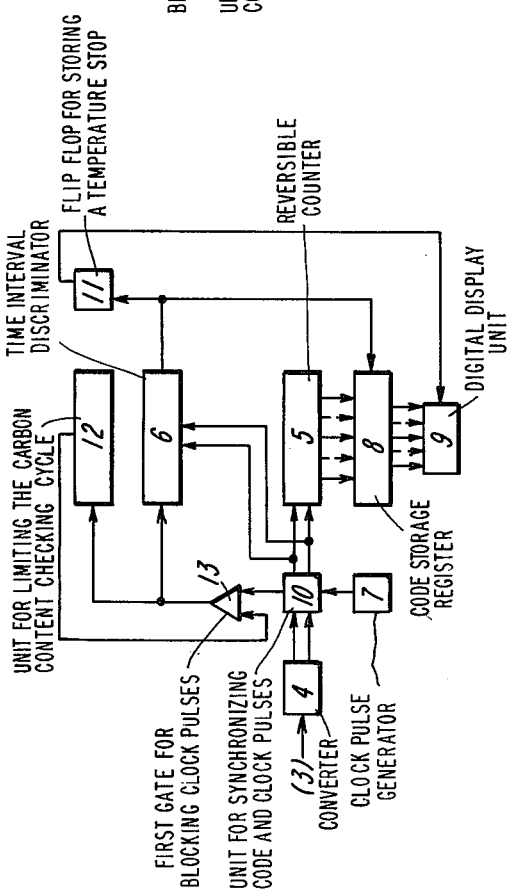

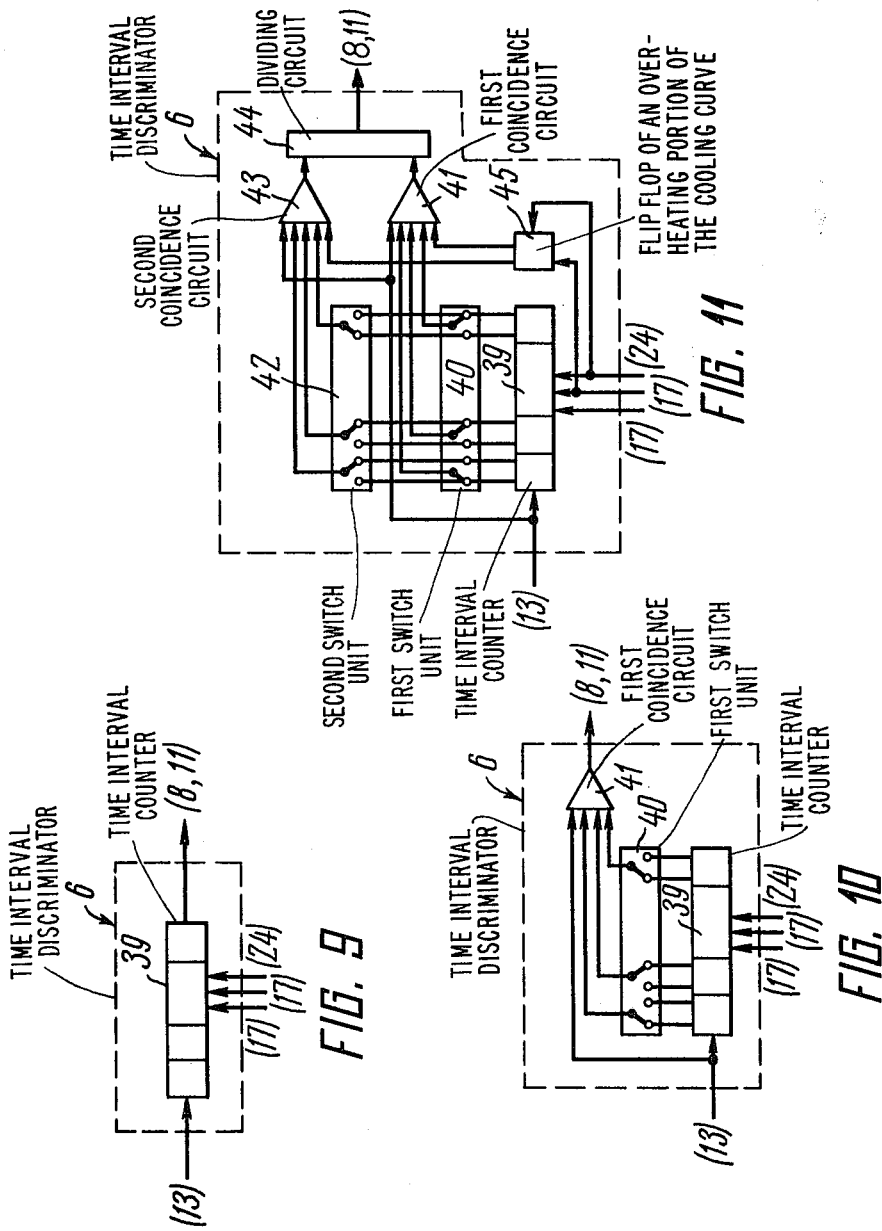

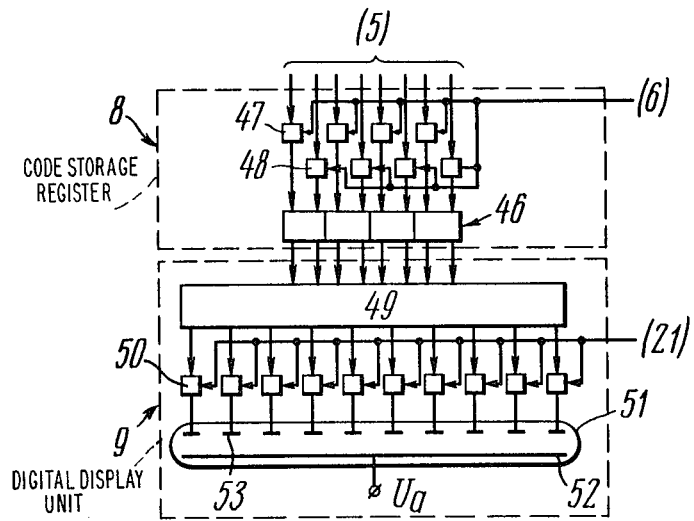
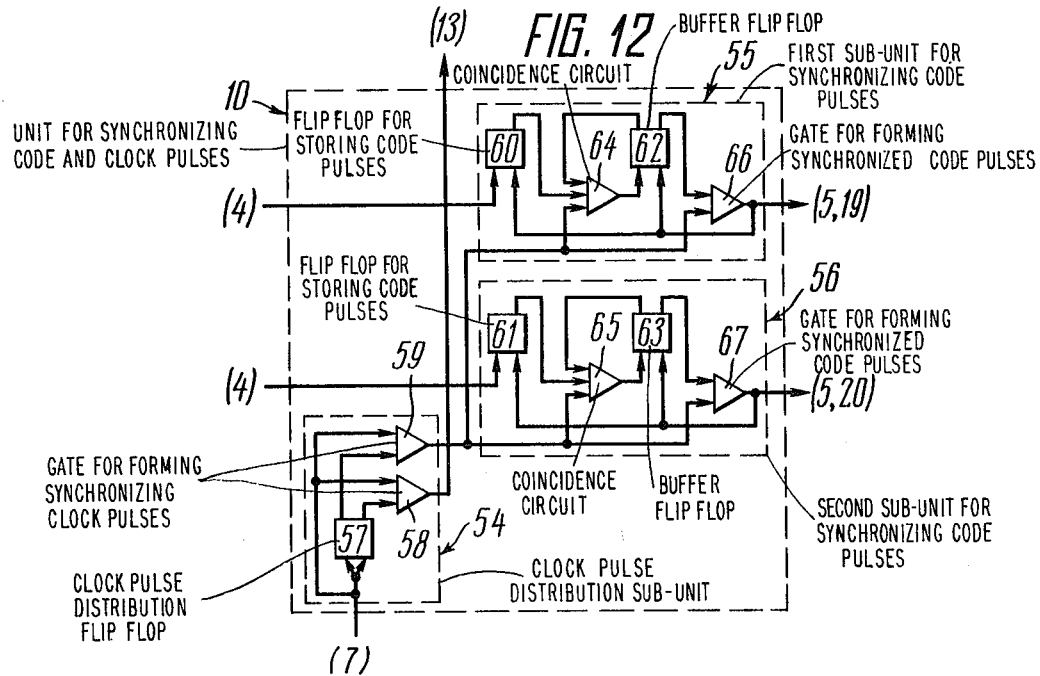

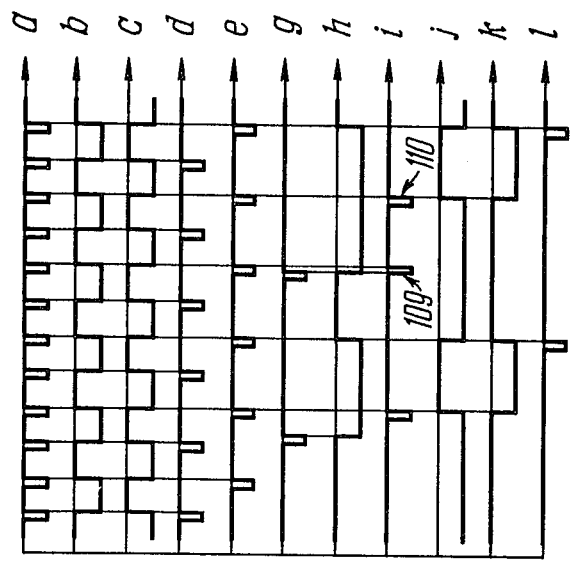
FIG. 26
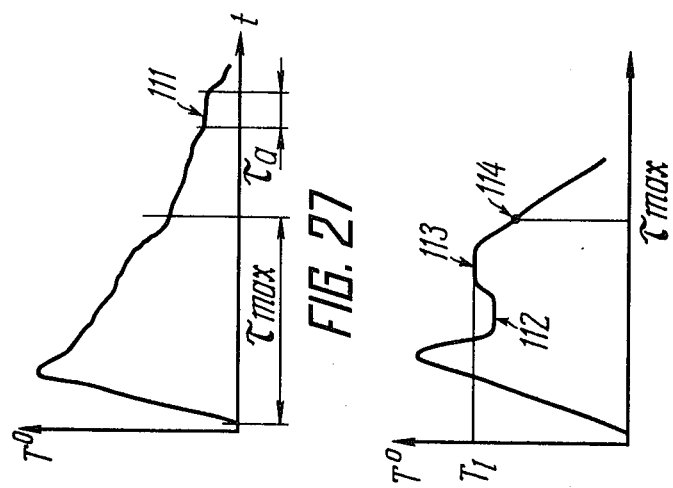
FIG. 27
FIG. 28

DIGITAL DEVICE FOR AUTOMATICALLY CHECKING CARBON CONTENT IN METAL WITH REFERENCE TO TEMPERATURE STOPS ON COOLING CURVE

The present invention relates to digital measuring devices for checking the parameters of molten metal and, more particularly, to digital devices for checking the carbon content in a metal with reference to the temperature stops on a cooling curve. The invention is applicable to automatic systems for checking and controlling steel smelting processes.

There are widely known measuring devices for checking the concentration of carbon in a molten metal, for example, steel, with reference to the beginning crystallization temperature the sample of molten metal. Such devices ensure a sufficiently high accuracy of carbon content checking (±0.02 percent of C) with a duration of the checking operation of about 30 sec.

A device of this type comprises a refractory sampler where there is installed a temperature sensor, for example, a thermocouple. The device also includes a recorder (an automatic potentiometer) for plotting the cooling curve of a sample of metal.

The crystallization temperature is determined by an operator by visually following the cooling curve and detecting a characteristic temperature stop thereon. The result of the measurements depends, therefore, on the operator's experience; it should be noted that this type of measurement is liable to subjective errors on the part of the operator.

Cooling curves are extremely diverse, so in many cases it is difficult for the operator to make a correct decision. The obligatory participation of the operator in the measuring process makes it impossible to directly enter the information on the carbon concentration into the computer that controls the steel smelting process.

The need for objective information on carbon concentration in a metal necessitates the automation of the processing of cooling curves within a measuring cycle.

It is, therefore, an object of the present invention to provide a digital device which would ensure automatic checking of the carbon content in a metal with reference to the temperature stops on the cooling curves.

The invention essentially aims at providing a device that would automatically detect temperature stops on a cooling curve in the course of measurements, determine the crystallization temperature and the respective carbon concentration and then express them in a digital form.

The foregoing objects of the present invention are attained in a device for automatically checking the carbon content in a metal with reference to the temperature stops on a cooling curve, said device comprising a converter which converts the actual temperature of the metal into a numerical pulse code, said converter having applied to its input a signal carrying information on the temperature of the metal, said converter having an output of code pulses corresponding to a positive increment of temperature on the cooling curve and an output of code pulses corresponding to a negative increment of temperature on the cooling curve; a reversible counter for converting the numerical pulse code into a parallel code, said reversible counter's add and subtract inputs are electrically connected to the outputs of the converter; a clock pulse generator; and a time interval discriminator whose code pulse inputs are electrically connected to the outputs of the converter and its clock pulse input is electrically connected to an output of the clock pulse generator; a code storage register for storing codes corresponding to the temperature stops on the cooling curve, said register's information inputs are connected to digit outputs of the reversible counter, said register's control input being electrically connected to the output of the time interval discriminator a pulse being applied to said register at the moment of detecting a temperature stop on the cooling curve; and a digital display unit whose information inputs are electrically connected to the digit outputs of the register.

In order to raise the reliability of the device, it is expedient that the device should include, according to the invention, a unit for synchronizing code and clock pulses, whose two code pulse inputs are connected to respective outputs of the converter, whereas its third input is connected to the clock pulse generator, the output of synchronized clock pulses of the unit for synchronizing code and clock pulses being electrically connected to the clock pulse input of the time interval discriminator, whereas the outputs of synchronized code pulses corresponding to positive and negative increments of temperature on the cooling curve are connected to the add and subtract inputs of the reversible counter and are electrically connected to respective code pulse inputs of the time interval discriminator.

It is expedient, in accordance with the invention, that the device should further include a flip-flop of a temperature stop on the cooling curve, whose input is connected to the output of the time interval discriminator, its output being electrically connected to the control input of the digital display unit.

It is expedient, in accordance with the invention, that the device should include a gate for blocking the passage of clock pulses, its pulse input being electrically connected to the output of the generator, whereas its output is connected to the clock pulse input of the time interval discriminator, as well as a unit for limiting the carbon content checking cycle, whose input is connected to the output of the gate for blocking the passage of clock pulses, and whose output, to which there is applied a signal as to the end of the carbon content checking cycle, is connected to the control input of the gate for blocking the passage of clock pulses.

It is advisable, in accordance with the invention, that the gate for blocking the passage of clock pulses should be electrically coupled to the generator via a synchronization unit.

According to the invention, the proposed device may also include a coincidence circuit for switching on the digital display unit, the inputs of said coincidence circuit being connected to one of the outputs of the flip-flop of a temperature stop on the cooling curve and to the output of the unit for limiting the carbon content checking cycle, the output of said coincidence circuit being electrically connected to the control input of the digital display unit.

It is highly desirable, according to the invention, that the device should further include a signal unit to give a signal to repeat the carbon content checking cycle. There should also be provided a coincidence circuit for switching on the signal unit. The inputs of said coincidence circuit being connected to another output of the flip-flop of a temperature stop on the cooling curve and to the output of the unit for limiting the carbon content checking cycle, the output of said concidence circuit being connected to the input of the signal unit.

It is expedient, in accordance with the invention, that the device should include a discriminator of local increments of temperature on the cooling curve, whose inputs are electrically connected to respective outputs of the converter, whereto code pulses are applied, and whose pulse outputs, whereto there are applied signals in cases of certain positive and negative temperature increments on the cooling curve, are connected to respective code pulse inputs of the time interval discriminator.

According to the invention, the discriminator of local temperature increments on the cooling curve may be electrically coupled to the converter via a synchronization unit.

It is expedient, in accordance with the invention, that the device should include two gates for blocking the passage of code pulses, whose pulse inputs are electrically connected to the outputs of the converter, and whose outputs are connected to respective inputs of the discriminator of local temperature increments on the cooling curve, as well as a coincidence circuit to form a signal as to the detection of the crystallization temperature, inputs of said coincidence circuit being connected to one of the outputs of the flip-flop of a temperature stop on the cooling curve and to an additional information output of the discriminator of local temperature increments on the cooling curve, whereto there is applied a signal in case of a certain negative increment of temperature on the cooling curve, the output of said coincidence circuit being connected to control inputs of the two gates for blocking the passage of code pulses and to the additional control input of the gate for blocking the passage of clock pulses.

According to the invention, the output of the coincidence circuit for forming a signal as to the detection of the crystallization temperature may also be electrically connected to the control input of the digital display unit.

In accordance with the invention, the gates for blocking the passage of code pulses may be coupled to the converter via a synchronization unit.

It is advisable, according to the invention, that the device should include a dividing circuit whose inputs are connected to the outputs of the coincidence circuit for switching on the digital display unit and the coincidence circuit for forming a signal as to the detection of the liquidus temperature, the output of said coincidence circuit being connected to the control input of the digital display unit.

It is highly advisable, in accordance with the invention, that the device should further include a functional code converter for the conversion of a code corresponding to a temperature stop on the cooling curve into a carbon concentration code, the inputs of said functional code converter being connected to information outputs of the register, its outputs being connected to the information inputs of the digital display unit.

It is expedient, in accordance with the invention, that the device should also include a coincidence circuit for selecting an initial setting code, the input of said coincidence circuit being connected to the outputs of the reversible counter, and a gate for forming an initial setting pulse, whose control input is connected to the output of the coincidence circuit for selecting an initial setting code, its pulse input being connected to the output of the converter of the actual temperature of metal into a numerical pulse code, whereto there are applied code pulses corresponding to a positive increment of temperature on the cooling curve, its output being connected to the initial setting inputs of the time interval discriminator, the unit for limiting the carbon content checking cycle, the discriminator of local temperature increments on the cooling curve, and the flip-flop of a temperature stop on the cooling curve.

According to the invention, the time interval discriminator may be constructed in the form of a time interval counter whose counting input serves as the clock pulse input of the time interval discriminator, its two initial setting inputs being code pulse inputs of the time interval discriminator corresponding to positive and negative temperature increments on the cooling curve, its third initial setting input being the initial setting input of the time interval discriminator.

It is advisable, in accordance with the invention, that the overflow output of the time interval counter should be the output of the time interval discriminator, whereto there is applied a pulse at a moment of detecting a temperature stop on the cooling curve.

According to the invention, the time interval discriminator may also include a switch unit and a coincidence circuit whose potential inputs are connected via the switch unit to the digit outputs of the time interval counter, the pulse input of the coincidence circuit being connected to the count input of the time interval counter, whereas the output of the coincidence circuit serves as the output of the time interval discriminator, whereto there are applied pulses following the detection of temperature stops on the cooling curve.

According to the invention, the time interval discriminator may additionally have a second switch unit and a second coincidence circuit whose potential inputs are connected via the second switch unit to the digit outputs of the time interval counter, as well as a flip-flop of an overheating portion of the cooling curve, whose output is connected to the control input of the first coincidence circuit, and whose other output is connected to the control input of the second coincidence circuit, and a dividing circuit whose inputs are connected to the outputs of the two coincidence circuits, the pulse input of the second coincidence circuit being combined with the pulse input of the first coincidence circuit, the input of the flip-flop of an overheating portion of the cooling curve being combined with the initial setting input of the time interval counter, whereto there are applied code pulses corresponding to a negative increment of temperature on the cooling curve, the initial setting input of the flip-flop of an overheating portion of the cooling curve being combined with the third initial setting input of the time interval counter, whereas the output of the dividing circuit is the output of the time interval discriminator, whereto there is applied a pulse at a moment of detecting a temperature stop on the cooling curve.

It is expedient, in accordance with the invention, that the unit for synchronizing code and clock pulses should include a clock pulse distribution sub-unit comprising a flip-flop for distributing clock pulses, a gate for forming synchronized clock pulses, and a gate for forming sychronizing clock pulses, their control inputs being connected to the outputs of said flip-flop, and their pulse inputs being interconnected and connected to the counting input of the flip-flop for distributing clock pulses and making up an input of the synchronization unit, whereto there are applied clock pulses, the output of the gate for forming synchronized clock pulses forming a respective input of the synchronization unit, as well as two sub-units for synchronizing code pulses, each comprising a flip-flop for storing code pulses, a buffer flip-flop, a gate for forming synchronized code pulses, whose control input is connected to one of the outputs of the buffer flip-flop, and a coincidence circuit whose inputs are connected to another output of the buffer flip-flop and to the output of the flip-flop for storing code pulses, the output of the gate for forming synchronizing clock pulses of the clock pulse distribution sub-unit being connected to the inputs of the coincidence circuits and gates for forming synchronized code pulses of the sub-units for synchronizing code pulses, the inputs of the flip-flops for storing code pulses of the sub-unit for synchronizing code pulses forming respective inputs of the synchronization unit, whereto there are applied code pulses corresponding to positive and negative increments of temperature on the cooling curve, the outputs of the gates for forming synchronized code pulses of each code pulse synchronization sub-unit being connected to other inputs of the flip-flops for storing code pulses and other inputs of the buffer flips-flops and serving as respective outputs of synchronized code pulses of the synchronization unit.

It is highly advisable, according to the invention, that the unit for limiting the carbon content checking cycle should be constructed as a time counter for counting the duration of a carbon content checking cycle, whose counting input is the input of the unit for limiting the carbon content checking cycle, its initial setting input being the initial setting input of the unit for limiting the carbon content checking cycle.

It is desirable, in accordance with the invention, that the top digit output of the carbon content checking cycle time counter should be the output of the unit for limiting the carbon content checking cycle, whereto there is applied a signal as to the end of the carbon content checking cycle.

The unit for limiting the carbon content checking cycle may additionally have, in accordance with the invention, a switch unit and a coincidence circuit whose outputs are connected via the switch unit to the digit outputs of the counter of the duration of the carbon content checking cycle, the output of the coincidence circuit being the output of the unit for limiting the carbon content checking cycle, whereto there is applied a signal as to the end of the carbon content checking cycle.

It is expedient, in accordance with the invention, that the discriminator of local temperature increments on the cooling curve should be constructed as a reversible counter for determining local temperature increments on the cooling curve, whose add and subtract inputs are the respective inputs of the discriminator of local temperature increments on the cooling curve, whereto there are applied pulses corresponding to positive and negative increments of temperature on the cooling curve, its initial setting input being the initial setting input of the discriminator of local temperature increments on the cooling curve, whereas its overflow outputs are pulse outputs of the discriminator of local temperature increments on the cooling curve, whereto there are applied signals in cases of a certain positive increment and a certain negative increment of temperature on the cooling curve.

It is expedient, in accordance with the invention, that the discriminator of local temperature increments on the cooling curve should include a reversible counter for determining local temperature increments on the cooling curve having a sign digit to whose add and subtract inputs there are connected two gates for blocking the count of code pulses corresponding to positive and negative increments of temperature on the cooling curve, as well as two switch units and two coincidence circuits at whose outputs there are formed signals in case of a certain positive increment and a certain negative increment of temperature on the cooling curve, the inputs of one of said coincidence circuits being connected to one sign digit output of the reversible counter for determining local temperature increments on the cooling curve and, via the switch unit, to the other digit outputs of the reversible counter for determining local temperature increments on the cooling curve, the inputs of the second coincidence circuit being connected to the other sign digit input of the reversible counter for determining local temperature increments on the cooling curve and, via the second switch unit, to the other digit outputs of the reversible counter for determining local temperature increments on the cooling curve, there also being in said discriminator two output gates, the control inputs of the gate for blocking the count of code pulses corresponding to a positive increment of temperature on the cooling curve and those of one output gate being connected to the output of the coincidence circuit, whereat there is formed a signal in case of a certain positive increment of temperature on the cooling curve, the control inputs of the gate for blocking the count of code pulses corresponding to a negative increment of temperature on the cooling curve and the other output gate being connected to the output of the coincidence circuit, whereat there is formed a signal in case of a certain negative increment of temperature on the cooling curve, the pulse inputs of the output gates of the discriminator of local temperature increments on the cooling curve, whereto there are applied signals in case of a certain positive increment and a certain negative increment of temperature on the cooling curve, and the pulse inputs of the gates for blocking the count of code pulses corresponding to positive and negative increments of temperature on the cooling curve being interconnected and serving as the inputs of the discriminator of local temperature increments on the cooling curve, whereto there arrive code pulses corresponding to positive and negative increments of temperature on the cooling curve, the outputs of the output gates of the discriminator of local temperature increments on the cooling curve, whereto there are applied signals in cases of a certain positive increment and a certain negative increment of temperature on the cooling curve, being connected to the two initial setting inputs of the reversible counter for determining local temperature increments on the cooling curve and serving as the respective pulse outputs of the discriminator of local temperature increments on the cooling curve, the output of the coincidence circuit, whereat there is formed a signal in case of a certain negative increment of temperature on the cooling curve, serving as the information output of the discriminator of local temperature increments on the cooling curve, the third initial setting input of the reversible counter for determining local temperature increments on the cooling curve serving as the initial setting input of the discriminator of local temperature increments on the cooling curve.

It is advisable, in accordance with the invention, that the discriminator of local temperature increments on the cooling curve should have two threshold units, each comprising a reversible counter for determining local temperature increments on the cooling curve, a switch unit, a coincidence circuit whose inputs are connected via the switch unit to the digit outputs of the reversible counter for determining local temperature increments on the cooling curve, a zero decoder whose inputs are connected to the digit outputs of the reversible counter for determining local temperature increments on the cooling curve, and two gates for blocking the count of code pulses corresponding to positive and negative increments of temperature on the cooling curve, whose outputs are connected to the add and subtract inputs of the reversible counter for determining local temperature increments on the cooling curve, as well as an output gate. In one of the threshold units, the output of the coincidence circuit, whereat there are formed signals in case of a certain positive increment of temperature on the cooling curve, is connected to the control inputs of the output gate and the gate for blocking the count of code pulses corresponding to a positive increment of temperature on the cooling curve, the output of the zero decoder being connected to the control input of the gate for blocking the count of code pulses corresponding to a negative increment of temperature on the cooling curve, the pulse inputs of the gate for blocking the count of code pulses corresponding to a positive increment of temperature on the cooling curve and the output gate being combined with the pulse input of the gate for blocking the count of code pulses corresponding to a positive increment of temperature of the other threshold unit and serving as the respective input of the discriminator of local temperature increments on the cooling curve, the output of the output gate being connected to the initial setting input of the reversible counter for determining local temperature increments on the cooling curve and serving as the pulse output of the discriminator of local temperature increments on the cooling curve, whereto there is applied a signal in case of a certain positive increment of temperature on the cooling curve, whereas in the other threshold unit, the output of the coincidence circuit, whereat there is formed a signal in case of a certain negative increment of temperature on the cooling curve, is connected to the control input of the output gate and the gate for blocking the count of code pulses corresponding to a negative increment of temperature on the cooling curve and serving as the information output of the discriminator of local temperature increments on the cooling curve, the output of the zero decoder being connected to the control input of the gate for blocking the count of code pulses corresponding to a positive increment of temperature on the cooling curve, the pulse inputs of the gate for blocking the count of code pulses corresponding to a negative increment of temperature on the cooling curve and the output gate being combined with the pulse input of the gate for blocking the count of code pulses corresponding to a negative increment of temperature on the cooling curve of the first threshold unit and serving as the respective input of the discriminator of local temperature increments on the cooling curve, the output of the output gate being connected to the initial setting input of the reversible counter for determining local temperature increments on the cooling curve and serving as the pulse output of the discriminator of local temperature increments on the cooling curve, whereto there is applied a signal in case of a certain negative increment of temperature on the cooling curve, the second initial setting inputs of the reversible counters for determining local increments of temperature on the cooling curve of the two threshold units being combined and serving as the initial setting input of the discriminator of local temperature increments on the cooling curve.

Other objects and advantages of the present invention will become more apparent from the following detailed description of examples of a preferred embodiment thereof to be read in conjunction with the accompanying drawings, wherein:

FIG. 1 is a block diagram of the proposed device connected to a conventional measuring device;

FIG. 2 is a block diagram of an alternative embodiment of the proposed device, wherein code and clock pulses are synchronized;

FIG. 3 is a block diagram of an alternative embodiment of the proposed device, wherein the results of checking are transmitted at the moment of detecting a temperature stop on the cooling curve, and wherein the carbon content checking cycle is limited;

FIG. 4 is a block diagram of an alternative embodiment of the proposed device, wherein information on the results of checking is transmitted upon the end of the carbon content checking cycle;

FIG. 9 is a functional diagram of a time interval discriminator;

FIG. 10 is a functional diagram of an adjustable time interval discriminator;

FIG. 11 is a functional diagram of a time interval discriminator which may be automatically readjusted, depending upon the type of cooling curve;

FIG. 12 is a functional diagram of a register connected to a digital display unit;

FIG. 13 is a functional diagram of a unit for synchronizing code and clock pulses;

Figure 17:
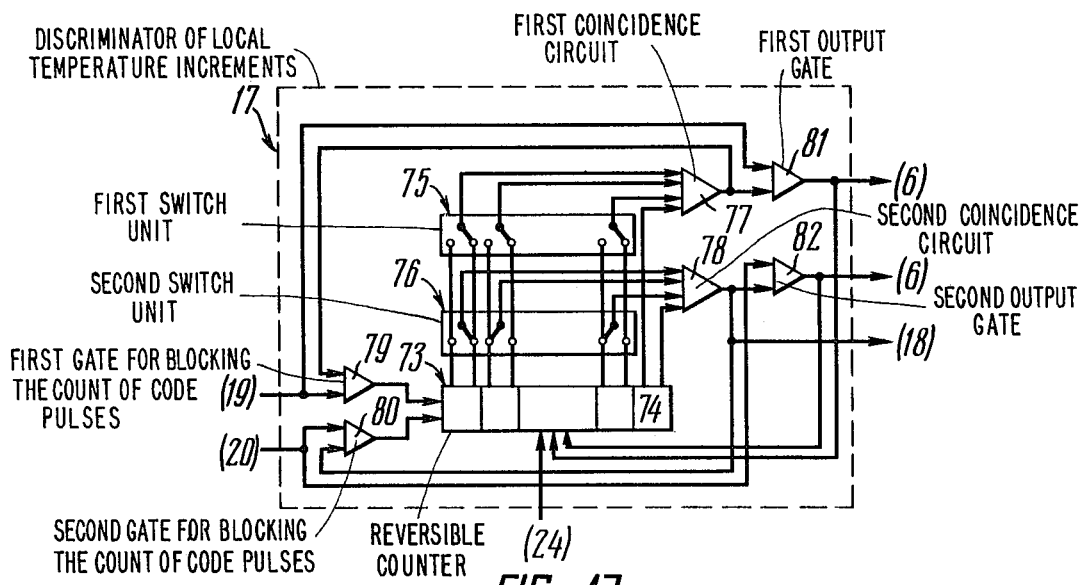
FIG. 17 shows the discriminator shown in FIG. 16 with means for adjusting the threshold of non-sensitivity to local temperature increments.
Figure 18:
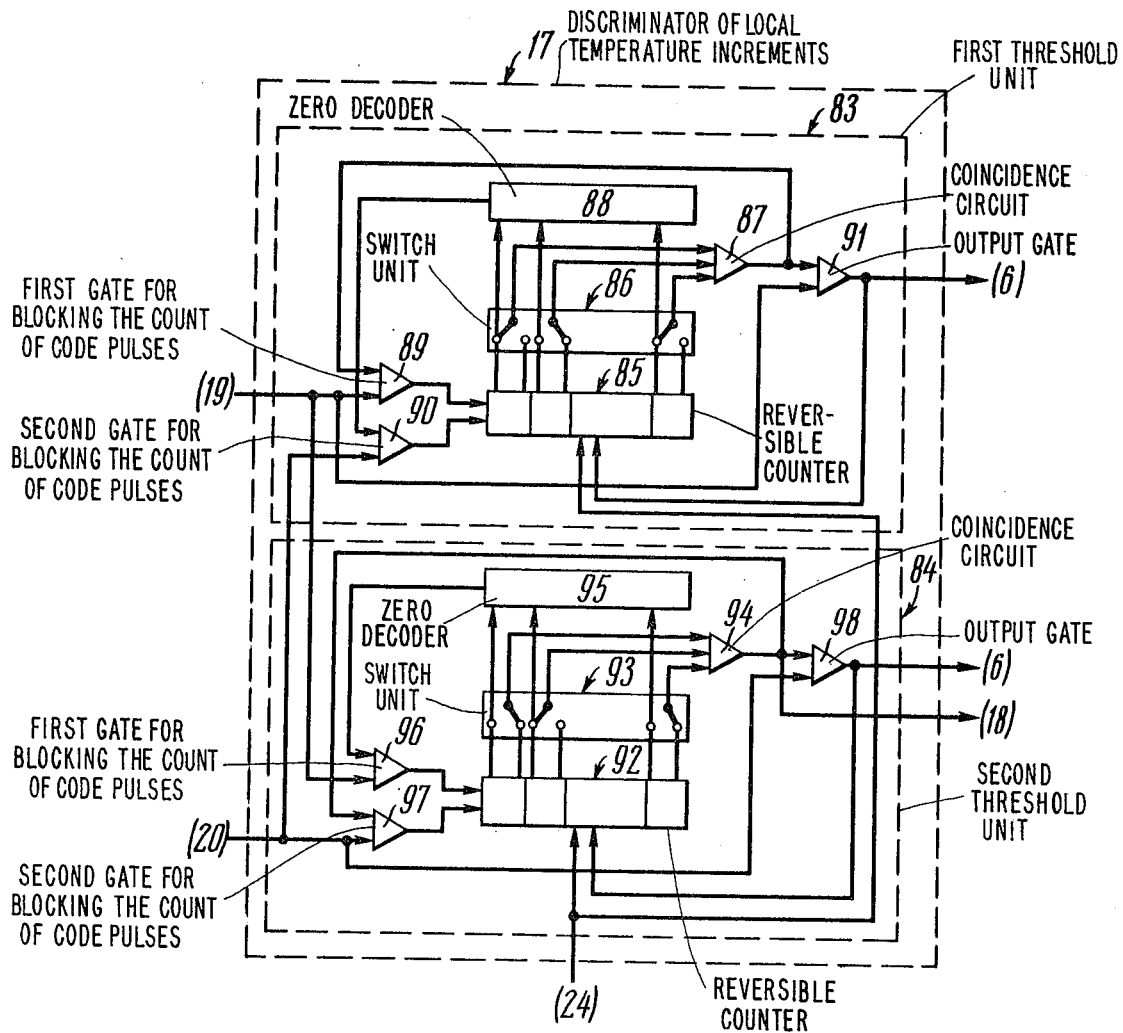
FIG. 18 shows the discriminator shown in FIGS. 16 and 17 with means for registering local temperature increments with reference to local extremums on the cooling curve.
Figure 32:
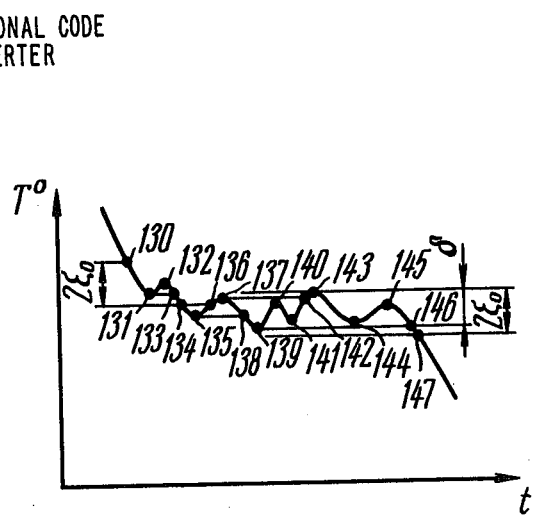
Figure 22:
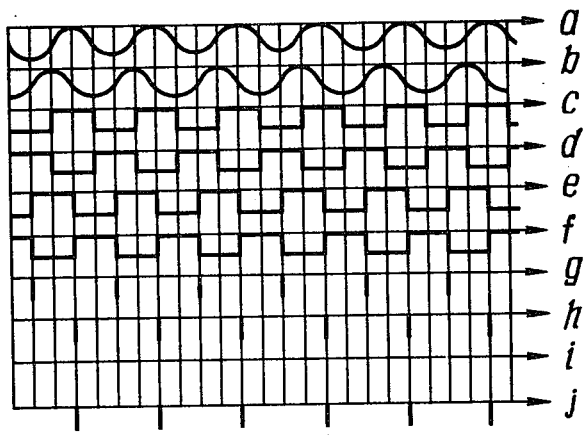
Figure 23:
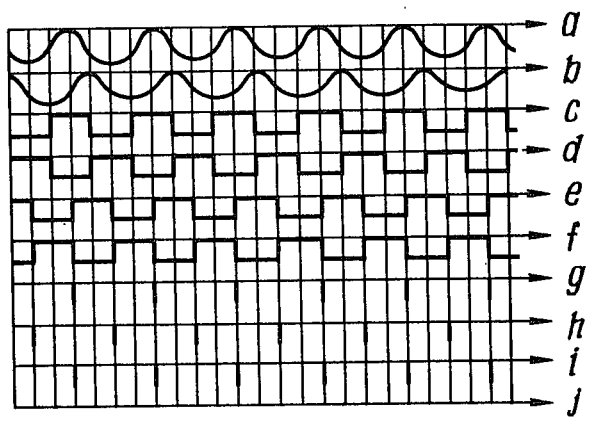
Figure 29:
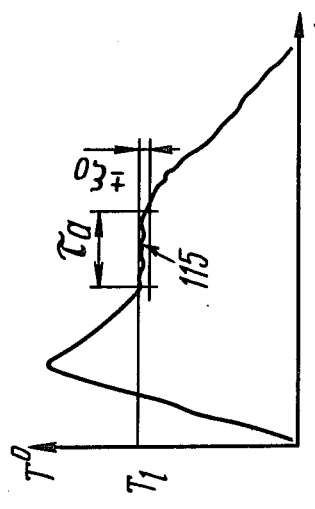
Figure 30:
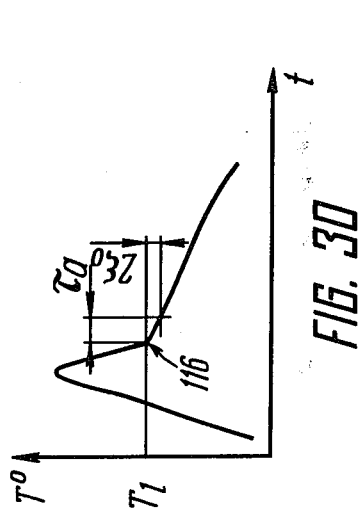
Figure 24:
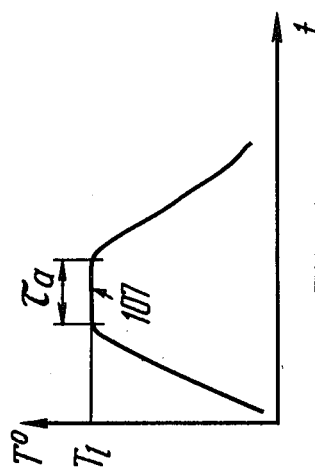
Figure 25:
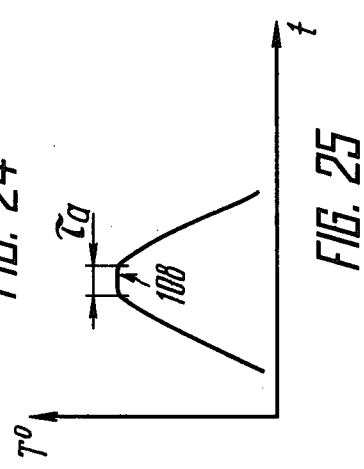
Figure 33:
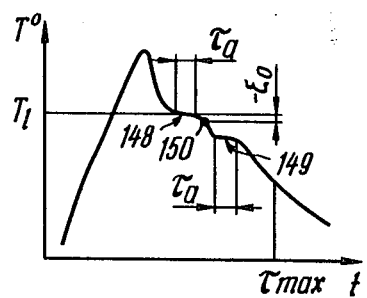
Figure 34:
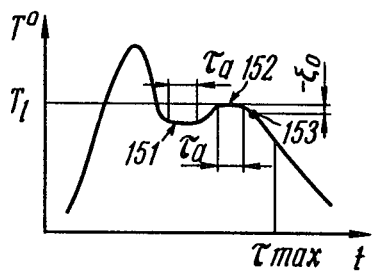
Figure 35:
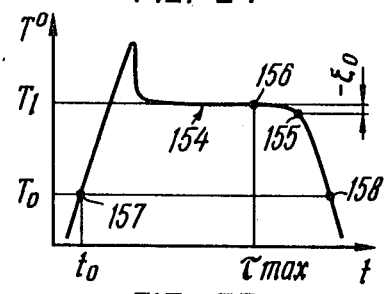

FIG. 21 a, b are examples of functional relationship between the crystallization temperature and the carbon concentration;

FIG. 22 a, b, c, d, e, f, g, h, i, j are time plots illustrating the operation of the converter in converting actual temperature of a metal into a numerical pulse code with a positive increment of temperature on the cooling curve;

FIG. 23 a, b, c, d, e, f, g, h, i, j are time plots illustrating the operation of the converter in converting the actual temperature of a metal into a numerical pulse code with a negative increment of temperature on the cooling curve;

FIG. 24 shows a cooling curve without an overheating portion, whereupon there is recorded a temperature stop corresponding to the crystallization temperature;

FIG. 25 shows a cooling curve without an overheating portion, whereupon there is recorded a false temperature stop which does not correspond to the crystallization temperature;

FIG. 26 a, b, c, d, e, f, g, h, i, j, k, l are time plots illustrating the operation of the unit for synchronizing code and clock pulses;

FIG. 27 shows a cooling curve whereupon there is recorded a false temperature stop which appears on the cooling curve prior to the end of the actual period of time when there appears a temperature stop corresponding to the crystallization temperature;

FIG. 28 shows a cooling curve whereupon there is recorded a false temperature stop which is in a period of cooling the molten metal below the crystallizaton temperature;

FIG. 29 shows a cooling curve whereupon certain temperature fluctuations are observed during the crystallization period;

FIG. 30 shows a cooling curve whereupon the crystallization period is characterized by a change in the curve's slope;

FIG. 31 a, b, c shows temperature stop portions on the cooling curve which illustrate the operating principle of the discriminator of local temperature increments shown in FIG. 17;

FIG. 32 shows a temperature stop portion on the cooling curve which illustrates the operating principle of the discriminator of local temperature increments shown in FIG. 18;

FIG. 33 is a cooling curve whereupon there are recorded two temperature stops, the first corresponding to the crystallization temperature, while the second is false;

FIG. 34 is a cooling curve whereupon there are recorded two temperature stops, the first being false, while the second corresponds to the crystallization temperature; and FIG. 35 is a cooling curve whereupon there is recorded a temperature stop of great duration.

The proposed digital device for automatically checking the carbon content in a metal with reference to temperature stops on a cooling curve may be used in combination with any known measuring device capable of recording a cooling curve of a molten metal sample.

A proposed device 1 (FIG. 1) is described hereinbelow in combination with a known measuring device (cf., for example, P. U. Dastur, C. B. Griffith and G. W. Perlix, Development of a Carbon and Temperature Probe for BOF Computer Control, Iron and Steel Engineering, March 1968) comprising a temperature sensor 2 and a recorder 3.

The proposed device 1 comprises a converter 4 which converts the actual temperature of the metal into a numerical pulse code, at whose input there arrives information on the actual temperature of metal. The input of the converter 4 is mechanically coupled to the recorder 3. There may be electric connection between the converter 4 and the recorder 3, as well as between the converter 4 and the temperature sensor 2.

The converter 4 has two outputs. Applied to one of these are code pulses corresponding to a positive increment of temperature on the cooling curve; applied to the other are code pulses corresponding to a negative increment of temperature on the cooling curve.

The output of the converter 4, whereto there is applied pulses corresponding to a positive increment of temperature on the cooling curve, is connected to a subtract input of a reversible counter 5. The output of the converter 4, whereto there is applied pulses corresponding to a negative increment of temperature on the cooling curve, is connected to an add input of the reversible counter 5. The reversible counter 5 converts the numerical pulse code into a parallel code. Said reversible counter 5 is constructed as a binary decade counter, but other versions are possible. The outputs of the converter 4 are also connected to respective code pulse inputs of a time interval discriminator 6. A clock pulse input of the time interval discriminator 6 is connected to an output of a clock pulse generator 7.

Digit outputs of the reversible counter 5 are connected to information inputs of a register 8 whereinto there is entered a code corresponding to a temperature stop on the cooling curve, said code being initiated by the counter 5. A control input of the register 8 is connected to an output of the time interval discriminator 6.

Digit outputs of the register 8 are connected to information inputs of a digital display unit 9.

In order to raise the reliability of the proposed device and to rule out malfunctions, the device includes a unit 10 (FIG. 2) for synchronizing code and clock pulses.

The synchronization unit 10 divides in time code and clock pulses.

Two inputs of the synchronization unit 10 are connected to the outputs of the converter 4 and a third input of said unit 10 is connected to the output of the generator 7.

An output of synchronized clock pulses of the synchronization unit 10 is connected to the clock pulse input of the time interval discriminator 6. Outputs of synchronized code pulses of the synchronization unit 10 are connected to the add and subtract inputs of the reversible counter 5 and to the respective code pulse inputs of the time interval discriminator 6.

In order to have a control signal applied to the input of the digital display unit 9 at the moment of detecting a temperature stop, the proposed device 1 includes a flip-flop 11 (FIG. 3) of a temperature stop on the cooling curve. A unity input of the flip-flop 11 is connected to the output of the time interval discriminator 6 and a unity output of the flip-flop 11 is connected to a control input of the digital display unit 9.

In order to limit the duration of a carbon content checking cycle and to rule out the detection of a false temperature stop, which appears on the cooling curve after a certain period of time during which the cooling curve has been processed, the proposed device includes a unit 12 for limiting the carbon content checking cycle. The device further includes a gate 13 for blocking clock pulses arriving at an input of the unit 12 for limiting the carbon content checking cycle and at the clock pulse input of the time interval discriminator 6. At an output of the unit 12 for limiting the carbon content checking cycle, there is formed a control signal after a certain period of time has passed since the beginning of the checking cycle. The output of the unit 12 for limiting the carbon content checking cycle is connected to a control input of the gate 13, and an output of the gate 13 is connected to the clock pulse input of the time interval discriminator 6 and to the input of the unit 12 for limiting the carbon content checking cycle.

A pulse input of the gate 13 is connected to the output of the generator 7. If the synchronization unit 10 is incorporated into the proposed device, the pulse input of the gate 13 is connected to the synchronized clock pulse output of the synchronization unit 10.

In order to form a control signal for switching on the digital display unit 9 at the moment when the carbon content checking cycle is ended, the proposed device further includes a coincidence circuit 14 (FIG. 4) for switching on the digital display unit 9.

Inputs of the coincidence circuit 14 are connected to the unity output of the flip-flop 11 of a temperature stop on the cooling curve and to the output of the unit 12 for limiting the carbon content checking cycle. An output of the coincidence circuit 14 is connected to the control input of the digital display unit 9.

In order to initiate signals as to the absence of a temperature stop on the cooling curve during the carbon content checking cycle, the proposed device includes a signal unit 15, which initiates a signal to repeat the carbon content checking cycle, and a coincidence circuit 16 for switching on the signal unit 15.

Inputs of the coincidence circuit 16 are connected to a zero output of the flip-flop 11 of a temperature stop on the cooling curve and to the output of the unit 12 for limiting the carbon content checking cycle. An output of the coincidence circuit 16 is connected to the input of the signal unit 15.

In order to make it possible to detect non-ideal temperature stops and to increase the potentialities of the proposed device, the device includes a discriminator 17 (FIG. 5) of local temperature increments on the cooling curve.

At one pulse output of the discriminator 17 there is formed a signal in case of a certain positive increment of temperature on the cooling curve. At a second pulse output of the discrimination 17 there is formed a signal in case of a certain negative increment of temperature on the cooling curve.

Inputs of the discriminator 17 of local temperature increments on the cooling curve are connected to the respective code pulse outputs of the converter 4. If the unit 10 is incorporated into the proposed device, the inputs of the discriminator 17 of local temperature increments on the cooling curve are connected to the respective synchronized code pulse outputs of the synchronization unit 10. The pulse outputs of the discriminator 17 are connected to the respective code pulse inputs of the time interval discriminator 6.

In order to make it possible to detect a temperature stop corresponding to the crystallization temperature on a cooling curve having a supercooling portion and in order to rule out the detection of false temperature stops which may appear on the cooling curve after the detection of a temperature stop corresponding to the crystallization temperature, the proposed device includes a coincidence circuit 18 (FIG. 6) to form a signal as to the detection of the crystallization temperature. The device further comprises gates 19 and 20 for blocking the passage of code pulses arriving at the inputs of the discriminator 17 of local temperature increments on the cooling curve.

Pulse inputs of the gates 19 and 20 are connected to the respective outputs of the converter 4. If the synchronization unit 10 is incorporated into the proposed device, the pulse inputs of the gates 19 and 20 are connected to the respective synchronized code pulse outputs of the synchronization unit 10.

Outputs of the gates 19 and 20 are connected to the respective inputs of the discriminator 17 of local temperature increments on the cooling curve.

Inputs of the coincidence circuit 18 are connected to the unity output of the flip-flop 11 of a temperature stop on the cooling curve and to an additional information output of the discriminator 17 of local temperature increments on the cooling curve. At said information output of the discriminator 17 there is formed a potential control signal in case of a certain negative increment of temperature on the cooling curve. The output of the coincidence circuit 18 is connected to the control inputs of the gates 19 and 20 and to the additional control input of the gate 13.

In order to reduce the time for transmitting information on carbon concentration to the digital display unit 9, the proposed device includes a dividing circuit 21 whose inputs are connected to the outputs of the coincidence circuits 14 and 18, and whose output is connected to the control input of the digital display unit 9.

In case the coincidence circuit 14 is not incorporated into the proposed device, the digital display unit 9 is switched on by directly connecting the output of the coincidence circuit 18 for forming a signal as to the detection of the crystallization temperature to the control input of the digital display unit 9.

Figure 7:
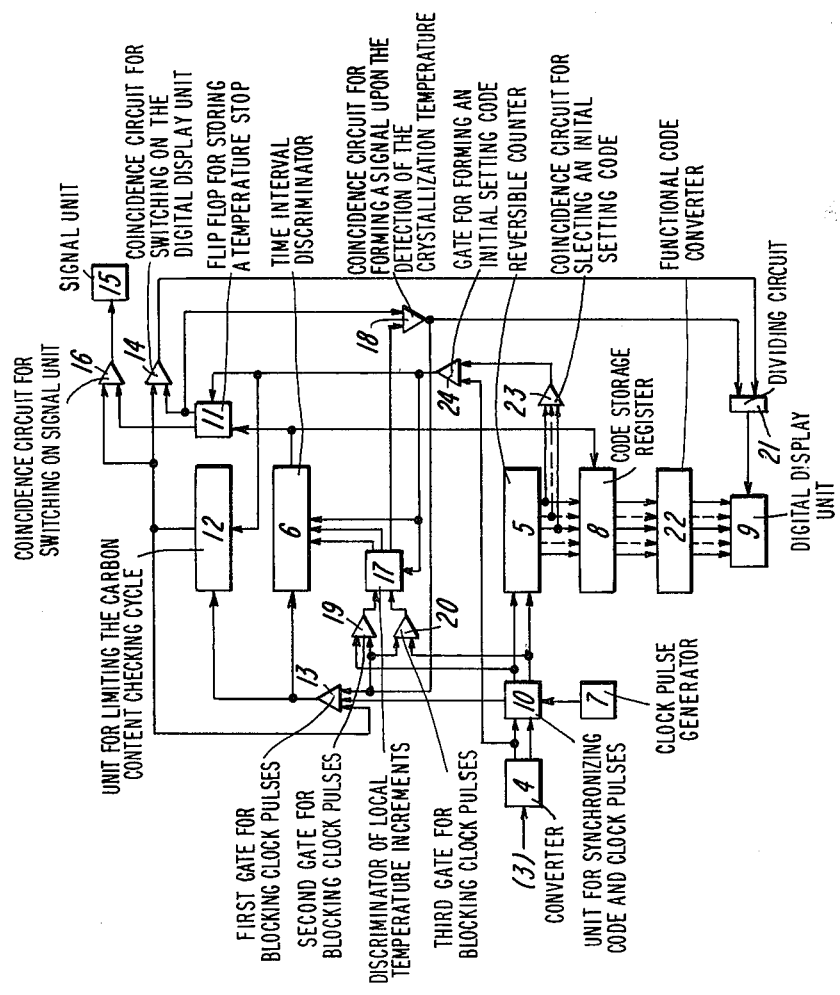
FIG. 7 is a block diagram of an alternative embodiment of the proposed device which ensures an automatic initial setting prior to the start of the checking cycle and makes it possible to functionally convert the crystallization temperature code into a carbon concentration code.

In order to ensure functional conversion of the crystallization temperature code into a carbon concentration code with reference to a certain relationship between these values, the device of the present invention includes a functional code converter 22 (FIG. 7).

Information inputs of the functional code converter 22 are connected to the digit outputs of the register 8, and information outputs of the functional converter 22 are connected to the information inputs of the digital display unit 9.

In order to automatically set the units of the proposed device into the initial state prior to the start of each carbon content checking cycle, the device includes a coincidence circuit 23 (FIG. 7) for selecting an initial setting code and a gate 24 for forming an initial setting pulse. Inputs of the coincidence circuit 23 are connected to the digit outputs of the reversible counter 5. An output of the coincidence circuit 23, whereat there is formed a signal in the presence of a certain code in the reversible counter 5, is connected to a control input of the gate 24. Another control input of the gate 24 is connected to the output of the converter 3 whereto there are applied code pulses corresponding to a positive increment of temperature on the cooling curve. The output of the gate 24 is connected to the initial setting inputs of the time interval discriminator 6, the unit 12 for limiting the carbon content checking cycle, the flip-flop 11 of a temperature stop of the cooling curve, and the discriminator 17 of local temperature increments on the cooling curve.

Figure 8:
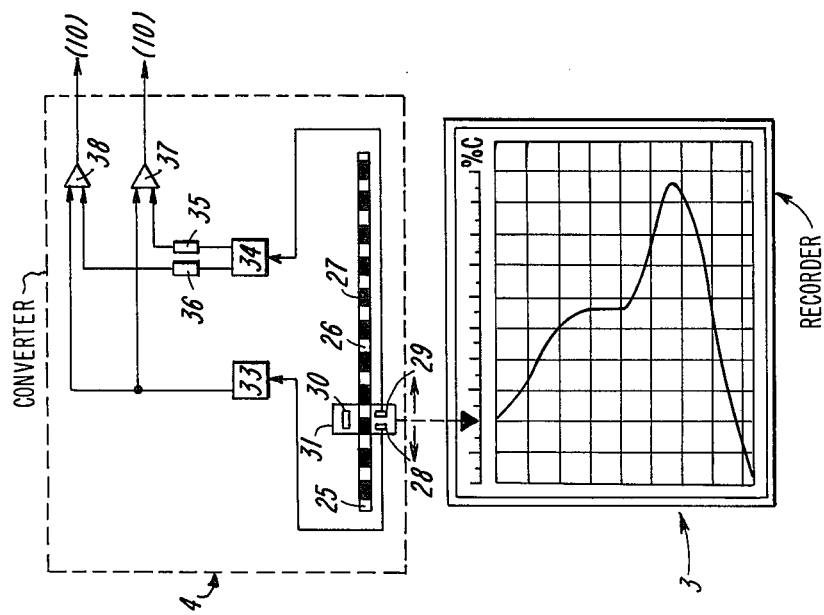
FIG. 8 is a functional diagram of a converter, which convert the actual temperature of a metal into a numerical pulse code, connected to a recorder.

FIG. 8 shows an alternative embodiment of the converter 4 which connects the actual temperature of the metal into a numerical pulse code. Other versions of said converter 4 are possible. The converter 4 comprises a measuring scale 25 (FIG. 8) whereupon there alternate transparent marks 26 and non-transparent marks 27 of an equal width. The number of the marks determines the resolving power of the converter 4. The converter 4 further comprises two photodiodes 28 and 29 and a luminary 30 which are mounted on a holder 31. The photodiodes 28 and 29 are spaced at a distance equal to half the width of the marks 26 and 27.

The holder 31 is mechanically coupled to a recording means 32 of the recorder 3.

In addition, the converter 4 includes two Schmidt flip-flops 33 and 34, two formers 35 and 36 of pulses on the positive front edge of signals arriving from the outputs of the Schmidt flip-flops, and two gates 37 and 38 for selecting code pulses corresponding to positive and negative temperature increments on the cooling curve.

The input of the Schmidt flip-flop 33 is connected to the output of the photodiode 28, whereas the input of the Schmidt flip-flop 34 is connected to the output of the photodiode 29. The zero output of the Schmidt flip-flop 33 is connected to the control inputs of the gates 37 and 38.

The unity output of the Schmidt flip-flop 34 is connected to the input of the pulse former 35 and the zero output of the Schmidt flip-flop 34 is connected to the input of the pulse former 36.

The output of the pulse former 35 is connected to the pulse input of the gate 37 and the output of the pulse former 36 is connected to the pulse input of the gate 38.

At the outputs of the gates 37 and 38 there are formed code pulses of the converter 4 corresponding to positive and to negative increments of temperature on the cooling curve.

There may be used other types of units to convert the actual temperature of the metal into a numerical pulse code.

The time interval discriminator 6 of the proposed device may be constructed as a time interval counter 39 (FIG. 9). The counting input of the counter 39 is the clock pulse input of the time interval discriminator 6.

Two initial setting inputs of the counter 39 form the code pulse inputs of the time interval discriminator 6. A third initial setting input of the counter 39 is the initial setting input of the discriminator 6.

The overflow output of the time interval counter 39 is the output of the time interval discriminator 6. At said output there arrives a pulse indicating overflowing of the time interval counter 39, which occurs at the moment of detecting a temperature stop on the cooling curve.

In order to make it possible to adjust the time interval discriminator 6, the latter may be constructed in a different way.

In this case the time interval discriminator also includes a switch unit 40 (FIG. 10) and a coincidence circuit 41.

The coincidence circuit 41 is intended for code selection in the time interval counter 39. The switch unit 40 makes it possible to change the code selected by the coincidence circuit 41.

Potential inputs of the coincidence circuit 41 are connected via the switch unit 40 to the digit outputs of the time interval counter 39.

Unity and zero outputs of each digit of the time interval counter 39 are connected to two poles of a respective switch of the switch unit 40. The center taps of all the switches of the switch unit 40 are connected to the potential inputs of the coincidence circuit 41. Thus, by changing the position of the switches of the unit 40, the inputs of the coincidence circuit 41 may be connected either to the unity or the zero outputs of a respective digit of the time interval counter 39. Let us assume, for example, that the required selected code is equal to the binary number 100100. In this case, the switches of the third and sixth digits of the switch unit 40 must be connected to the unity outputs, whereas the others must be connected to zero outputs.

The pulse input of the coincidence circuit 41 is combined with the counting input of the time interval counter 39. The output of the coincidence circuit 41 is the output of the time interval discriminator 6, whereto there is applied a pulse at a moment of detecting a temperature stop on the cooling curve.

In order to raise the accuracy of detecting a true temperature stop on the cooling curve, which corresponds to the crystallization temperature, and to rule out detection of false temperature stops, use may be made of a third alternative embodiment of the time interval discriminator 6.

In this case, the time interval discriminator 6 additionally has a second switch unit 42 (FIG. 11), a second coincidence circuit 43, a dividing circuit 44, and a flip-flop 45 of an over-heating portion of the cooling curve.

The potential inputs of the coincidence circuit 43 are connected via the switch unit 42 to the digit outputs of the time interval counter 39. The pulse input of the coincidence circuit 43 is combined with the pulse input of the coincidence circuit 41. The control input of the coincidence circuit 43 is connected to the zero output of the flip-flop 45 of an overheating portion of the cooling curve, and the control input of the coincidence circuit 41 is connected to the unity output of the flip-flop 45 of an overheating portion of the cooling curve.

The unity input of the flip-flop 45 of an overheating portion of the cooling curve is combined with the initial setting input of the time interval counter 39, whereto there are applied code pulses corresponding to a negative increment of temperature on the cooling curve. The initial setting input of the flip-flop 45 of an over-heating portion of the cooling curve is combined with the third initial setting input of the time interval counter 39.

The flip-flop 45 is intended for controlling the coincidence circuits 41 and 43, depending upon the type of the actual cooling curve. If the cooling curve has an overheating portion above a temperature stop portion, a permitting potential is applied to the control input of the coincidence circuit 41, whereas to the control input of the coincidence circuit 43 there is applied an inhibitory potential. If the cooling curve has no overheating portion above a temperature stop portion, an inhibitory potential is applied to the control input of the coincidence circuit 41, and a permitting potential is applied to the control input of the coincidence circuit 43.

With the aid of the switch units 40 and 42 it is possible to change the codes selected by the coincidence circuits 41 and 43.

The outputs of the coincidence circuits 41 and 43 are connected to the inputs of the dividing circuit 44. The output of the dividing circuit 44 is the output of the time interval discriminator 6, whereto there is applied a pulse at a moment of detecting a temperature stop.

FIG. 12 presents an alternative way of connecting the digital display unit 9 to the register 8. Other ways of connecting the digital display unit 9 to the register 8 are possible.

The register 8 comprises several decades 46 (FIG. 12) of the same type and two groups of input gates 47 and 48.

The inputs of the gates 47 form the information inputs of the register, whereto there are applied signals from the zero digit outputs of the respective decade of the reversible counter 5. The inputs of the gates 48 form the information inputs of the register, whereto there are applied signals from the unity digit outputs of the respective decade of the reversible counter 5.

The outputs of the gates 47 are connected to zero digit inputs of the decades 46 and the outputs of the gates 48 are connected to unity digit inputs of the decades 46. The control inputs of the gates 47 and 48 are combined and form the control input of the register 8.

The digital display unit 9 includes a decade decoder 49, switches 50 and indicator tubes 51.

Inputs of the decoder 49 form the information inputs of the digital display unit 9.

Outputs of the decoder 49 are connected to inputs of the switches 50. Control inputs of the switches 50 are combined and serve as the control input of the digital display unit 9.

A plate 52 of the indicator tube 51 is connected to a source of anode voltage $U_a$. Cathodes 53 of the indicator tube 51 are constructed in the form of 10 numbers and connected to the outputs of the switches 50.

FIG. 13 shows a preferred embodiment of the unit 10 for synchronizing code and clock pulses. The synchronization unit 10 has a clock pulse distribution sub-unit 54 (FIG. 13) and code pulse synchronization sub-units 55 and 56. The clock pulse distribution unit 54 comprises a flip-flop 57 for distributing clock pulses, a gate 58 for forming synchronized clock pulses, and a gate 59 for forming synchronizing clock pulses. Control inputs of the gates 58 and 59 are connected to outputs of the flip-flop 57. Pulse inputs of the gates 58 and 59 are combined and are connected to the counting input of the flip-flop 57 and serve as the input of the synchronization unit 10, whereto there are sent pulses from the clock pulse generator 7. The output of the gate 58 is the synchronized clock pulse output of the synchronization unit 10. The code pulse synchronization sub-units 55 and 56 comprise flip-flops 60 and 61 for storing code pulses, buffer flip-flops 62 and 63, coincidence circuits 64 and 65, and gates 66 and 67 for forming synchronized code pulses. The unity input of the flip-flop 60 is the input of the synchronization unit 10, whereto there are applied code pulses corresponding to a positive increment of temperature on the cooling curve. The unity input of the flip-flop 61 is the input of the synchronization unit 10, whereto there are applied code pulses corresponding to a negative increment of temperature on the cooling curve. The outputs of the coincidence circuit 64 are connected to the unity output of the flip-flop 60 and the zero output of the flip-flop 62. The inputs of the coincidence circuit 65 are connected to the unity output of the flip-flop 61 and the zero output of the flip-flop 63. The third input of each of the coincidence circuit 64 and 65 is connected to the output of the gate 59 for forming synchronizing clock pulses of the distribution sub-unit 54. The output of the gate 59 is also connected to one of the inputs of the gate 66 of the synchronization sub-unit 55 and to one of the inputs of the gate 67 of the synchronization sub-unit 56. The other inputs of each of the gates 66 and 67 are connected respectively to the unit outputs of the flip-flops 62 and 63. The output of the coincidence circuit 64 is connected to the unity input of the flip-flop 62, and the output of the coincidence circuit 65 is connected to the unity input of the flip-flop 63. The output of the gate 66 is connected to zero inputs of the flip-flops 60 and 62 and serves as the output of synchronized code pulses of the synchronization unit 10, whereto there are applied code pulses corresponding to a positive increment of temperature on the cooling curve. The output of the gate 67 is connected to zero inputs of the flip-flops 61 and 63 and serves as the output of synchronized code pulses of the synchronization unit 10, whereto there are applied code pulses corresponding to a negative increment of temperature on the cooling curve.

The unit 12 for limiting the carbon content checking cycle is constructed as a counter 68 (FIG. 14) for counting the duration of a carbon content checking cycle. The counting input of the counter 68 is the input of the unit 12 for limiting the carbon content checking cycle. The initial setting input of the counter 68 is the initial setting input of the unit 12 for limiting the carbon content checking cycle. The unity output of a top digit 69 of the counter 68 is the output of the unit 12 for limiting the carbon content checking cycle, whereto there is applied a control signal as to the end of the carbon content checking cycle.

In order to change the duration of a carbon content checking cycle, there is proposed an alternative embodiment of the unit 12 for limiting the carbon content checking cycle.

In this case, the unit 12 for limiting the carbon content checking cycle also comprises a switch unit 70 and a coincidence circuit 71. Inputs of the coincidence circuit 71 are connected via the switch unit 70 to the digit outputs of the counter 68 for counting the duration of a carbon content checking cycle. The unit and zero outputs of each digit are connected to two terminals of a respective switch of the switch unit 70. The center taps of all the switches of the switch unit 70 are connected to the inputs of the coincidence circuit 71. By changing the position of the switches of the switch unit 70, it is possible to connect to the input of the coincidence circuit 71 the unity or zero output of the respective digit of the counter 68 and thus change the code of the counter 68, which is selected by the coincidence circuit 71. The output of the coincidence circuit 71 is the control output of the unit 12 for limiting the carbon content checking cycle.

Figure 16:
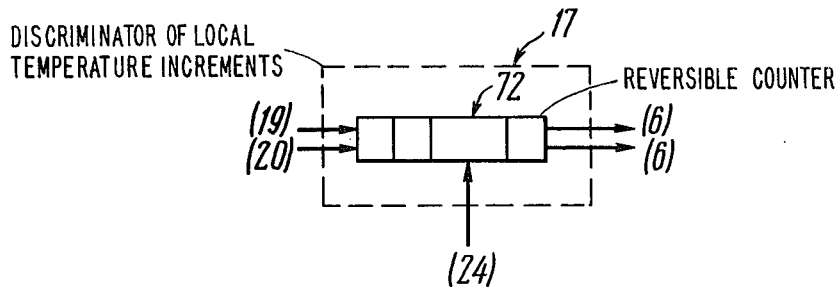
FIG. 16 is a functional diagram of a discriminator of local temperature increments on the cooling curve.

The discriminator 17 of local temperature increments on the cooling curve is constructed as a reversible counter 72 (FIG. 16) for determining local temperature increments on the cooling curve. Add and subtract inputs of the counter 72 are the inputs of the discriminator 17, whereto there are applied code pulses corresponding to positive and negative increments of temperature on the cooling curve.

The add overflow output of the counter 72 is the pulse output of the discriminator 17, whereto there is applied a signal in case of a certain positive increment of temperature on the cooling curve.

The subtract overflow output of the counter 72 is the pulse output of the discriminator 17, whereto there is applied a signal in case of a certain negative increment of temperature on the cooling curve.

The initial setting input of the counter 72 is the initial setting input of the discriminator 17.

In order to make it possible to change the parameters of the discriminator 17 of local temperature increments on the cooling curve and expand its functional potentialities, there is proposed an alternative embodiment of said discriminator 17.

This alternative embodiment of the discriminator 17 of local temperature increments on the cooling curve includes a reversible counter 73 (FIG. 17), for determining local temperature increments on the cooling curve, having a sign digit 74. The discriminator 17 further includes switch units 75 and 76, a coincidence circuit 77 at whose output there is formed a signal in case of a certain positive increment of temperature on the cooling curve, and a coincidence circuit 78 at whose output there is formed a signal in case of a certain negative increment of temperature on the cooling curve. The discriminator 17 still further includes a gate 79 for blocking the count of code pulses corresponding to a positive increment of temperature on the cooling curve, a gate 80 for blocking the count of code pulses corresponding to a negative increment of temperature on the cooling curve, and output gates 81 and 82. The add input of the counter 73 is connected to the output of the gate 79. The subtract input of the counter 73 is connected to the output of the gate 80. One initial setting input of the counter 73 is the initial setting input of the discriminator 17 of local temperature increments on the cooling curve. Two other initial setting inputs of the counter 73 are connected to the outputs of the gates 81 and 82. The unity output of the sign digit 74 of the counter 73 is connected to one of the inputs of the coincidence circuit 78. The zero output of the sign digit 74 of the counter 73 is connected to one of the inputs of the coincidence circuit 77. The unity and zero outputs of the remaining digits of the counter 73 are connected via the switch unit 75 to the other inputs of the coincidence circuit 77 and via the switch unit 76 to the other inputs of the coincidence circuit 78. The unity output and zero output of each said digit of the counter 73 are connected to the two poles of a respective switch of the switch unit 75 and to the two poles of a respective switch of the switch unit 76. The center taps of all the switches of the switch unit 75 are connected to the inputs of the coincidence circuit 77. The center taps of all the switches of the switch unit 76 are connected to the inputs of the coincidence circuit 78.

By changing the position of the switches of the switch unit 75, one can connect to the inputs of the coincidence circuit 77 the unity or zero output of the respective digit of the counter 73 and thus change the positive number code of the counter 73, selected by the coincidence circuit 77.

By changing the position of the switches of the switch unit 76, it is possible to connect to the inputs of the coincidence circuit 78 the unity or zero output of the respective digit of the counter 73 and thus change the negative number code of the counter 73, selected by the coincidence circuit 78.

The output of the coincidence circuit 77 is connected to the control inputs of the gates 79 and 81. The output of the coincidence circuit 78 is connected to the control inputs of the gates 80 and 82. The pulse inputs of the gates 79 and 81 are combined and serve as the input of the discriminator 17 of local temperature increments on the cooling curve, whereto there are applied code pulses corresponding to a positive increment of temperature on the cooling curve. The pulse inputs of the gates 80 and 82 are also combined and serve as the input of the discriminator 17 of local increments of temperature on the cooling curve, whereto there are applied code pulses corresponding to a negative increment of temperature on the cooling curve. The output of the gate 81 is the pulse output of the discriminator 17 of local increments of temperature on the cooling curve, whereto there is applied a signal in case of certain positive increment of temperature on the cooling curve The output of the gate 82 is the pulse output of the discriminator 17 of local increments of temperature on the cooling curve, whereto there is applied a signal in case of a certain negative increment of temperature on the cooling curve. The output of the coincidence circuit 78 is the information output of the discriminator 17 of local temperature increments, whereto there is applied a control signal in case of a certain negative increment of temperature on the cooling curve.

In order to raise the reliability of the discriminator 17 of local temperature increments on the cooling curve, there is proposed a third alternative embodiment of said discriminator 17.

This alternative embodiment of the discriminator 17 comprises a threshold unit 83 (FIG. 18) and a threshold unit 84. The threshold unit 83 has a reversible counter 85 for determining local temperature increments on the cooling curve, a switch unit 86, a coincidence circuit 87, a zero decoder 88, a gate 89 for blocking the count of code pulses corresponding to a positive increment of temperature on the cooling curve, a gate 90 for blocking the count of code pulses corresponding to a negative increment of temperature on the cooling curve, and an output gate 91. The threshold unit 84 comprises a reversible counter 92 for determining local temperature increments on the cooling curve, a switch unit 93, a coincidence circuit 94, a zero decoder 95, a gate 96 for blocking the count of code pulses corresponding to a positive increment of temperature on the cooling curve, a gate 97 for blocking the count of code pulses corresponding to a negative increment of temperature on the cooling curve, and an output gate 98. The add input of the reversible counter 85 is connected to the output of the gate 89. The subtract input of the reversible counter 85 is connected to the output of the gate 90. The add input of the reversible counter 92 is connected to the output of the gate 96. The subtract input of the reversible counter 92 is connected to the output of the gate 97. One initial setting input of the reversible counter 85 is connected to the output of the gate 91. One initial setting input of the reversible counter 92 is connected to the output of the gate 98. The two other initial setting inputs of the reversible counters 85 and to 86 of the threshold units 83 and 84 are combined and serve as the initial setting input of the discriminator 17 of local increments of temperature on the cooling curve. The unit and zero digit outputs of the reversible counter 85 are connected via the switch unit 86 to the inputs of the coincidence circuit 87. The unity and zero digit outputs of the reversible counter 92 are connected via the switch unit 93 to the coincidence circuit 94. The unity output and the zero output of each digit of the reversible counter 85 are connected to the two poles of a respective switch of the switch unit 86. The center taps of all the switches of the switch unit 86 are connected to the inputs of the coincidence circuit 87. The unity and zero digit outputs of the reversible counter 92 are connected in a similar manner via the switch unit 93 to the inputs of the coincidence circuit 94.

By changing the position of the switches of the switch unit 86, it is possible to connect to the inputs of the coincidence circuit 87 the unity or zero output of the respective digit of the reversible counter 85 and thus change the positive number code of the reversible counter 85, selected by the coincidence circuit 87. By changing in a similar manner the position of the switches of the switch unit 93, it is possible to change the negative number code of the counter 92, which is selected by the coincidence circuit 94.

The zero digit outputs of the reversible counter 85 are also connected to the inputs of the zero decoder 88. The zero digit outputs of the reversible counter 92 are also connected to the inputs of the zero decoder 95. The output of the coincidence circuit 87, whereat there is formed a signal in case of a certain positive increment of temperature on the cooling curve, is connected to the control inputs of the gates 89 and 91. The output of the coincidence circuit 94, whereat there is formed a signal in case of a certain negative increment of temperature on the cooling curve, is connected to the control inputs of the gates 97 and 98. The output of the zero decoder 88 is connected to the control input of the gate 90 for blocking the count of code pulses corresponding to a negative increment of temperature on the cooling curve. The output of the zero decoder 95 is connected to the control input of the gate 96 for blocking the count of code pulses corresponding to a positive increment of temperature on the cooling curve. The pulse inputs of the gates 89 and 91 of the threshold unit 83 are combined with the pulse input of the gate 96 of the threshold unit 84 and serve as the input of the discriminator 17 of local temperature increments on the cooling curve, whereto there are applied code pulses corresponding to a positive increment of temperature on the cooling curve. The pulse inputs of the gates 97 and 98 of the threshold unit 84 are combined with the pulse input of the gate 90 of the threshold unit 83 and serve as the input of the discriminator 17 of local temperature increments on the cooling curve, whereto there are applied code pulses corresponding to a negative increment of temperature on the cooling curve.

The output of the gate 91 is the pulse output of the discriminator 17, whereto there are applied signals in case of a certain positive increment of temperature on the cooling curve. The output of the gate 98 is the pulse output of the discriminator 17, whereto there are applied signals in case of a certain negative increment of temperature on the cooling curve.

The output of the coincidence circuit 94 is the information output of the discriminator 17, whereto there is applied a control signal in case of a certain negative increment of temperature on the cooling curve.

Figure 19:
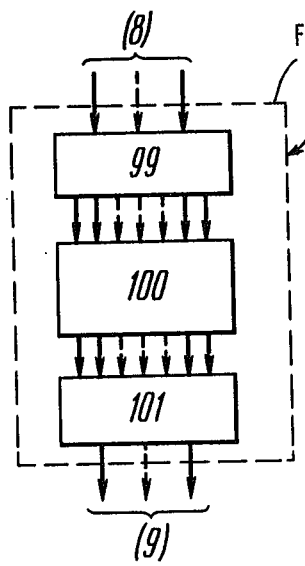
FIG. 19 is an alternative embodiment of a functional code converter.

The functional code converter 22 is constructed in the form of a combination circuit comprising a decoder 99 (FIG. 19); a switching unit 100, and a coder 101. The inputs of the decoder 99 are the information inputs of the functional code converter 22, whereto there are applied signals from the digit outputs of the register 8. The outputs of the decoder 99 are coupled via the switching unit 100 to the inputs of the coder 101. The outputs of the coder 101 are the information outputs of the functional converter 22, wherefrom there are applied signals to the information inputs of the digital display unit 9.

The switching unit 100 makes it possible to change the functional relationship between the temperature code corresponding to a temperature stop on the cooling curve and the carbon concentration code.

The operating principle of the proposed device 1 (FIG. 1) taken in combination with a conventional measuring device is as follows.

Figure 20:
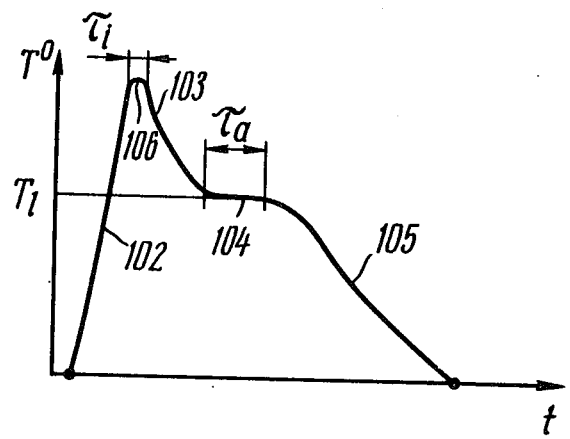
FIG. 20 shows an ideal cooling curve.

The metal temperature sensor 2 (FIG. 1) registers the change of the metal temperature with time. From the sensor 2, the signal is sent to the input of the recorder 3. The recording member 32 (FIG. 8) of the recorder 3 moves in accordance with the change in the temperature of the metal, and the recorder 3 plots a cooling curve of the sample of metal. An ideal cooling curve is shown in FIG. 20.

This cooling curve comprises the following characteristic portions:

a portion 102 (FIG. 20) corresponding to a period of heating the temperature sensor;

a portion 103 which is an overheating portion on the cooling curve (corresponding to the period when the molten metal is cooled to reach the crystallization temperature);

a portion 104 which is a temperature stop on the cooling curve (a period of crystallization of the metal); and a portion 105 which corresponds to the period when the solidified metal is cooled down below the crystallization temperature.

The temperature stop 104 corresponds to the crystallization temperature $T_1$ of the metal, whereas the temperature stop 106 is a false one.

The movement of the recording member 32 (FIG. 8) of the recorder 3 is converted with the aid of the converter 4 (FIG. 1) of the proposed device 1 into a numerical pulse code which is a sequence of code pulses. The number of code pulses across the output of the converter 4 is proportional to the magnitude of the linear displacement of the recording member 32 (FIG. 8) and, consequently, is proportional to the actual temperature of metal. Depending upon the direction of movement of the recording member 32 of the recorder 3, code pulses are applied to one of the two outputs of the converter 4 (FIG. 1).

From the converter 4, the code pulses are applied to the add and subtract inputs of the reversible counter 5. Prior to the start of operation, the recording member 32 (FIG. 8) of the recorder 3 (FIG. 1) is set into one of its extreme positions. Entered into the reversible counter 5, with the aid of an initial setting key (not shown in FIG. 1), is a code corresponding to this position of the recording member 32 (FIG. 8).

Figure 21A:
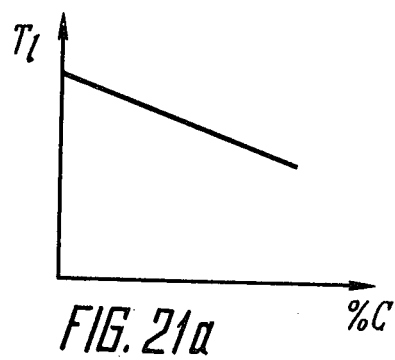
Figure 21B:
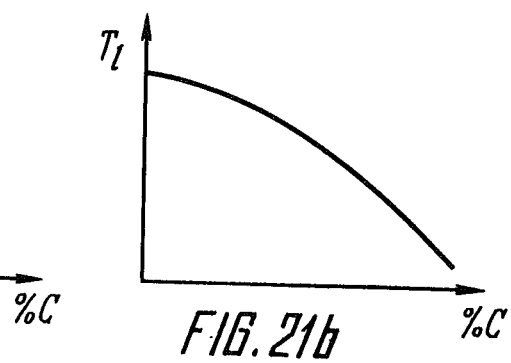

As the recording member 32 is moving in the direction corresponding to a positive increment of temperature on the cooling curve, the reversible counter 5 (FIG. 1) carries out subtraction of pulses. As the recording member 32 (FIG. 8) is moving in the direction corresponding to a negative increment of temperature on the cooling curve, the reversible counter 5 (FIG. 1) adds pulses. This is due to the fact that the relationship between the carbon concentration (C%) and the crystallization temperature $T_1$ is a strictly decreasing function (FIG. 21a, b). A binary-decimal code is formed in the reversible counter 5 (FIG. 1), which corresponds to the actual temperature of metal.

From the outputs of the converter 4, pulses are also applied to the pulse input of the time interval discriminator 6.

To the clock pulse input of the time interval discriminator 6, there are applied clock pulses from the generator 7.

At the moment of detecting a temperature stop on the cooling curve, at the output of the discriminator 6 there is formed a pulse which is applied to the control input of the register 8. As this takes place, the input gates 47 and 48 (FIG. 12) of the register 8 are driven into conduction, and a code from the reversible counter 5 (FIG. 1) is entered via the information input of the register 8 into its decades 46.

If the relationship between the carbon concentration (C%) and the crystallization temperature $T_1$ is linear (FIG. 21a), in the register 8 (FIG. 1) there is formed a binary-decimal code of carbon concentration in metal. From the register 8, the code is applied to the digital display unit 9 which indicates the carbon concentration in the metal. From the register 8, the code may also be sent to a computer (not shown in FIG. 1) which controls the steel smelting process.

The operating principle of the converter shown in FIG. 8 is illustrated by the time plots of FIGS. 22 and 23.

The movement of the recording member 32 (FIG. 8) of the recorder 3 is parallel to that of the holder 31 of the converter 4. The luminous flux of the luminary 30, which is incident on the photodiodes 28 and 29, is modulated by the marks 26 and 27 on the measuring scale 25.

From the photodiodes 28 and 29, there are applied signals to the inputs of the Schmidt flip-flops 33 and 34, respectively.

As the recording member 32 is moving from left to right, the signal (FIG. 22a) of the photodiode 28 (FIG. 8) is a quarter of a period behind the signal (FIG. 22b) of the photodiode 29 (FIG. 8). In this case, the signal (FIG. 22c) across the unity output and the signal (FIG. 22d) across the zero output of the Schmidt flip-flop 33 (FIG. 8) are a quarter of a period behind the signal (FIG. 22e) at the unity output and the signal (FIG. 22f) at the zero output of the Schmidt flip-flop 34 (FIG. 8), respectively.

The former 35 forms pulses (FIG. 22g) on the positive front edge of the signal (FIG. 22e) applied from the unity output of the Schmidt flip-flop 34 (FIG. 8). The former 36 forms pulses (FIG. 22h) on the positive front edge of the signal (FIG. 22f) applied from the zero output of the Schmidt flip-flop 34 (FIG. 8).

The pulses (FIG. 22g) from the output of the former 35 are applied to the pulse input of the gate 37. The pulses (FIG. 22h) from the output of the former 36 are applied to the pulse input of the gate 38. The signals (FIG. 22d) drom the zero output of the Schmidt flip-flop 33 (FIG. 8) are applied to the control inputs of the gate 37 and the gate 38. As is seen from the time plots (FIG. 22), at moments when signals are applied to the pulse input of the gate 37 (FIG. 8), said gate 37 is not conducting, as to its control input there is applied an inhibitory signal from the zero output of the Schmidt flip-flop 33. At moments when there are applied signals to the pulse input of the gate 38, said gate 38 is conducting, as to its control input there is applied a permitting signal from the zero output of the Schmidt flip-flop 33.

As the recording member 32 (FIG. 8) moves from left to right, there are formed no signals (FIG. 22i) across the output of the gate 37 (FIG. 8). The signals (FIG. 22j) across the output of the gate 38 (FIG. 8) are code pulses of the converter 4, corresponding to a positive increment of temperature on the cooling curve.

As the recording member 32 (FIG. 8) is moving from right to left, the signal (FIG. 23a) of the photodiode 28 (FIG. 8) is a quarter of a period behind the signal (FIG. 23b) of the photodiode 29 (FIG. 8). As a result, at moments when there arrive pulses (FIG. 23g) from the former 35 (FIG. 8) to the pulse input of the gate 37, there are applied permitting signals (FIG. 23d) to the control input of the gate 37 from the zero output of the Schmidt flip-flop 33 (FIG. 8). At moments when there arrive pulses (FIG. 23h) from the former 36 (FIG. 8) to the pulse input of the gate 38, there are applied inhibitory signals (FIG. 23d) to the control input of the gate 38 from the zero output of the Schmidt flip-flop 33 (FIG. 8).

Hence, as the recording member 32 (FIG. 8) moves from right to left, there are formed no signals (FIG. 23j) at the output of the gate 38 (FIG. 8). The signals (FIG. 23i) at the output of the gate 37 (FIG. 8) are code pulses of the converter 4, corresponding to a negative increment of temperature on the cooling curve.

The operating principle of the time interval discriminator 6 (FIG. 1), according to the first alternative embodiment thereof (FIG. 9) is as follows.

In the initial state, with the aid of an initial setting key (not shown) or automatically, as will be shown below, the counter 39 is set to zero.

Clock pulses are applied to the counting input of the counter 39 (FIG. 9) of time intervals which is an add counter. Code pulses are applied to the initial setting inputs of the time interval counter 39.

After each initial setting of the counter 39 by a code pulse, the counter 39 again begins counting a time interval, i.e. counting clock pulses. After a certain period of time $\tau_o$ has elapsed since an initial setting of the counter 39, a pulse is formed at the latter's overflow output. The overflow pulse is formed if during said period of time $\tau_o$ the counter 39 is not brought to its initial state by another code pulse.

The period of time $\tau_o$ (the time threshold) is selected within the following limits:

$$\tau_i < \tau_o < \tau_a$$

where $\tau_a$ is the minimum possible duration of a temperature stop on the cooling curve, corresponding to the crystallization temperature (FIG. 20); and $\tau_i$ is the maximum duration of the temperature stop 106 (FIG. 20) on the cooling curve, which does not correspond to the crystallization temperature.

As a result, on the portions 102, 103, and 105 (FIG. 20) of the cooling curve, where there is no temperature stop, the counter 39 is always set in the initial state by code pulses, with no pulse being formed at the overflow output. During the crystallization periods, when there appears a temperature stop on the cooling curve, corresponding to the crystallization temperature $T_1$ (the portion 104 of FIG. 20), code pulses are not applied to the initial setting inputs of the counter 39 during the period of time $\tau_a$. Hence, as soon as there passes a period of time $\tau_o$ since the moment of the arrival of the last code pulse, there is formed a pulse at the overflow output of the counter 39.

The overflow pulse of the counter 39 is applied to the output of the time interval discriminator 6.

The time value of the threshold $\tau_o$ may be changed by adjusting the time interval discriminator 6 through changing the clock pulse frequency of the generator 7 (FIG. 2). This type of adjustment is not always convenient, however, so it is more practicable to use the second embodiment of the time interval discriminator (FIG. 10).

The position of the switches of the switch unit 40 (FIG. 10) must correspond to a binary number $\bar{n}_o$ which is found as follows:

$$n_o = \tau_o \cdot f_1 - 1,$$

where
$f_1$ is the clock pulse frequency at the input of the time interval discriminator 6; and
$\tau_o$ is the required time value of the threshold in sec.

For example, if the optimum value of the threshold $\tau_o$ is assumed to be equal to 3.5 sec, and the clock pulse frequency $f_1$ at the input of the time interval discriminator 6 is 4 Hz, it is inferred that $n_o = 13$ (the binary number $\bar{n}_o = 1101$). Hence, the switches of the first, third and forth digits of the switch unit 40 must be connected to the unity outputs of the respective digits of the counter 39, whereas the rest must be connected to the zero outputs.

The clock pulses are applied to the pulse input of the coincidence circuit 41. If the number $n_o$ of clock pulses is applied to the counting input of the counter 39 after the latter has been set by a code pulse, a binary code $\bar{n}_o$ is formed in the counter 39. The code $\bar{n}_o$ is selected by the coincidence circuit 41. At the moment of the arrival of the next clock pulse, a pulse is formed at the output of the coincidence circuit 41. A pulse at the output of the coincidence circuit 41 is formed only in case there appears a temperature stop on the cooling curve, for on the remaining portions of the curve the counter 39 is invariably set in the initial state by code pulses and cannot reach the number $\bar{n}_o$.

From the output of the coincidence circuit 41, the pulse is applied to the output of the time interval discriminator 6.

In practical work, one comes across cooling curves that are different from the ideal cooling curve shown in FIG. 20. There are, for example, cooling curves (FIGS. 24 and 25) without any overheating portion. This type of curve is accounted for by a low initial temperature of metal and by an inadequate response speed of the metal temperature sensor (FIG. 1).

On a cooling curve without an overheating portion, there may appear a true temperature stop 107 (FIG. 24), which corresponds to the crystallization temperature $T_1$, and a false temperature stop 108 (FIG. 25) which does not correspond to the crystallization temperature. The duration of the false temperature stop 108 (FIG. 25) may be equal to that of the true temperature stop 104 (FIG. 20) on a cooling curve having an overheating portion. Hence, in order to provide for maximum accuracy of determining true temperature stops, the optimum time value of the threshold $\tau_o$ for curves without overheating portions (FIGS. 24 and 25) must be greater than the optimum value of the threshold $\tau_o$ for curves having overheating portions (FIG. 20).

In practice, different types of cooling curves appear at random. Hence, it is more practicable to employ the third embodiment of the time interval discriminator 6 shown in FIG. 11, which ensures automatic readjustment of the threshold $\tau_o$, depending upon the type of the cooling curve.

In this case, the position of the switches of the switch unit 40 (FIG. 11) must correspond to the binary number $\bar{n}'_o$ which is found as follows:

$$n_o' = \tau_o' \cdot f_1 - 1,$$

where
$f_1$ is the clock pulse frequency at the input of the time interval discriminator 6, Hz; and
$\tau_o'$ is the optimum time value of the threshold for a curve with an overheating portion, sec.

The position of the switches of the switch unit 42 must correspond to the binary number $\bar{n}_o''$ which is found as follows:

$$\bar{n}_o'' = \tau_o'' f_1 - 1,$$

where
$\tau_o''$ is the optimum time value of the threshold, in sec., for a curve without an overheating portion.

For example, if the optimum time value of the threshold $\tau_o'$ is assumed to be equal to 3.5 sec, the optimum time value of the threshold $\tau_o''$ is assumed to be equal to 6 sec. and the clock pulse frequency $f_1$ at the input of the discriminator 6 is 4 Hz, it is inferred that $n_o' = 13$ (the binary number $\bar{n}_o' = 1101$), and $n_o'' = 23$ (the binary number $\bar{n}_o'' = 10111$). Hence, the switches of the first, third and fourth digits of the switch unit 40 must be connected to the unity outputs of the respective digits of the counter 39, while the rest must be connected to the zero outputs. The switches of the first, second, third and fifth digits of the switch unit 42 must be connected to the unity outputs of the respective digits of the counter 39, while the rest must be connected to the zero outputs.

In the initial state, the flip-flop 45 (FIG. 11) of an overheating portion on the cooling curve is zeroed either with the aid of an initial setting key (not shown in FIG. 11) or automatically as will be shown below. As this takes place, the signal applied from the zero output of the flip-flop 45 drives the coincidence circuit 43 into conduction, whereas the signal from the unity output of the flip-flop 45 renders the coincidence circuit 41 non-conducting. If there is no overheating portion (FIGS. 24 and 25) on the cooling curve, with the appearance on the cooling curve of a temperature stop, the flip-flop 45 (FIG. 11) remains in the zero state, because prior to the appearance of the temperature stop, only code pulses have been applied to the input of the discriminator 6, which correspond to a positive increment of temperature on the cooling curve. As soon as the number $n_o''$ of clock pulses has been applied to the counting input of the counter 39 following another initial setting of said counter 39, there is formed the code $\bar{n}_o''$ in said counter 39. The code $\bar{n}_o''$ is selected by the coincidence circuit 43. At the moment of the arrival of the next clock pulse, there is formed a pulse at the outut of the coincidence circuit 43. Thus, if there is no overheating portion on the cooling curve, there is formed a pulse at the output of the coincidence circuit 43 only if on the cooling curve there appears a temperature stop whose duration is in excess of the preset threshold $\tau_o''$.

If an overheating portion 103 (FIG. 20) is recorded on the cooling curve, to the input of the time interval discriminator 6 there are applied code pulses corresponding to a negative increment of temperature on the cooling curve. The first of these pulses sets the flip-flop 45 into the unity state. The flip-flop 45 drives the coincidence circuit 41 into conduction and renders the coincidence circuit 43 non-conducting. As soon as there is applied the $n_o'$ number of clock pulses to the counting input of the counter 39 following its initial setting, the binary code $\bar{n}_o'$ is formed in the counter 39. The code $\bar{n}_o'$ is selected by the coincidence circuit 41. At the moment of the arrival of the next clock pulse, a pulse is formed at the output of the coincidence circuit 41. Thus, if there is an overheating portion on the cooling curve, at the output of the coincidence circuit 41 there is formed a pulse in case of the appearance on the cooling curve of a temperature stop whose duration is in excess of the preset threshold $\tau_o'$.

From the output of the coincidence circuit 41 or from the output of the coincidence circuit 43, the pulse is applied via the dividing circuit 44 to the input of the discriminator 6 and then to the control input of the register 8 (FIG. 1).

In the course of operation of the first embodiment (FIG. 1) of the proposed device 1, code pulses from the converter 4 may in some cases coincide in time with clock pulses from the generator 7. This may result in malfunctions (this applies to embodiments shown in FIGS. 9 through 12). For example, the counter 39 (FIGS. 9, 10 and 11) may make counting errors if a clock pulse and a code pulse are applied simultaneously to its counting input and initial setting input, respectively. Simultaneous application of a code pulse to the add input or the subtract input of the reversible counter 5 (FIG. 1) and of a pulse from the output of the discriminator 6 to the control input of the register 8 may lead to code rewriting in the course of the transient response in the reversible counter 5. As a result, a wrong code may be entered into the register 8.

With this in view, it is more practicable to use the second embodiment of the proposed device, shown in FIG. 2, which provides for synchronization (division in time) of code and clock pulses.

From the converter 4 (FIG. 2), code pulses are applied to the two inputs of the unit 10 for synchronizing code and clock pulses. Clock pulses from the generator 7 are applied to the third input of the unit 10. Synchronized code pulses are applied from the two inputs of the unit 10 to the add and subtract inputs of the reversible counter 5 and to the respective code pulse inputs of the time interval discriminator 6. Synchronized clock pulses from the third input of the unit 10 are applied to the clock pulse input of the discriminator 6. The moments of arrival of the synchronized code pulses and of the synchronized clock pulses are strictly divided in time.

The operating principle of the embodiment of the unit 10 for synchronizing code and clock pulses, shown in FIG. 13, is illustrated by a time plot (FIG. 26). It is as follows.

As clock pulses (FIG. 26a) are applied from the generator 7 (FIG. 2) to the counting input of the flip-flop 57 (FIG. 13) of the clock pulse distribution sub-unit 54, said flip-flop 57 successively changes its state. The signals from the unity (FIG. 26c) and zero (FIG. 26b) outputs of the flip-flop 57 (FIG. 13) are applied to the control inputs of the gates 58 and 59, respectively. Applied to the pulse inputs of these gates are clock pulses (FIG. 26a) from the generator 7 (FIG. 2). As a result, at the outputs of said gates there are formed two series of pulses shifted in time relative to each other. At the output of the gate 58 (FIG. 13) there are formed synchronized clock pulses (FIG. 26d) and at the output of the gate 59 (FIG. 13) there are formed synchronizing clock pulses (FIG. 26e).

The repetition frequency $f_1$ of the synchronized clock pulses is equal to the repetition frequency $f_2$ of the synchronizing clock pulses and amounts to $$f_1 = f_2 = \tfrac{1}{2} f_o,$$

where $f_o$ is the repetition frequency of pulses arriving from the output of the clock pulse generator 7 (FIG. 2).

The synchronized clock pulses are applied to the respective output of the synchronization unit 10.

The synchronizing clock pulses are applied to the inputs of the coincidence circuit 64 (FIG. 13) and the gate 66 of the synchronization sub-unit 56. In the initial state, all the flip-flops 60, 61, 62 and 63 are zeroed by an initial setting key (not shown in FIG. 13). As a code pulse is applied from the output of the converter 4 (FIG. 2), which code pulse corresponds to a positive increment of temperature on the cooling curve, the flip-flop 60 (FIG. 13) is set into the unity state (FIG. 26h). After a change in the state of the flip-flop 60 (FIG. 13) at the moment of the arrival of the next synchronizing clock pulse, at the output of the coincidence circuit 64 there is formed a pulse (FIG. 26i). This pulse sets the buffer flip-flop 62 (FIG. 13) in the unity state (FIG. 26k); and as a result, the gate 66 (FIG. 13) is driven into conduction. At the moment of the arrival of the following synchronizing clock pulse (FIG. 26e,j), at the output of the gate 66 (FIG. 13) there is formed a synchronized code pulse (FIG. 26l) corresponding to a positive increment of temperature on the cooling curve. This pulse is applied to the respective output of the synchronization unit 10 (FIG. 13), as well as to the inputs of the flip-flops 60 and 62. The signal (FIG. 26j) applied from the zero output of the flip-flop 62 (FIG. 13) to one of the inputs of the coincidence circuit 64 prevents the arrival of a pulse at the unity input of the flip-flop 62 at the moment a pulse is applied to the zero input of the flip-flop 62. The formed synchronized code pulse sets the flip-flops 60 and 62 in the zero state and thus prepares the synchronization sub-unit 55 for the arrival of the next code pulse.

In the course of operation of the synchronization sub-unit 55, there may be partial coincidence in time of the code pulse and the synchronizing clock pulse. This may result in an "inadequate" pulse 109 (FIG. 26i) at the output of the coincidence circuit 64 (FIG. 13), i.e. a pulse of an insufficient duration or amplitude. In such a case, the buffer flip-flop 62 may remain in the zero state until there is applied another synchronizing clock pulse to the input of the coincidence circuit 64. At the moment of the arrival of the next synchronizing clock pulse, the state of the flip-flop 60 cannot be changed, so at this moment at the output of the coincidence circuit 64 there appears a second "adequate" pulse 110 (FIG. 26i). This pulse sets the flip-flop 62 (FIG. 13) into the unity state. At the moment of the arrival of the next synchronizing clock pulse (FIG. 26e), at the output of the gate 66 there is formed a synchronized code pulse (FIG. 26l) which is applied to the respective output of the synchronization unit 10 (FIG. 13) and simultaneously sets the flip-flops 60 and 62 in the zero state.

Synchronized code pulses corresponding to a negative increment of temperature on the cooling curve are formed in a similar manner at the output of the gate 67 of the synchronization sub-unit 56. These pulses are applied to the respective output of the synchronization unit 10.

Thus, the coincidence in time of pulses formed at the output of the gates 66 and 67 with those applied from the output of the gate 59 of the pulse distribution unit 54 ensures division in time of synchronized clock pulses and synchronized code pulses.

In order to ensure reliable operation of the synchronization unit 10, it is necessary that the repetition frequency $f_2$ of the synchronizing clock pulses should be double or treble the maximum repetition frequency $f_{3\ max}$ of the code pulses arriving from the output of the converter 4 (FIG. 2), i.e.

$$f_2 \geqq 3 f_{3\ max}.$$

Hence, the pulse frequency at the output of the generator 7 must be $$f_o = 2 f_2 \geqq 6 f_3.$$

In the course of operation of the first two embodiments of the proposed device shown in FIGS. 1 and 2, information on the results of the carbon content checking is continuously fed to the digital display unit 9. The device is intended for multiple operation, so prior to the start of each checking cycle, it is advisable to erase the results of the previous carbon content checking cycle so as to prepare the personnel for the perception of fresh data.

For this purpose, the proposed device comprises the flip-flop 11 (FIG. 3) of a temperature stop on the cooling curve.

In the initial state, with the aid of an initial setting key (not shown) or automatically, as will be described below, the flip-flop 11 is set in its zero state. An inhibitory signal from the unity output of the flip-flop 11 is applied to the control input of the digital display unit 9. As this takes place, the switches 50 (FIG. 12) of the digital display unit 9 are closed. Thus, the feed circuit of the indicator tubes 51 is disconnected, and the latter go out. At a moment of detecting a temperature stop on the cooling curve, a pulse from the output of the time interval discriminator 6 (FIG. 3) is applied to the unity input of the flip-flop 11. The flip-flop 11 is set in the unity state. As a result, a permitting signal is applied from its unity output to the switches 50 (FIG. 12) of the digital display unit 9. As a result, the feed circuit of the indicator tubes 51 is closed, the tubes 51 come on and provide a digital display of the given carbon content checking cycle.

A temperature stop on the cooling curve, which corresponds to the crystallization temperature, may appear on the cooling curve only within a certain period of time $\tau_{max}$ from the start of the carbon content checking cycle. Hence, if on the cooling curve there appears a temperature stop 111 (FIG. 27) before said period of time $\tau_{max}$ has elapsed, such a temperature curve is a false one.

In order to rule out detection of the false temperature stop 111, the proposed device incorporates the unit 12 (FIG. 3) for limiting the carbon content checking cycle.

Prior to the start of each carbon content checking cycle, the unit 12 for limiting the carbon content checking cycle is set in its initial state, which operation is either done with the aid of an initial setting key (not shown in FIG. 3) or automatically as will be shown below. As this takes place, from the output of the unit 12 there is sent a permitting potential to the control input of the gate 13 for blocking clock pulses. Clock pulses from the generator 7 or synchronized clock pulses from the output of the synchronization unit 10 (FIG. 3) are sent via the conducting gate 13 to the clock pulse input of the time interval discriminator 6 and to the input of the unit 12 for limiting the carbon content checking cycle. After a certain period of time $\tau_{max}$ has elapsed from the moment of initial setting the unit 12, at the output of said unit 12 there appears a signal as to the end of the checking cycle. From the output of the unit 12, the signal is applied to the control input of the gate 13. The gate 13 is rendered non-conducting, so clock pulses cease to arrive at the input of the unit 12 and at the clock pulse input of the discriminator 6. The unit 12 stops counting the checking cycle duration, so the signal at its output is blocked. In addition, due to the cessation of the arrival of clock pulses at the input of the discriminator 6, there is no possibility of detecting the false temperature stop 111 (FIG. 27) that appears on the cooling curve after the carbon content checking time $\tau_{max}$ has elapsed.

Figure 14:
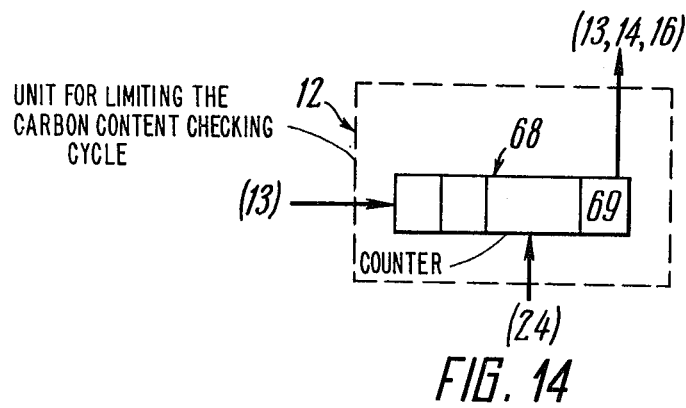
FIG. 14 is a functional diagram of a unit for limiting the carbon content checking cycle.
Figure 15:
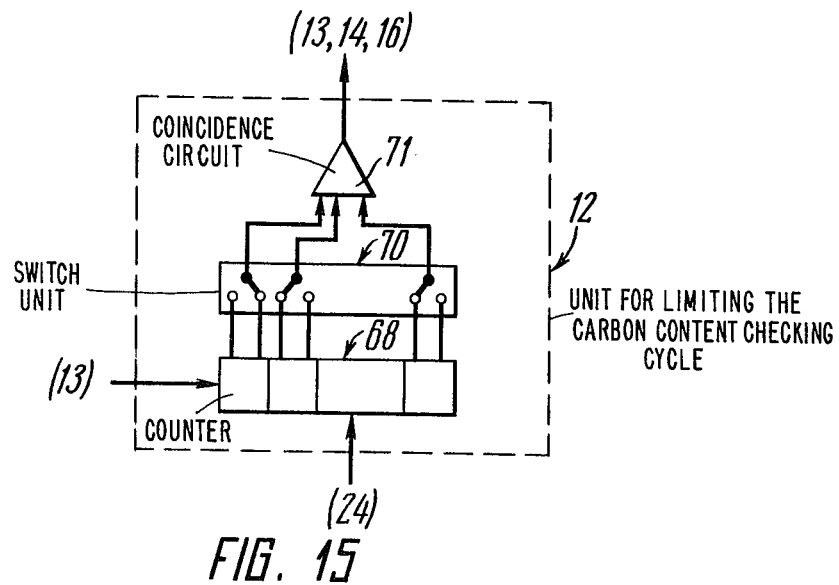
FIG. 15 is a functional diagram of a unit for limiting the carbon content checking cycle, wherein it is possible to adjust the duration of the carbon content checking cycle.

Preferred embodiments of the unit 12 for limiting the carbon content checking cycle are shown in FIGS. 14 and 15.

In the simplest case, the unit 12 comprises a counter 68 (FIG. 14) for counting the duration of the carbon content checking cycle, which operates as an add counter. Prior to each carbon content checking cycle, the counter 68 is zeroed either with the aid of an initial setting key (not shown in FIG. 14) or automatically as will be shown below. Clock pulses are applied to the counting input of the counter 68. As soon as a certain number of clock pulses have arrived at the counting input of the counter 68, which number corresponds to a preset value $\tau_{max}$, a control signal is formed at the unity output of the top digit 69 of the counter 68. From the unity output of the top digit 69 of the counter 68, the signal is applied to the output of the unit 12. As soon as there appears said signal at the output of the unit 12, clock pulses cease to arrive at the counting input of the counter 68. Due to this, the control signal remains at the unity output of the top digit 69 of the counter 68 until the counter 68 is set in its initial state prior to the start of another carbon content checking cycle.

For greater convenience in operation, it is desirable to be able to change the duration $\tau_{max}$ of the carbon content checking cycle. Hence, it is more practicable to use the second embodiment of the unit 12 for limiting the carbon content checking cycle, which embodiment is shown in FIG. 15.

The position of the switches of the switch unit 70 (FIG. 15) must correspond to the binary number $\bar{n}_{max}$ which is found as follows:

$$n_{max} = \tau_{max} \cdot f_1,$$

where
$\tau_{max}$ is the predetermined duration of the carbon content checking cycle, sec; and
$f_1$ is the clock pulse frequency at the input of the unit 12 for limiting the carbon content checking cycle, Hz.

For example, if the predetermined duration of the carbon content checking cycle $\tau_{max}$ is 30 sec, and the clock pulse frequency $f_1$ at the input of the unit 12 is 4 Hz, the number $n_{max}$ is equal to 120 (the binary number $n_{max} = 1111000$). Hence, the switches of the fourth, fifth, sixth and seventh digits of the switch unit 70 must be connected to the unity outputs of the respective digits of the counter 68, whereas the rest are to be connected to the zero outputs.

As soon as the number of clock pulses equal to $n_{max}$ has arrived at the counting input of the counter 68 following its initial setting, the binary code $\bar{n}_{max}$ is formed in said counter 68. This code is selected by the coincidence circuit 71. At the moment the code $\bar{n}_{max}$ is formed in the counter 68, there appears a control signal at the output of the coincidence circuit 71, which signal is applied at the output of the unit 12.

Sometimes on a cooling curve there is recorded a supercooling portion indicating a temperature below the crystallization temperature. This supercooling portion is recorded in the form of a temperature stop 112 (FIG. 28), after which there follows a true temperature stop 113 corresponding to the crystallization temperature $\tau_1$. In view of this, it is more rational to transmit information on the results of a carbon content checking cycle to the digital display unit 9 not at the moment of the detection of the first temperature stop, but at the moment when the carbon content checking cycle has ended. For this purpose, the proposed device comprises the coincidence circuit 14 (FIG. 4) for switching on the digital display unit 9.

At the moment of detecting the first temperature stop 112 (FIG. 28), a pulse from the output of the discriminator 6 enters the code, as it has been described above, from the reversible counter 5 to the register 8 and sets the flip-flop 11 in the unity state. The permitting signal from the unity output of the flip-flop 11 is applied to one input of the coincidence circuit 14. At this moment, no signal is applied to the control input of the digital display unit 9. At the moment of detecting the second temperature stop 113 (FIG. 28), a pulse from the output of the discriminator 6 enters a new code into the register 8 (FIG. 4) from the reversible counter 5, which new code corresponds to the crystallization temperature. At the moment when the carbon content checking cycle is over, there is applied a control signal from the output of the unit 12 for limiting the carbon content checking cycle to the second input of the coincidence circuit 14. At this moment, at the output of the coincidence circuit 14 (FIG. 4) (at the point 114 on the cooling curve as shown in FIG. 28) there appears a control signal. This signal is applied at the control input of the digital display unit 9 which indicates the result of the given carbon content checking cycle.

If there is no temperature stop (FIG. 27) on the cooling curve during the period of time $\tau_{max}$ (the duration of the carbon content checking cycle), the flip-flop 11 remains in the zero state. The permitting potential from the zero output of the flip-flop 11 is applied to the coincidence circuit 16 (FIG. 4). As a result, the signal unit 15 initiates a signal to repeat the carbon content checking cycle. At the moment when the carbon content checking cycle is over, at the second input of the coincidence circuit 16 there is applied a permitting signal from the output of the unit 12. The signal at the output of the coincidence circuit 16 initiates a signal to repeat the carbon content checking cycle.

In a number of cases, there may be slight temperature fluctuations in the course of crystallization, which are recorded on the cooling curve in the form of a non-ideal temperature stop 115 (FIG. 29). Sometimes the crystallization period is marked by a change of slope of the cooling curve and the appearance thereon of a bending point 116 (FIG. 30) which corresponds to the crystallization temperature $T_1$.

In order to make it possible to check the carbon content in metal with reference to cooling curves shown in FIGS. 29 and 30, the proposed device includes the discriminator 17 (FIG. 5) of local temperature increments on the cooling curve.

Applied to the respective inputs of the discriminator 17 are either code pulses from the converter 4 or synchronized code pulses from the synchronization unit 10.

The discriminator 17 is constructed so that if a local increment of temperature on the cooling curve is in excess of a predetermined threshold $\pm \epsilon_o$, a signal is applied to one of the pulse outputs of the discriminator 17. From the outputs of the discriminator 17, the pulses are applied to the respective inputs of the time interval discriminator 6 and set the counter 39 (FIGS. 9, 10 and 11) of said discriminator in the initial state.

Figure 5:
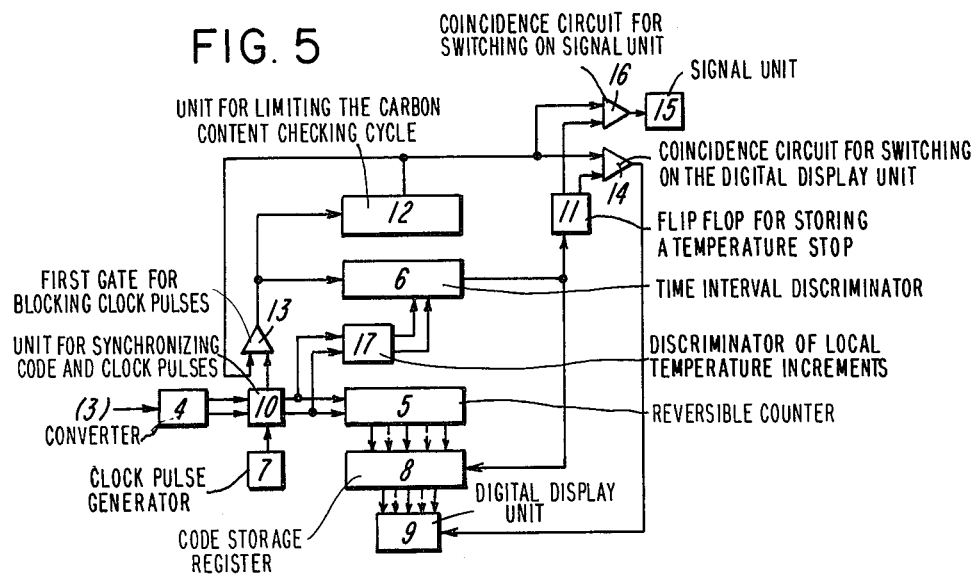
FIG. 5 is a block diagram of an alternative embodiment of the proposed device which ensures detection of non-ideal temperature stops.

During the crystallization period, temperature increments on the portion 115 (FIG. 29) of the cooling curve are not in excess of the predetermined threshold $\pm \epsilon_o$, so no pulses are formed during this period at the output of the discriminator 17 (FIG. 5). As a result, if the duration $\tau_a$ of the portion 115 (FIG. 29) is in excess of the time threshold $\tau_o$ set in the discriminator 6, said discriminator 6, as it has been described above, detects this portion of the cooling curve and sends a pulse to the control input of the register 8 and to the unit input of the flip-flop 11.

In the simplest case, the discriminator 17 may be constructed as the reversible counter 72 (FIG. 16) of local temperature increments on the cooling curve. In the initial state, the reversible counter 72 is zeroized by an initial setting key or automatically as will be shown below. Applied to the add input of said counter 72 are code pulses corresponding to a positive increment of temperature on the cooling curve. Applied to the subtract input of the counter 72 are code pulses corresponding to a negative increment of temperature on the cooling curve. In case of a certain local temperature increment on the cooling curve, there is formed an add overflow pulse or a subtract overflow pulse (depending upon the direction of the temperature increment) at the outputs of the counter 72. The overflow pulses of the counter 72 are applied to the respective outputs of the discriminator 17.

In practical work, there may arise the necessity of adjusting the value of the predetermined threshold $\pm \epsilon_o$. In such cases, it is more practicable to use the second embodiment of the discriminator 17 of local temperature increments on the cooling curve.

The operating principle of said second embodiment of the discriminator 17 of local temperature increments on the cooling curve (FIG. 17) is as follows. In the initial state, the number 0 is set in the reversible counter 73 (FIG. 17), which is done either with the aid of an initial setting key (not shown in FIG. 17) or automatically. With the aid of the switches of the switch unit 75 there is set a certain threshold $+\epsilon_o$ of non-sensitivity to positive local increments of temperature on the cooling curve. With the aid of the switches of the switch unit 76 there is set a certain threshold $-\epsilon_o$ of non-sensitivity to negative local temperature increments on the cooling curve. For example, if a predetermined threshold $+\epsilon_o$ corresponds to five code pulses, the position of the switches of the switch unit 75 must correspond to the positive number 5 (the binary code 101). Consequently, the switches of the first and third digits of the switch unit 75 must be connected to the unity outputs of the respective digits of the counter 73, whereas the rest must be connected to the zero outputs.

If a predetermined threshold $-\epsilon_o$ also corresponds to five code pulses, the position of the switches of the switch unit 76 must correspond to the negative number $-5$ (the binary code 011). Consequently, the switches of the first and second digits of the switch unit 76 must be connected to the unity outputs of the respective digits of the counter 73, whereas the rest must be connected to the zero outputs.

In the initial state, to the control inputs of the gates 79 and 80 there are applied permitting signals from the outputs of the coincidence circuits 77 and 78, respectively. Simultaneously, from the outputs of the coincidence circuits 77 and 78 there are applied inhibitory signals to the control inputs of the gates 81 and 82. As code pulses are applied to the pulse inputs of the conducting gates 79 and 80, the reversible counter 73 registers local temperature increments on the cooling curve. The coincidence circuit 77 selects the code of the reversible counter 73, corresponding to the threshold $+\epsilon_o$. The coincidence circuit 78 selects the code of the reversible counter 73, corresponding to the threshold $-\epsilon_o$. The gate 79 remains conducting until the local temperature increment reaches the positive value $+\epsilon_o$. The gate 81 remains non-conducting until the same moment, i.e. until the local temperature increment reaches the positive value $+\epsilon_o$. Similarly, the gate 80 remains conducting, and the gate 82 remains non-conducting until the local temperature increment reaches the negative value $-\epsilon_o$. As the positive number $+\epsilon_o$ is formed in the reversible counter 73 in the course of a change in temperature on the cooling curve, at the output of the coincidence circuit 77 there is formed a signal which renders the gate 79 non-conducting as regards the further count of code pulses corresponding to a positive increment of temperature on the cooling curve. This signal also snaps the output gate 81 into conduction. If after this a code pulse arrives at the pulse inputs of the gates 79 and 81, at the output of the gate 81 there is formed a signal. Said signal is applied to the respective pulse input of the discriminator 17, as well as to the initial setting input of the reversible counter 73. The inhibitory signal at the control input of the gate 79 prevents the arrival at this moment of a pulse at the add input of the reversible counter 73, which is necessary for reliable operation of the discriminator 17. The signal from the output of the gate 81 zeroes the reversible counter 73, after which the gate 79 is again driven into conduction, whereas the gate 81 is rendered non-conducting.

If in the course of a change in temperature on the cooling curve there is formed the negative number $-\epsilon_o$ in the reversible counter 73, at the output of the coincidence circuit 78 there is formed a signal which renders the gate 80 non-conducting as regards the further count of code pulses corresponding to a negative increment of temperature on the cooling curve. This signal also drives the output gate 82 into conduction. The signal formed at the output of the coincidence circuit 78 is applied to the information output of the discriminator 17. If following the formation of the negative number $-\epsilon_o$ in the counter 73, there is applied a code pulse to the pulse inputs of the gates 80 and 82, there appears a signal at the output of the gate 82. This signal is applied to the respective output of the discriminator 17 and to the second initial setting input of the reversible counter 73. The inhibitory signal at the control input of the gate 80 prevents the arrival at this moment of a pulse at the subtract input of the reversible counter 73, which is necessary for reliable operation of the discriminator 17. The signal from the output of the gate 82 zeroes the reversible counter 73, after which the gate 80 is again driven into conduction, while the gate 82 is rendered non-conducting.

Thus, signals are applied to the pulse outputs of the discriminator 17 only when following another initial setting of the reversible counter 73, the local temperature increment is in excess of the threshold $\pm\epsilon_o$ in its absolute value. If local increments of temperature on the cooling curve are not in excess of a predetermined threshold $\pm\epsilon_o$, no signals are applied to the pulse outputs of the discriminator 17.

Figure 31C:
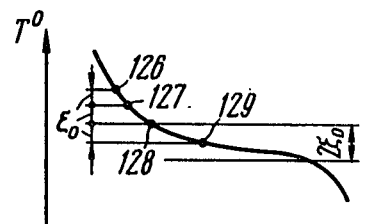
Figure 31B:
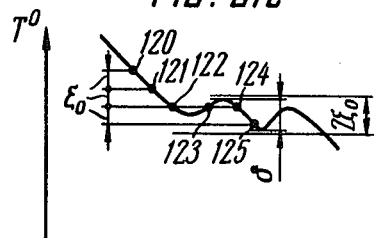
Figure 31A:
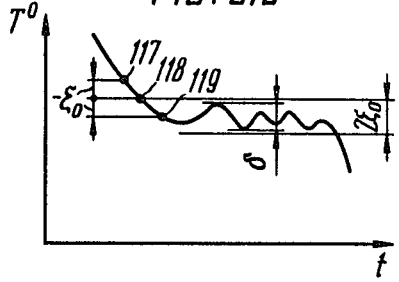

FIG. 31 shows three different types of temperature stop portions on a cooling curve to illustrate the operating principle of the second embodiment of the discriminator 17 of local temperature increments on the cooling curve. In the first case, illustrated by FIG. 31a, the greatest amplitude of temperature fluctuations on the temperature stop portion is $\delta$ and is found within a band having a width of $2\epsilon_o(\pm\epsilon_o)$. At points 117, 118 and 119 (FIG. 31a) on the cooling curve there are applied signals to the respective output of the discriminator 17 (FIG. 17), since the negative local temperature increments are in excess of the threshold $-\epsilon_o$. On the temperature stop portion, no signals are applied to the pulse outputs of the discriminator 17, since positive and negative local temperature increments are not in excess of $\pm\epsilon_o$ with respect to the temperature at the point 119. As a result, such a temperature stop is detected by the time interval discriminator 6 (FIG. 5) if the duration of this portion of the curve is in excess of the time threshold $\tau_o$ set in the discriminator 6.

FIG. 31b illustrates another case, where the greatest amplitude of temperature fluctuations on the temperature stop portion is also equal to $\delta$ and is found within the band having a width of $2\epsilon_o$. At points 120, 121 and 122 (FIG. 31b) on the cooling curve, there are applied signals to the respective pulse input of the discriminator 17 (FIG. 17). At points 123 and 124 (FIG. 31b) on the temperature stop portion, there is formed the number 0 in the reversible counter 73 (FIG. 17). At a point 125 (FIG. 31b) on the temperature stop portion, a pulse is applied to the respective pulse output of the discriminator 17 (FIG. 17), since the negative local temperature increment is in excess of the threshold $-\epsilon_o$ as regards the temperature at the point 124 (FIG. 31b). The pulse from the output of the discriminator 17 (FIG. 17) is applied to the input of the time interval discriminator 6 and sets its counter 39 (FIGS. 9, 10 and 11) in the initial state. As a result, said temperature stop is not detected by the discriminator 6 (FIG. 17) despite the fact that as in the previously discussed case, the greatest amplitude of temperature fluctuations on the temperature stop portion amounts to the same value $\delta < 2\epsilon_o$.

FIG. 31c illustrates another possible case, when a change in temperature during the crystallization period is of a monotonous nature. As in the two cases that have been described above, a change in the temperature over this portion is found within a band having a width of $2\epsilon_o$. The arrival of a signal at the respective pulse output of the discriminator 17 (FIG. 17) occurs in this case at points 126, 127 and 128 (FIG. 31c).

At a point 129 on the temperature stop portion, there is applied a signal to the respective pulse output of the discriminator 17 (FIG. 17), as the negative local temperature increment is in excess of the threshold $-\epsilon_o$ with respect to the temperature at the point 128 (FIG. 31c). As a result, no temperature stop is detected on the cooling curve, whereas the maximum change in the temperature at the temperature stop portion continues to be equal to $2\epsilon_o$.

As is seen from FIG. 31, the second embodiment of the discriminator 17 cannot detect any temperature stop on the cooling curve, if said discriminator 17 is adjusted for the threshold $\pm\epsilon_o$. To enable the discriminator 17 (FIG. 17) to detect any of the temperature stops shown in FIG. 31, said discriminator 17 must be adjusted for the threshold $\pm 2\epsilon_o$. However, in this case there is a danger of a misoperation of the time interval discriminator 6 on other portions of the cooling curve, where a temperature increment over the period of time $\tau_o$ amounts to $4\epsilon_o$, i.e. is in excess of possible temperature increments on temperature stop portions of the cooling curve.

In order to raise the reliability of detecting true temperature stops and prevent misoperation of the time interval discriminator 6, it is more practicable to register, following each arrival of a signal at any of the two code pulse inputs of the discriminator 6, negative local temperature increments with respect to the greatest local maximum on the cooling curve, and positive local temperature increments with respect to the least local minimum on the cooling curve.

This object can be attained with the use of the third embodiment of the discriminator 17 of local temperature increments, shown in FIG. 18.

The operating principle of this third embodiment of the discriminator 17 (FIG. 18) is as follows. In the initial state, the number 0 is set in the reversible counters 85 and 92, which operation is done either with the aid of an initial setting key (not shown in FIG. 18) or automatically, as will be described below. With the aid of the switches of the switch unit 86 there is set a predetermined threshold $+2\epsilon_o$ of non-sensitivity to positive local temperature increments with respect to the least local minimum of temperature on the cooling curve following an arrival of a signal at one of the pulse outputs of the discriminator 17 (FIG. 18). With the aid of the switches of the unit 93 there is set a certain threshold $-2\epsilon_o$ of non-sensitivity to negative local temperature increments with respect to the greatest local maximum of temperature on the cooling curve following an arrival of a signal at one of the pulse outputs of the discriminator 17.

In the initial state, to the control input of the gate 89 of the threshold unit 83 (FIG. 18) there is applied a permitting signal from the output of the coincidecne circuit 87; from the same output of the coincidence circuit 87 there is applied an inhibitory signal to the control input of the gate 91. In the presence of the zero number in the reversible counter 85, to the control input of the gate 90 there is applied an inhibitory signal from the output of the zero decoder 88. In the initial state, to the control input of the gate 97 of the threshold unit 84 there is applied a permitting signal from the output of the coincidence circuit 94; from the same output of the coincidence circuit 94 there is applied an inhibitory signal to the control input of the gate 98. In the presence of the zero number in the reversible counter 92, to the control input of the gate 98 there is applied an inhibitory signal from the output of the zero decoder 95.

In the course of a change in the temperature on the cooling curve, the reversible counter 85 registers positive local temperature increments with respect to the least local minimum of temperature on the cooling curve following another arrival of the signal to one of the two pulse outputs of the discriminator 17. Simultaneously, the reversible counter 92 registers negative local increments of temperature with respect to the greatest local maximum of temperature on the cooling curve following the arrival of the signal to one of the two pulse outputs of the discriminator 17. With the formation of the positive number $2\epsilon_o$ in the reversible counter 85, at the output of the coincidence circuit 87 there is formed a signal which renders the gate 89 non-conducting and drives the gate 91 into conduction. If after this a code pulse is applied to the pulse inputs of the gates 89 and 91, there appears a signal at the output of the gate 91. Said signal is applied to the respective pulse output of the discriminator 17, as well as to the initial setting input of the reversible counter 85. The reversible counter 85 is then zeroed, after which the gate 89 is again driven into conduction, whereas the gates 90 and 91 are rendered non-conducting.

With the formation of the negative number $-2\epsilon_o$ in the reversible counter 92, at the output of the coincidence circuit 94 there is formed a signal which renders the gate 97 non-conducting with regard to further count of code pulses corresponding to a negative increment of temperature on the cooling curve; this signal also drives the gate 98 into conduction. The same signal is applied to the information output of the discriminator 17. If following the formation in the reversible counter 92 of the negative number $-2\epsilon_o$, there is applied a code pulse to the pulse inputs of the gates 97 and 98, there appears a signal at the output of the gate 98. Said signal is applied to the respective pulse output of the discriminator 17 and to the initial setting input of the reversible counter 92. The reversible counter 92 is then zeroed, after which the gate 97 is again driven into conduction, whereas the gates 96 and 98 are rendered non-conducting.

The operating principle of the third embodiment of the discriminator 17 of local temperature increments on the cooling curve (FIG. 18) is illustrated by FIG. 32 which shows a temperature stop portion of a cooling curve with an indication of characteristic points thereon. Let it be assumed that at a point 130 there is applied a signal to the respective pulse output of the discriminator 17 (FIG. 18). After this, code pulses start arriving at the subtract input of the reversible counter 92 via the conducting gate 97. As this takes place, the reversible counter 92 registers negative local temperature increments with respect to the temperature at the point 130 (FIG. 32), which point 130 is the point of the greatest local maximum on the cooling curve portion following the arrival of the last signal at the pulse output of the discriminator 17 (FIG. 18). At the portion of the cooling curve between the point 130 (FIG. 32) and a point 131, which is the point of the least local minimum of the cooling curve portion following the arrival of the last signal to the pulse output of the discriminator 17 (FIG. 18), an inhibitory signal from the output of the zero decoder 88 blocks the passage of code pulses via the gate 90 to the subtract input of the reversible counter 85; the number zero thus remains in said counter 85. On the portion of the cooling curve between points 131 and 132 (FIG. 32), code pulses are applied via the conducting gate 89 (FIG. 18) to the add input of the reversible counter 85, and via the conducting gate 96 to the add input of the reversible counter 92.

As this takes place, the reversible counter 85 registers positive local temperature increments with respect to the temperature at the point 131 (FIG. 32); the reversible counter 93 (FIG. 18) registers negative local temperature increments with respect to the temperature at the point 130 (FIG. 32). On the portion of the cooling curve between a point 132, which is the local maximum point, and a point 133, code pulses are applied via the conducting gate 90 (FIG. 18) to the subtract input of the reversible counter 85 and via the conducting gate 97 to the subtract input of the reversible counter 92. At the point 133 (FIG. 32), the zero number is set in the reversible counter 85 (FIG. 18), after which an inhibitory signal is applied from the output of the zero decoder 88 to the control input of the gate 90. On the curve portion between points 133 and 134 (FIG. 32), the inhibitory signal from the output of the zero decoder 88 (FIG. 18) blocks the passage of code pulses via the gate 90 to the subtract input of the reversible counter 85, so the number zero remains in said counter 85. At the same time, code pulse continue to arrive via the conducting gate 97 to the subtract input of the reversible counter 92. At the point 134 (FIG. 32), a negative number corresponding to the threshold $-2\epsilon_o$ is formed in the reversible counter 92 (FIG. 18). As this takes place, a signal is formed at the output of the coincidence circuit 94, which renders the gate 97 non-conducting and snaps the gate 98 into conduction. While crossing the point 134 (FIG. 32) at a moment of the arrival of the next code pulse corresponding to a negative increment of temperature on the cooling curve, a signal is formed at the output of the gate 98 (FIG. 18). Said signal is applied to the respective pulse output of the discriminator 17 and at the same time zeroes the reversible counter 92. After this, the gate 97 is again driven into conduction, whereas the gate 98 is rendered non-conducting. On the portion of the cooling curve between the points 134 and 135 (FIG. 32), code pulses are applied to the subtract input of the reversible counter 92 (FIG. 18) via the conducting gate 97. As this takes place, the reversible counter 92 registers negative local increments of temperature with respect to the temperature at the point 134 (FIG. 32) which is the point of the greatest local maximum on the cooling curve portion following the arrival of a signal at the respective pulse output of the discriminator 17 (FIG. 18). At the same time, on the given portion of the cooling curve, the inhibitory signal from the output of the zero decoder 88 blocks the arrival of code pulses via the gate 90 at the subtract input of the reversible counter 85, so the number zero remains in this counter 85.

A point 135 (FIG. 32) is another point of the least local minimum on the cooling curve portion following the arrival of the last signal to the respective pulse output of the discriminator 17 (FIG. 18). On the cooling curve portion between the point 135 (FIG. 32) and a point 136, code pulses are applied via the conducting gate 89 (FIG. 18) to the add input of the reversible counter 85 and via the conducting gate 96 to the add input of the reversible counter 92. At the point 136 (FIG. 32), in the reversible counter 92 (FIG. 18) there is formed the number zero, after which an inhibitory signal is applied from the output of the zero decoder 95 to the control input of the gate 96. On the portion of the cooling curve between the points 136 and 137 (FIG. 32), the inhibitory signal from the output of the zero decoder 95 (FIG. 18) blocks the passage of code pulses via the gate 96 to the add input of the reversible counter 92, so the number zero remains in said counter 92. At the same time, on the cooling curve portion between the points 136 and 137 (FIG. 32), the reversible counter 85 (FIG. 18) continues to register positive local increments of temperature with respect to the temperature at the point 135 (FIG. 32). The point 137 (FIG. 32) on the cooling curve is the point of another greatest local maximum on the cooling curve portion following the arrival of the last signal at the respective pulse output of the discriminator 17 (FIG. 18). On the portion of the cooling curve between the points 137 and 138 (FIG. 32), code pulses are applied via the conducting gate 90 to the subtract input of the reversible counter 85 and via the conducting gate 97 to the subtract input of the reversible counter 92.

As this takes place, the reversible counter 85 registers positive local increments of temperature with respect to the temperature at the point 135 (FIG. 32), whereas the reversible counter 92 (FIG. 18) registers negative local increments of temperature with respect to the temperature at the point 137 (FIG. 32). At a point 138 on the cooling curve, the number zero is formed in the reversible counter 85 (FIG. 18), after which an inhibitory signal is applied from the output of the zero decoder 88 to the control input of the gate 90. On the portion of the cooling curve between the points 138 and 139 (FIG. 32), the inhibitory signal from the output of the zero decoder 88 (FIG. 18) blocks the passage of code pulses via the gate 90 to the subtract input of the reversible counter 85, so the number zero remains in said counter 85. At the same time, the reversible counter 92 continues to register negative local increments of temperature with respect to the temperature at the point 137 (FIG. 32). The point 139 is the point of another least local minimum on the cooling curve portion following the arrival of the last signal at the respective pulse output of the discriminator 17 (FIG. 18). On the portion of the cooling curve between the points 139 (FIG. 32) and 140, which latter point is the local maximum point, code pulses are applied via the conducting gate 89 (FIG. 18) to the add input of the reversible counter 85 and via the conducting gate 96 to the add input of the reversible counter 92. On the portion of the cooling curve between the point 140 (FIG. 32) and a point 141, which latter point is the local minimum point, code pulses are applied via the conducting gate 90 (FIG. 18) to the subtract input of the reversible counter 85 and via the conducting gate 97 to the subtract input of the reversible counter 92. On the portion of the cooling curve between the points 141 and 142 (FIG. 32) code pulses are applied via the conducting gate 89 (FIG. 18) to the add input of the reversible counter 85 and via the conducting gate 96 to the add input of the reversible counter 92. As this takes place, on all the portions of the cooling curve between the point 139 (FIG. 32) and the point 141, the reversible counter 85 (FIG. 18) registers positive local increments of temperature with respect to the temperature at the point 139 (FIG. 32), whereas the reversible counter 92 (FIG. 18) still continues to register negative local increments of temperature with respect to the temperature at the point 137 (FIG. 32). At the point 142 on the cooling curve, the reversible counter 92 (FIG. 18) is zeroed, after which an inhibitory signal is applied from the output of the zero decoder 95 to the control input of the gate 96. On the portion of the cooling curve between the points 142 and 143 (FIG. 32), the inhibitory signal from the output of the zero decoder 95 (FIG. 18) blocks the arrival of code pulses via the gate 96 at the add input of the reversible counter 92. At the same time, the reversible counter 85 continues to register positive local increments of temperature with respect to the temperature at the point 139 (FIG. 32). The point 143 is the point of another greatest local maximum on the portion of the cooling curve following the arrival of the signal at the respective pulse output of the discriminator 17 (FIG. 18). On the portion of the cooling curve between the point 143 (FIG. 32) and a point 144, which is the point of the local minimum, code pulse are applied via the conducting gate 90 (FIG. 18) to the subtract input of the reversible counter 85 and via the conducting gate 97 to the subtract input of the reversible counter 92. On the portion of the cooling curve between the point 144 (FIG. 32) and a point 145, which is the local maximum point, code pulses are applied via the conducting gate 89 (FIG. 18) to the add input of the reversible counter 85 and via the conducting gate 96 to the add input of the reversible counter 92. On the portion of the cooling curve between the points 145 and 146 (FIG. 32), code pulses are applied via the conducting gate 90 (FIG. 18) to the subtract input of the reversible counter 85 and via the conducting gate 97 to the subtract input of the reversible counter 92. As this takes place, the reversible counter 85 still continues to register positive local increments of temperature with respect to the temperature at the point 139 (FIG. 32), whereas the reversible counter 92 (FIG. 18) registers negative local increments of temperature with respect to the temperature at the point 143 (FIG. 32). At the point 146, the number zero is set in the reversible counter 85 (FIG. 18), after which an inhibitory signal is applied from the output of the zero decoder 88 to the control input of the gate 90. On the portion of the cooling curve between the points 146 and 147 (FIG. 32), the inhibitory signal from the output of the zero decoder 88 (FIG. 18) blocks the passage of code pulses via the gate 90 to the subtract input of the reversible counter 85, so the number zero remains in this counter 85. At the same time, the reversible counter 92 continues to register negative local increments of temperature with respect to the temperature at the point of the greatest local maximum (the point 143 of FIG. 32). At the point 147 on the cooling curve, a negative number corresponding to the threshold $-2\epsilon_o$ appears in the reversible counter 92 (FIG. 18). As this takes place, a signal is formed at the output of the coincidence circuit 94, which signal renders the gate 97 non-conducting and drives the gate 98 into conduction. While crossing the point 147 (FIG. 32), at the moment of the arrival of the next code pulse corresponding to a negative increment of temperature on the cooling curve, there appears a signal at the output of the gate 98 (FIG. 18). Said signal is applied to the respective pulse output of the discriminator 17 and simultaneously sets the number zero in the reversible counter 92. After this, the gate 97 is again driven into conduction, whereas the gate 98 is rendered non-conducting.

It is clear from the foregoing example that the reversible counter 85 registers positive local increments of temperature with respect to the temperature at the point of the least local minimum on the portion of the cooling curve following the arrival of a signal at the respective pulse output of the discriminator 17, whereas the reversible counter 92 registers negative local increments of temperature with respect to the temperature at the point of the greatest local maximum on the portion of the cooling curve following the arrival of a signal to the respective pulse output of the discriminator 17. Thus, if on a temperature stop portion on the cooling curve the maximum amplitude of temperature fluctuations amounts to $\delta < 2\epsilon_o$ (FIGS. 31 and 32), no signals are formed at the pulse outputs of the discriminator 17, and this temperature stop is necessarily detected by the time interval discriminator 6 if the duration of said portion is in excess of the predetermined time threshold $\tau_o$.

In some cases, there may appear several temperature stops of an equal duration on a cooling curve during a carbon content checking cycle period $\tau_{max}$. For example, on the curve shown in FIG. 33, a first temperature stop 148 (FIG. 33) corresponds to the crystallization temperature $T_1$, whereas a second temperature stop 149, which is at a lower temperature level, is a false one. On the curve of FIG. 34, a first temperature stop 151 (FIG. 34) is false and corresponds to a supercooling period, whereas a second temperature stop 152, found at a higher temperature level, corresponds to the crystallization temperature $T_1$.

In order to make it possible to obtain correct results in the cases illustrated in FIGS. 33 and 34, the proposed device is provided with a coincidence circuit 18 (FIG. 6) for forming a signal of detection of the crystallization temperature, and two gates 19 and 20 for blocking the passage of code pulses to the inputs of the discriminator 17 of local temperature increments on the cooling curve.

At a moment of detecting the first temperature stop 148 (FIG. 33) and 151 (FIG. 34) on the cooling curve, a pulse from the output of the time interval discriminator 6 (FIG. 6) enters into the register 8 a code from the reversible counter 5, which code corresponds to this temperature stop. At the same time, a pulse from the output of the discriminator 6 sets the flip-flop 11 in the unity state. The permitting signal from the unity output of the flip-flop 11 is applied to one of the inputs of the coincidence circuit 18.

If following the detection of the first temperature stop, the temperature on the cooling curve decreases (FIG. 33), at the point 150 (FIG. 33) a control signal appears at the information output of the discriminator 17 (FIG. 6) of local temperature increments on the cooling curve. As this takes place, a signal of the detection of the crystallization temperature is formed at the output of the coincidence circuit 18. From the output of the coincidence circuit 18, the signal is applied to the control inputs of the gates 19 and 20. The gates 19 and 20 are rendered non-conducting, so the arrival of code pulses at the discriminator 17 is stopped. As a result, the signal at the information output of the discriminator 17 is blocked. At the same time, the signal from the output of the coincidence circuit 18 is applied to the additional control input of the gate 13. The gate 13 is rendered non-conducting, so the arrival of clock pulses at the input of the time interval discriminator 6 is stopped. This makes it possible to prevent the detection of the false temperature stop 149 (FIG. 33).

From the output of the coincidence circuit 18 (FIG. 6), the signal is also applied to the control input of the digital display unit 9. The results of the carbon content checking cycle are thus transmitted to the digital display unit 9 before the time of the carbon content checking cycle, $\tau_{max}$, has elapsed. As a result, the duration of the carbon content checking cycle is reduced.

Figure 6:
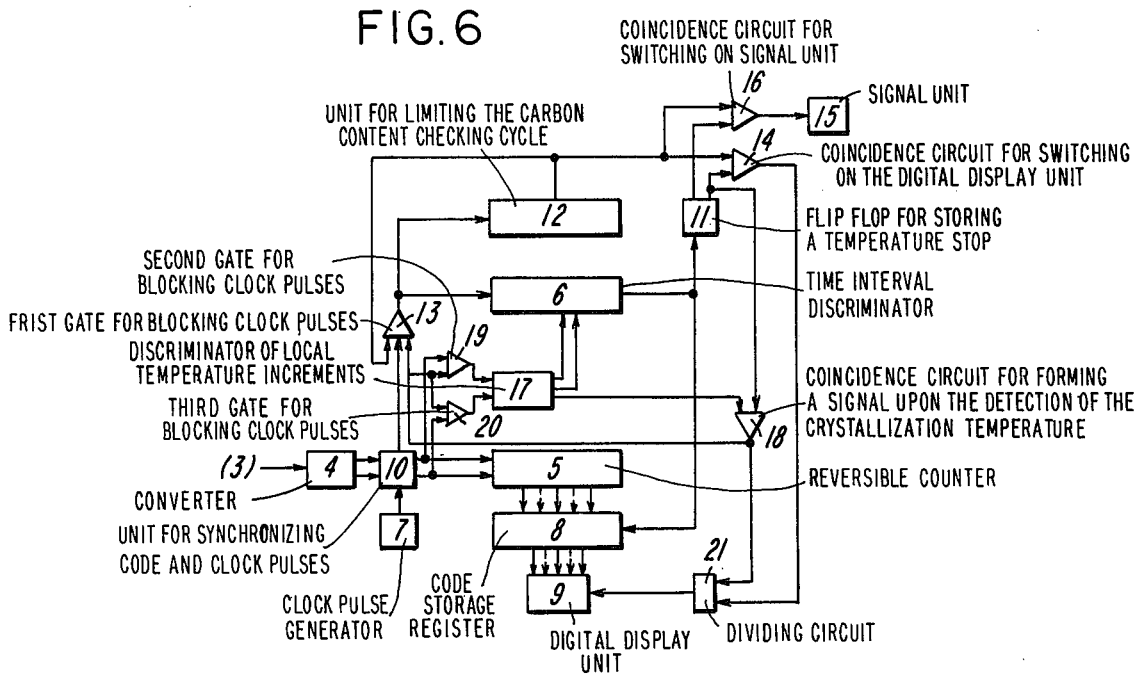
FIG. 6 is a block diagram of an alternative embodiment of the proposed device which ensures transmission of the checking results at the moment of detecting a temperature stop corresponding to the crystallization temperature and rules out detection of a false temperature stop.

If following the detection of the first temperature stop, the temperature on the cooling curve increases (FIG. 34), no signal is formed at the output of the coincidence circuit 18 (FIG. 6), as there is no signal at the information output of the discriminator 17. In this case, a new code is entered into the register 8, which code corresponds to the respective temperature stop 152 (FIG. 34). At a point 153, when the negative increment of temperature on the cooling curve after the temperature stop 152 reaches the threshold $-\epsilon_o$, there is formed a control signal at the information output of the discriminator 17 (FIG. 6). At the output of the coincidence circuit 18, there is formed a signal of the detection of the crystallization temperature, which signal renders the gates 13, 19 and 20 non-conducting and transmits the checking results to the digital display unit 9.

The transmission of checking results to the digital display unit 9 only by a signal from the output of the coincidence circuit 18 is not always convenient, because said signal may in some cases be formed after the carbon content checking period $\tau_{max}$ has elapsed. This may occure when (FIG. 35) a temperature stop 154 (FIG. 35) of a great duration is registered on the cooling curve. In this case, the signal at the output of the coincidence circuit 18 (FIG. 6) is only formed at a point 155 (FIG. 35) although the maximum time of the carbon content checking cycle, $\tau_{max}$, is ended at a point 156.

By using the circuit 21 (FIG. 6) for dividing signals from the outputs of the coincidence circuits 14 and 18, it is possible to maximally accelerate the transmission of checking results to the digital display unit 9.

For the curves shown in FIGS. 33 and 34, a signal is applied to the control input of the digital display unit 9 (FIG. 6) from the output of the coincidence circuit 18 at the point 150 (FIG. 34) and the point 153 (FIG. 34). For the curve shown in FIG. 35, the signal from the output of the coincidence circuit 14 is applied to the control input of the digital display unit 9 (FIG. 6) at the point 156 (FIG. 35).

If the relationship between the crystallization temperature $T_1$ and the carbon concentration (C%) is non-linear (FIG. 21b), information from the register 8 is transmitted to the digital display unit 9 via the functional code converter 22 which contains a required relationship.

Automatic initial setting of the units of the proposed device prior to each carbon content checking cycle is effected with the aid of the coincidence circuit 23 (FIG. 7) for selecting an initial setting code, and a gate 24 for forming initial setting pulses. Automatic initial setting is effected during the warming-up period of the temperature sensor 2 (FIG. 1), at a moment of time $t_o$ (FIG. 35), when the temperature on the cooling curve has reached a certain value $T_o$ (the point 157 of FIG. 35). As soon as there is formed a code in the reversible counter 5 (FIG. 7), corresponding to the temperature $T_o$, at the output of the coincidence circuit 23 there is formed a permitting signal which is applied to the control input of the gate 24. The gate 24 is driven into conduction. Fron the output of the converter 4, a code pulse corresponding to the positive increment of temperature on the cooling curve passes via the conducting gate 24 and is applied to the initial setting inputs of the time interval discriminator 6, the unit 12 for limiting the carbon content checking cycle, the discriminator 17 of local temperature increments on the cooling curve, and the flip-flop 11 of a temperature stop on the cooling curve. As this takes place, the flip-flop 11 is set to zero. The counter 39 (FIGS. 9, 10 and 11) and the flip-flop 45 (FIG. 11) of the time interval discriminator 6 are set to zero. The counter 24 (FIGS. 14 and 15) of the unit 12 for limiting the carbon content checking cycle is set to zero. The counter 72 (FIG. 16), or the counter 73 (FIG. 17), or the counters 85 and 92 (FIG. 18) of the discriminator 17 of local temperature increments on the cooling curve are set to zero.

After the carbon content checking cycle is over, and when at the point 158 (FIG. 35) the temperature on the cooling curve is again equal to $T_o$, no pulse is formed at the output of the gate 24 (FIG. 7), because code pulses applied to the output of the converter 4 correspond to a negative increment of temperature on the cooling curve. Hence, there is no automatic setting of the device at the end of the carbon content checking cycle, which is necessary to preserve the checking results until the start of another checking cycle.

The proposed digital device for automatically checking the carbon content in metal with reference to temperature stops on a cooling curve ensures the detection of temperature stops irrespective of all kinds of disturbances due to a change in the nature of the cooling curve.

The device is capable of effectively distinguishing between temperature stops corresponding to the crystallization temperature and false temperature stops. The device is capable of detecting a non-ideal temperature stop, during which slight temperature fluctuations are observed.

The absence of time quantization of a metal temperature signal accounts for high efficiency of the device.

The employment of simple computer units in the device ensures its high reliability, as well as low cost and small dimensions. The device can operate without any maintenance over long periods of time.

The use of the device according to the present invention rules out subjective errors which are liable to occur in visually reading out data from a plotting tape of a recording device. It makes it possible to reduce the carbon content checking cycle and fully automate the checking of carbon content in metals with reference to the crystallization temperature.

Taken in combination with any conventional measuring device for checking the carbon content in metal with reference to the crystallization temperature, the proposed device may perform the function of a carbon content digit transducer in a closed-loop control system for controlling steel smelting processes with the use of a computer.

What is claimed is:

1. A digital device, for automatically checking the carbon content in a metal with reference to temperature stops in a cooling curve, comprising:
   a converter, which converts the actual temperature of the metal into a numerical pulse code, having an input whereto there is applied a signal carrying information on the temperature of the metal, a first output of code pulses corresponding to a positive increment of temperature on the cooling curve, and a second output of code pulses corresponding to a negative increment of temperature on the cooling curve;
   a reversible counter, for converting the numerical pulse code into a parallel code, having an add input, a subtract input, and digit outputs, said reversible counter being electrically connected through its add input and subtract input to the first and second code pulse outputs of said converter;
   a time interval discriminator having a first input of code pulses corresponding to a positive increment of temperature on the cooling curve, a second input of code pulses corresponding to a negative increment of temperature on the cooling curve, a clock pulse input, and an output, said time interval discriminator being electrically connected through its first and second inputs to the first and second outputs of said converter;

a clock pulse generator having a clock pulse output and being electrically connected through its output to the clock pulse input of said time interval discriminator;

a code storage register, for storing codes corresponding to temperature stops on the cooling curve, having a information inputs, a control input, and digit outputs, said code storage register being electrically connected through its information inputs to digit outputs of said reversible counter, and being electrically connected through its control input to the output of said time interval discriminator; and a digital display unit having information inputs and being electrically connected through its information inputs to the digit outputs of said register.

2. A device as claimed in claim 1, comprising:

a unit for synchronizing code and clock pulses having a first input of code pulses corresponding to a positive increment of temperature on the cooling curve, a second input of code pulses corresponding to a negative increment of temperature on the cooling curve, a clock pulse input, a first output of synchronized code pulses corresponding to a positive increment of temperature on the cooling curve, a second output of synchronized code pulses corresponding to a negative increment of temperature on the cooling curve, and an output of synchronized clock pulses, said unit for synchronizing code and clock pulses being connected through its first and second inputs to the first and second outputs of said converter, through its clock pulse input to the output of the clock pulse generator, and through its first and second outputs to the add input and the subtract input of said reversible counter, said unit for sychronizing code and clock pulses also being electrically connected through its first and second outputs to the first and second inputs of said time interval discriminator, and through its third output to the clock pulse input of said time interval discriminator.

3. A device as claimed in claim 1, comprising:

said digital display unit having a control input;

a flip-flop, for storing a temperature stop on the cooling curve, having a first input, a first output and a second output and being electrically connected through its first input to the output of said time interval discriminator, and being electrically connected through one of its outputs to a control input of said digital display unit.

4. A device as claimed in claim 1, comprising:

a gate for blocking the passage of clock pulses having a pulse input and an output and being electrically connected through its pulse input to the output of said clock pulse generator, and through its output to the clock pulse input of said time interval discriminator; and a unit for limiting the carbon content checking cycle having a first input and an output whereto there is applied a signal as to the end of the carbon content checking cycle, said unit for limiting the carbon content checking cycle being connected through its input to the output of said gate for blocking the passage of clock pulses, and through its output to a control input of said gate for blocking the passage of clock pulses.

5. A device as claimed in claim 2, comprising:

a gate for blocking the passage of clock pulses having a pulse input and an output and being electrically connected through its pulse input to the output of synchronized clock pulses of said unit for synchronizing code and clock pulses, said gate for blocking the passage of clock pulses being electrically connected through its output to the clock pulse input of said time interval discriminators; and a unit for limiting the carbon content checking cycle having an input and an output, whereto there is applied to a signal as to the end of the carbon content checking cycle, and being connected through its input to the output of said gate for blocking the passage of clock pulses and through its output to a control input of said gate for blocking the passage of clock pulses.

6. A digital device, for automatically checking the carbon content in a metal with reference to temperature stops on a cooling curve, comprising:

a converter, which converts the actual temperature of the metal into a numerical pulse code, having an input whereto there is applied a signal carrying information on the temperature of the metal, a first output of code pulses corresponding to a positive increment of temperature on the cooling curve, and a second output of code pulses corresponding to a negative increment of temperature on the cooling curve;

a reversible counter, for converting the numerical pulse code into a parallel code, having an add input, a subtract input, and digit outputs, said reversible counter being electrically connected through its add input and subtract input to the first and second outputs of said converter;

a time interval discriminator having a first input of code pulses corresponding to a positive increment of temperature on the cooling curve, a second input of code pulses correponding to a negative increment of temperature on the cooling curve, a clock pulse input and an output, said time interval discriminator being electrically connected through its first and second inputs to the first and second outputs of said converter;

a clock pulse generator having a clock pulse output and being electrically connected through its clock pulse output to the clock pulse input of said time interval discriminator;

a code storage register, for storing codes corresponding to temperature stops on the cooling curve, having information inputs, a control input, and digit outputs, said code storage register being electrically connected through its information inputs to the digit outputs of said reversible counter, and through its control input to the output of said time interval discriminator;

a digital display unit having a control input and information inputs and being electrically connected through its information inputs to the digit outputs of said register;

a flip-flop for storing a temperature stop on the cooling curve having an input and an output and being electrically connected through its input to the output of said time interval discriminator, and through its output to the control input of said digital display unit;

a first gate for blocking the passage of clock pulses having a pulse input and an output and being electrically connected through its pulse input to the output of said clock pulse generator, and through its output to the clock pulse input of said time interval discriminators;

a unit for limiting the carbon content checking cycle having an input and an output whereto there is applied a signal as to the end of the carbon content checking cycle, said unit for limiting the carbon content checking cycle being connected through its input to the output of said gate for blocking the passage of clock pulses, and through its output to a control input of said gate for blocking the passage of clock pulses; and a coincidence circuit for switching on the digital display unit having a first input, a second input, and an output, said coincidence circuit for switching on the digital display unit being connected through its first and second inputs to the output of said flip-flop for storing a temperature stop on the cooling curve and to the output of said unit for limiting the carbon content checking cycle, said first coincidence circuit being electrically connected through its output to the control input of said digital display unit.

7. A device as claimed in claim 6, comprising:

a unit for synchronizing code and clock pulses having a first input of code pulses corresponding to a positive increment of temperature on the cooling curve, a second input of code pulses corresponding to a negative increment of temperature on the cooling curve, a clock pulse input, a first output of synchronized code pulses corresponding to a positive increment of temperature on the cooling curve, a second output of synchronized code pulses corresponding to a negative increment of temperature on the cooling curve, and an output of synchronized clock pulses, said unit for synchronizing code and clock pulses being connected through its first and second inputs to the first and second outputs of said converter, through its clock pulse input to the output of said clock pulse generator, through its first and second outputs to the add input and subtract input of said reversible counter, said unit for synchronizing code and clock pulses being electrically connected through its first and second outputs to the first and second inputs of said time interval discriminator, and through its output of synchronized clock pulses to the pulse input of said first gate for blocking the passage of clock pulses.

8. A device as claimed in claim 6, comprising:
a signal unit, for initiating a signal to repeat the carbon content checking cycle, having an input; and
a coincidence circuit for switching on said signal unit having a first input, a second input, and an output,
said coincidence circuit for switching on said signal unit being connected through its first input to a second output of said flip-flop of a temperature stop on the cooling curve, through its second input to the output of said unit for limiting the carbon content checking cycle, and through its output to the input of said signal unit.

9. A device as claimed in claim 1, comprising:
a discriminator of local temperature increments on the cooling curve having a first input, a second input, a first pulse output whereto there are applied signals in case of a certain positive increment of temperature on the cooling curve, and a second pulse output whereto there are applied signals in case of a certain negative increment of temperature on the cooling curve, said discriminator of local temperature increments on the cooling curve being connected through its first and second inputs to the first and second outputs of said converter and through its first and second pulse outputs to the first and second inputs of said time interval discriminator.

10. A device as claimed in claim 9, comprising:
a unit for synchronizing code and clock pulses having a first input of code pulses corresponding to a positive increment of temperature on the cooling curve, a second input of code pulses corresponding to a negative increment of temperature on the cooling curve, a clock pulse input, a first output of synchronized code pulses corresponding to a positive increment of temperature on the cooling curve, a second output of synchronized code pulses correcponding to a negative increment of temperature on the cooling curve, and an output of synchronized clock pulses, said unit for synchronizing code and clock pulses being connected through its first and second inputs to the first and second outputs of said converter, through its clock pulse input to the output of the clock pulse generator, through its first and second outputs to the add input and substract input of said reversible counter, as well as to the first and second inputs of said discriminator of local temperature increments on the cooling curve, and through its output of synchronized clock pulses to the clock pulse input of said time interval discriminator.

11. A device as claimed in claim 6, comprising:
a discriminator of local temperature increments on the cooling curve having a first input, a second input, a first pulse output whereto there are applied pulses in case of a certain positive increment of temperature on the cooling curve, and a second pulse output whereto there are applied signals in case of a certain negative temperature increment on the cooling courve, said discriminator of local temperature increments on the cooling curve being connected through its first and second inputs to the first and second outputs of said converter, and through its first and second pulse outputs to the first and second inputs of said time intervall discriminator.

12. A device as claimed in claim 7, comprising: a discriminator of local temperature increments on the cooling curve having a first input, a second input, a first pulse output whereto there are applied signals in case of a certain positive increment of temperature on the cooling curve, and a second pulse output whereto there are applied signals in case of a certain negative increment of temperature on the cooling curve, said discriminator of local temperature increments on the cooling curve being connected through its first and second inputs to the first and second outputs of said unit for synchronizing code and clock pulses, and through its first and second pulse outputs to the first and second inputs of said time interval discriminator.

13. A device as claimed in claim 11, comprising:
said discriminator of local temperature increments on the cooling curve having an information output;
said first gate for blocking the passage of clock pulses, having a control input;
a second gate for blocking the passage of code pulses having a pulse input, a control input, and an output and being electrically connected through its pulse input to the first output of said converter, said second gate being connected through its output to the first input of said discriminator of local temperature increments on the cooling curve;
a third gate for blocking the passage of code pulses having a pulse input, a control input, and an output and being electrically connected through its pulse input to the second output of said converter, and through its output to the second input of said discriminator of local temperature increments on the cooling curve; and
a coincidence circuit for forming a signal upon the detection of the crystallization temperature having a first input, a second input, and an output,
said coincidence circuit for forming a signal upon the detection of the crystallization temperature being connected through its first input to the output of the flip-flop of a temperature stop on the cooling curve, through its second input to the information output of said discriminator of local temperature increments on the cooling curve, and through its output to the control input of said second gate for blocking the passage of code pulses, the control input of said third gate for blocking the passage of code pulses, and a control input of said first gate for blocking the passage of clock pulses.

14. A device as claimed in claim 13, comprising:
said coincidence circuit for forming a signal upon the detection of the crystallization temperature being electrically connected through its output to the control input of said digital display unit.

15. A device as claimed in claim 13, comprising:
a unit for synchronizing code and clock pulses having a first input of code pulses corresponding to a positive increment of temperature on the cooling curve, a second input of code pulses corresponding to a negative increment of temperature on the cooling curve, a clock pulse input, a first output of synchronized code pulses corresponding to a positive increment of temperature on the cooling curve, a second output of synchronized code pulses corresponding to a negative increment of temperature on the cooling curve, and an output of synchronized clock pulses,
said unit for synchronizing code and clock pulses being connected through its first and second inputs to the first and second outputs of said converter, through its clock pulse input to the output of said clock pulse generator, through its first and second outputs to the add input and subtract input of said reversible counter, as well as to the pulse input of said second gate for blocking the passage of code pulses and to the pulse input of said third gate for blocking the passage of code pulses and through its output of synchronized clock pulses to the pulse input of said first gate for blocking the passage of code pulses.

16. A device as claimed in claim 14, comprising:
a dividing circuit having a first input, a second input, and an output and being connected through its first input to the output of said coincidence circuit for switching on the digital display unit, through its second input to the output of said coincidence circuit for forming a signal upon the detection of the crystallization temperature, and through its output to the control input of said digital display unit.

17. A device as claimed in claim 15, comprising:
a dividing circuit having a first input, a second input, and an output, said dividing circuit being connected through its first input to the output of said coincidence circuit for switching on said digital display unit, through its second input to the output of said coincidence circuit for forming a signal upon the detection of the crystallization temperature, and through its output to the control input of said digital display unit.

18. A digital device, for automatically checking the carbon content in a metal with reference to temperature stops on a cooling curve, comprising:
a converter, which converts the actual temperature of the metal into a numerical pulse code, having an input whereto there is applied a signal carrying information on the temperature of the metal, a first output of code pulses corresponding to a positive increment of temperature on the cooling curve, and a second output of code pulses corresponding to a negative increment of temperature on the cooling curve;
a reversible counter, for converting the numerical pulse code into a parallel code, having an add input, a subtract input, and digit outputs,
said reversible counter being electrically connected through its add input and subtract input to the first and second outputs of said converter;
a time interval discriminator having a first input of code pulses corresponding to a positive increment of temperature on the cooling curve, a second input of code pulses corresponding to a negative increment of temperature on the cooling curve, a clock pulse input, and an output,
said time interval discriminator being electrically connected through its first and second inputs to the first and second outputs of said converter;
a clock pulse generator having a clock pulse output and being electrically connected through its clock pulse output to the clock pulse input of said time interval discriminator;
a code storage register, for storing codes corresponding to temperature stops on the cooling curve, having information inputs, a control input, and digit outputs,
said code storage register being electrically connected through its information inputs to the digit outputs of said reversible counter, and through its control input to the output of said time interval discriminator;
a functional code converter, for converting a code corresponding to a temperature stop on the cooling curve into a code corresponding to the carbon concentration in the metal, having inputs and outputs and being connected through its inputs to the digit outputs of said code storage register; and a digital display unit having information inputs and being connected through its information inputs to the outputs of said functional code converter.

19. A device as claimed in claim 6, comprising:
a functional code converter, for converting a code corresponding to a temperature stop on the cooling curve into a code corresponding to the carbon concentration in the metal, having inputs and outputs and being connected through its inputs to the digit outputs of said code storage register, and through its outputs to the information inputs of said digital display unit.

20. A device as claimed in claim 9, comprising:
a functional code converter, for converting a code corresponding to a temperature stop on the cooling curve into a code corresponding to the carbon concentration in the metal, having inputs and outputs and being connected through its inputs to the digit outputs of said code storage register, and through its outputs to the information inputs of said digital display unit.

21. A device as claimed in claim 11, comprising:
a functional code converter, for converting a code corresponding to a temperature stop on the cooling curve into a code corresponding to the carbon concentration in the metal, having inputs and outputs and being connected through its inputs to the digit outputs of said code storage register, and through its outputs to the information inputs of said digital display unit.

22. A device as claimed in claim 16, comprising:
a functional code converter, for converting a code corresponding to a temperature stop on the cooling curve into a code corresponding to the carbon concentration in the metal, having inputs and outputs and being connected through its inputs to the digit outputs of said code storage register, and through its outputs to the information inputs of said digital display unit.

23. A digital device, for automatically checking carbon concentration in a metal with reference to temperature stops on a cooling curve, comprising:
a converter, which converts the actual temperature of the metal into a numerical pulse code, having an input whereto there is applied a signal carrying information on the temperature of metal, a first output of code pulses corresponding to a positive increment of temperature on the cooling curve, and a second output of code pulses corresponding to a negative increment of temperature on the cooling curve;
a reversible counter, for converting the numerical pulse code into a parallel code, having an add input, a subtract input, and digit outputs,
said reversible counter being electrically connected through its add input and subtract input to the first and second outputs of said converter;
a time interval discriminator having a first input of code pulses corresponding to a positive increment of temperature on the cooling curve, a second input of code pulses corresponding to a negative increment of temperature on the cooling curve, a clock pulse input, an initial setting input, and an output,
said time interval discriminator being electrically connected through its first and second inputs to the first and second outputs of said converter;
a clock pulse generator having a clock pulse output and being electrically connected through its clock pulse output to the clock pulse input of said time interval discriminator;
a code storage register, for storing codes corresponding to temperature stops on the cooling curve, having information inputs, a control input, and digit outputs,
said code storage register being electrically connected through its information inputs to the digit outputs of said reversible counter, and through its control input to the output of said time interval discriminator;
a digital display unit having information inputs and being electrically connected through its information inputs to the digit outputs of said register;
a coincidence circuit for selecting an initial setting code having inputs and an output and being connected through its inputs to the digit outputs of said reversible counter; and
a gate for forming an initial setting pulse having a control input, a pulse input, and an output,
said gate for forming an initial setting pulse being connected through its control input to the output of said coincidence circuit for selecting an initial setting code, through its pulse input to the first output of said converter, and through its output to the initial setting input of said time interval discriminator.

24. A device as claimed in claim 3, comprising:
said flip-flop for storing a temperature stop on the cooling curve having an initial setting input;
a coincidence circuit for selecting an initial setting code having inputs and an output and being connected through its inputs to the digit outputs of said reversible counter;
a gate for forming an initial setting pulse having a control input, a pulse input, and an output,
said gate for forming an initial setting pulse being connected through its control input to the output of said coincidence circuit for selecting an initial setting code, through its pulse input to the first output of said converter, and through its output to the initial setting input of said flip-flop for storing a temperature stop on the cooling curve.

25. A device as claimed in claim 4, comprising:
said unit for limiting the carbon content checking cycle having an initial setting input;
a coincidence circuit for selecting an initial setting code having inputs and an output and being connected through its inputs to the digit outputs of said reversible counter; and
a gate for forming an initial setting pulse having a control input, a pulse input, and an output,
said gate for forming an initial setting pulse being connected through its control input to the output of said coincidence circuit for selecting an initial setting code, though its pulse input to the first output of said converter; and through its output to the initial setting input of said unit for limiting the carbon content checking cycle.

26. A device as claimed in claim 9, comprising:
said discriminator of local temperature increments on the cooling curve having an initial setting input;
a coincidence circuit for selecting an initial setting code having inputs and an output and being connected through its inputs to the digit outputs of said reversible counter; and a gate for forming an initial setting pulse having a control input, a pulse input, and an output, said gate for forming an initial setting pulse being connected through its control input to the output of said coincidence circuit for selecting an initial setting code, through its pulse input to the first output of said converter, and through its output to the initial setting input of said discriminator of local temperature increments on the cooling curve.

27. A digital device, for automatically checking the carbon content of a metal with reference to temperature stops on a cooling curve, comprising:

a converter, which converts the actual temperature of the metal into a numerical pulse code, having an input whereto there is applied a signal carrying information on the temperature of the metal, a first output of code pulses corresponding to a positive increment of temperature on the cooling curve, and a second output of code pulses corresponding to a negative increment of temperature on the cooling curve;

a reversible counter, for converting the numerical pulse code into a parallel code, having an add input, a subtract input, and digit outputs, said reversible counter being electrically connected through its add input and subtract input to the first and second outputs of said converter;

a time interval discriminator having a first input of code pulses corresponding to a positive increment of temperature on the cooling curve, a second input of code pulses corresponding to a negative increment of temperature on the cooling curve, a clock pulse input, and an output, said time interval discriminator being electrically connected through its first and second inputs to the first and second outputs of said converter;

a time interval counter of said time interval discriminator having a first initial setting input which is the first input of code pulses corresponding to a positive increment of temperature on the cooling curve of said time interval discriminator, a second initial setting input which is the second input of code pulses corresponding to a negative increment of temperature on the cooling curve of said time interval discriminator, a counting input which is the clock pulse input of said time interval discriminator, and an overflow output which is the output of said time interval discriminator whereto there is applied a pulse at a moment of detecting a temperature stop on the cooling curve;

a clock pulse generator having a clock pulse output and being electrically connected through its clock pulse output to the clock pulse input of said time interval discriminator;

a code storage register, for storing codes corresponding to temperature stops on the cooling curve, having information inputs, a control input, and digit outputs, said code storage register being electrically connected through its information inputs to the digit outputs of said reversible counter, and through its control input to the output of said time interval discriminator; and a digital display unit having information inputs and being electrically connected through its information inputs to the digit outputs of said register.

28. A device as claimed in claim 6, wherein said time interval discriminator comprises:

a time interval counter having a first initial setting input which is the first input of code pulses corresponding to a positive increment of temperature on the cooling curve of said time interval discriminator, a second initial setting input which is the second input of code pulses corresponding to a negative increment of temperature on the cooling curve of said time interval discriminator, a counting input which is the clock pulse input of said time interval discriminator, and an overflow output which is the output of said time interval discriminator whereto there is applied a pulse at a moment of detecting a temperature stop on the cooling curve.

29. A device as claimed in claim 11, wherein said time interval discriminator comprises:

a time interval counter having a first initial setting input which is the first input of code pulses corresponding to a positive increment of temperature in the cooling curve of said time interval discriminator, a second initial setting input which is the second input of code pulses corresponding to a negative increment of temperature on the cooling curve of said time interval discriminator, a counting input which is the clock pulse input of said time interval discriminator, and an overflow output which is the output of said time interval discriminator whereto there is applied a pulse at a moment of detecting a temperature stop on the cooling curve.

30. A device as claimed in claim 18, wherein said time interval discriminator comprises:

a time interval counter having a first initial setting input which is the first input of code pulses corresponding to a positive increment of temperature on the cooling curve of said time interval discriminator, a second initial setting input which is the second input of code pulses corresponding to a negative increment of temperature of said time interval discriminator, a counting input which is the clock pulse input of said time interval discriminator, and an overflow output which is the output of said time interval discriminator whereto there is applied a pulse at a moment of detecting a temperature stop on the cooling curve.

31. A device as claimed in claim 23, wherein said time interval discriminator comprises:

a time interval counter having a first initial setting input which is the first input of code pulses corresponding to a positive increment of temperature on the cooling curve of said time interval discriminator, a second initial setting input which is the second input of code pulses corresponding to a negative increment of temperature on the cooling curve of said time interval discriminator, a counting input which is the clock pulse input of said time interval discriminator, a third initial setting input which is the initial setting input of said time interval discriminator, and an overflow output which is the output of said time interval discriminator whereto there is applied a pulse at a moment of detecting a temperature stop on the cooling curve.

32. A digital device, for automatically checking the carbon content in a metal with reference to temperature stops on a cooling curve, comprising:

a converter, which converts the actual temperature of the metal into a numerical pulse code, having an input whereto there is applied a signal carrying information on the temperature of metal, a first output of code pulses corresponding to a positive increment of temperature on the cooling curve, and a second output of code pulses corresponding to a negative increment of temperature on the cooling curve;

a reversible counter, for converting the numerical pulse code into a parallel code, having an add input, a subtract input, and digit outputs, said reversible counter being electrically connected through its add input and subtract input to the first and second outputs of said converter;

a time interval discriminator having a first input of code pulses corresponding to a positive increment of temperature on the cooling curve, a second input of code pulses corresponding to a negative increment of temperature on the cooling curve, a clock pulse input, and an output, said time interval discriminator being electrically connected through its first and second inputs to the first and second outputs of said converter;

a counter of time intervals of said time interval discriminator having a first initial setting input which is the first input of code pulses corresponding to a positive increment of temperature on the cooling curve of said time interval discriminator, a second initial setting input which is the second input of code pulses corresponding to a negative increment of temperature on the cooling curve of said time interval discriminator, a counting input which is the clock pulse input of said time interval discriminator, and digit outputs;

a first switch unit of said time interval discriminator having inputs and outputs;

a first coincidence circuit of said time interval discriminator having a pulse input, potential inputs, and an output which is the output of the time interval discriminator, said first coincidence circuit being connected through its potential inputs via the first switch unit to the digit outputs of said time interval counter, and through its pulse inputs to the counting input of said time interval counter;

a clock pulse generator having a clock pulse output and being electrically connected through its clock pulse output to the clock pulse input of said time interval discriminator;

a code storage register, for storing codes coresponding to temperature stops on the cooling curve, having information inputs, a control input, and digit outputs, said code storage register being electrically connected through its information inputs to the digit outputs of said reversible counter, and through its control input to the output of said time interval discriminator; and a digital display unit having information inputs and being electrically connected through its information inputs to the digit outputs of said register.

33. A device as claimed in claim 6, wherein said time interval discriminator comprises:

a time interval counter having a first initial setting input which is the first input of code pulses corresponding to a positive increment of temperature on the cooling curve of said time interval discriminator, a second initial setting input which is the second input of code pulses corresponding to a negative increment of temperature on the cooling curve of said time interval discriminator, a counting input which is the clock pulse input of said time interval discriminator, and digit outputs;

a first switch unit having of inputs and outputs;

a first coincidence circuit of said time interval discriminator having a pulse input, potential inputs, and an output which is the output of the time interval discriminator, said first coincidence circuit of said time interval discriminator being connected through its potential inputs via the switch unit to the digit outputs of said time interval counter, and through its pulse input to the counting input of said time interval counter.

34. A device as claimed in claim 11, wherein said time interval discriminator comprises:

a time interval counter having a first initial setting input which is the first input of code pulses corresponding to a positive increment of temperature on the cooling curve of said time interval discriminator, a second initial setting input which is the second input of code pulses corresponding to a negative increment of temperature on the cooling curve of said time interval discriminator, a counting input which is the clock pulse input of said time interval discriminator, and digit outputs;

a first switch unit having inputs and outputs;

a first coincidence circuit of said time interval discriminator having a pulse input, potential inputs, and an output which is the output of said time interval discriminator, said first coincidence circuit of said time interval discriminator being connected through its potential inputs via the switch unit to the digit outputs of said time interval counter, and through its pulse input to the counting input of said time interval counter.

35. A device as claimed in claim 18, wherein said time interval discriminator comprises:

a time interval counter having a first initial setting input which is the input of code pulses corresponding to a positive increment of temperature on the cooling curve of said time interval discriminator, a second initial setting input which is the second input of code pulses corresponding to a negative increment of temperature on the cooling curve of said time interval discriminator, a counting input which is the clock pulse input of said time interval discriminator, and digit outputs;

a first switch unit having inputs and outputs;

a first coincidence circuit having a pulse input, potential inputs, and an output which is the output of said time interval discriminator;

said first coincidence circuit being connected through its potential inputs via the switch unit to the digit outputs of said time interval counter, and through its pulse input to the counting input of said time interval counter.

36. A device as claimed in claim 23, wherein said time interval discriminator comprises:

a time interval counter having a first initial setting input which is the first input of code pulses corresponding to a positive increment of temperature on the cooling curve of said time interval discriminator, a second initial setting input which is the second input of code pulses corresponding to a negative increment of temperature on the cooling curve of said time interval discriminator, a counting input which is the clock pulse input of said time interval discriminator, a third initial setting input which is the initial setting input of said time interval discriminator, and digit outputs;

a first switch unit having inputs and outputs;

a first coincidence circuit of said time interval discriminator having a pulse input, potential inputs, and an output which is the output of said time interval discriminator; said first coincidence circuit of said time interval discriminator being connected through its potential inputs via the switch unit to the digit outputs of said time interval counter, and through its pulse input to the counting input of said time interval counter.

37. A digital device, for automatically checking the carbon content in a metal with reference to temperature stops on a cooling curve, comprising:

a converter, which converts the actual temperature of the metal into a numerical pulse code, having an input whereto there is applied a signal carrying information on the temperature of metal, a first output of code pulses corresponding to a positive increment of temperature on the cooling curve, and a second output of code pulses corresponding to a negative increment of temperature on the cooling curve;

a reversible counter, for converting the numerical pulse code into a parallel code, having a add input, a subtract input, and digit outputs, said reversible counter being electrically connected through its add input and subtract input to the first and second outputs of said converter;

a time interval discriminator having a first input of code pulses corresponding to a positive increment of temperature on the cooling curve, a second input of code pulses corresponding to a negative increment of temperature on the cooling curve, a clock pulse input, and an output, said time interval discriminator being electrically connected through its first and second inputs to the first and second outputs of said converter;

a time interval counter of said time interval discriminator having a first initial setting input which is the first input of code pulses corresponding to a positive increment of temperature on the cooling curve of said time interval discriminator, a second initial setting input which is the second input of code pulses corresponding to a negative increment of temperature on the cooling curve of said time interval discriminator, a counting input which is the clock pulse input of said time interval discriminator, and digit outputs;

a first switch unit of said time interval discriminator having inputs and outputs;

a first coincidence circuit of said time interval discriminator having a pulse input, a control input, potential inputs, and an output, said first coincidence circuit of said time interval discriminator being connected through its potential inputs via the first switch unit to the digit outputs of said time interval counter, and through its pulse input to the counting input of said time interval counter;

a second switch unit of said time interval discriminator having inputs and outputs;

a second coincidence circuit of said time interval discriminator having a pulse input, a control input, potential inputs, and an output, said second coincidence circuit being connected through its potential inputs via the second switch unit to the digit outputs of said time interval counter, and through its pulse input to the pulse input of said first coincidence circuit;

a flip-flop of an overheating portion of the cooling curve of said time interval discriminator having a first input, a first output, and a second output and being connected through its first output to the control input of said first coincidence circuit, through its second output to the control input of said second coincidence circuit, and through its first input to the second initial setting input of said time interval counter;

a dividing circuit of said time interval discriminator having a first input, a second input, and an output which is the output of said time interval discriminator, said dividing circuit being connected through its first input to the output of said first coincidence circuit, and through its second input to the output of said second coincidence circuit of said time interval discriminator;

a clock pulse generator having a clock pulse output and being electrically connected through its clock pulse output to the clock pulse input of said time interval discriminator;

a code storage register, for storing codes corresponding to temperature stops on the cooling curve, having information inputs, a control input, and digit outputs, said code storage register being electrically connected through its information inputs to the digit outputs of said reversible counter, and through its control inputs to the output of said time interval discriminator; and a digital display unit having information inputs and being electrically connected through its information inputs to the digit outputs of said register.

38. A device as claimed in claim 6, wherein said time interval discriminator comprises:

a time interval counter having a first initial setting input which is the first input of code pulses corresponding to a positive increment of temperature on the cooling curve of said time interval discriminator, a second initial setting input which is the input of code pulses corresponding to a negative increment of temperature on the cooling curve of said time interval discriminator, a counting input which is the clock pulse input of said time interval discriminator and digit outputs;

a first switch unit having inputs and outputs;

a first coincidence circuit of said time interval discriminator having a pulse input, a control input, potential inputs, and an output;

said first coincidence circuit of said time interval discriminator being connected through its potential inputs via the first switch unit to the digit outputs of said time interval counter, and through its pulse input to the counting input of said time interval counter;

a second switch unit having inputs and outputs;

a second coincidence circuit of said time interval discriminator having a pulse input, a control input, potential inputs, and an output and being connected through its potential inputs via the second switch unit to the digit outputs of said time interval counter, and through its pulse input to the pulse input of the first coincidence circuit;

a flip-flop of an overheating portion of the cooling curve having a first input, a first output, and a second output and being connected through its first output to the control input of said first coincidence circuit of said time interval discriminator, through its second output to the control input of said second coincidence circuit of said time interval discriminator, and through its first to the second initial setting input of said time interval counter; and a dividing circuit having a first input, a second input, and an output which is the output of said time interval discriminator, said dividing circuit being connected through its first input to the output of said first coincidence circuit of said time interval discriminator, and through its second input to the output of said second coincidence circuit of said time interval discriminator.

39. A device as claimed in claim 11, wherein said time interval discriminator comprises:

a time interval counter having a first initial setting input which is the first input of code pulses corresponding to a positive increment of temperature in the cooling curve of said time interval discriminator, a second initial setting input which is the second input of code pulses corresponding to a negative increment of temperature on the cooling curve of said time interval discriminator, a counting input which is the clock pulse input of said time interval discriminator, and digit outputs;

a first switch unit having inputs and outputs;

a first coincidence circuit of said time interval discriminator having a pulse input, a control input, potential inputs, and an output, said first coincidence circuit of said time interval discriminator being connected through its potential inputs via the first switch unit to the digit outputs of said time interval counter, and through its pulse input to the counting input of said time interval counter;

a second switch unit having inputs and outputs;

a second coincidence circuit of said time interval discriminator having a pulse input, a control input, potential inputs, and an output and being connected through its potential inputs via the second switch unit to the digit outputs of said time interval counter, and through its pulse input to the pulse input of said first coincidence circuit;

a flip-flop of an overheating portion of the cooling curve having a first input, a first output, and a second output and being connected through its first output to the control input of said first coincidence circuit of said time interval discriminator, through its second output to the control input of said second coincidence circuit of said time interval discriminator, and through its first to the second initial setting input of said time interval counter; and a dividing circuit having a first input, a second input, and an output which is the output of said time interval discriminator;

said dividing circuit being connected through its first input to the output of said first coincidence circuit of said time interval discriminator, and through its second input to the output of said second coincidence circuit of said time interval discriminator.

40. A device as claimed in claim 18, wherein said time interval discriminator comprises:

a time interval counter having a first initial setting input which is the first input of code pulses corresponding to a positive increment of temperature on the cooling curve of said time interval discriminator, a second initial setting input which is the second input of code pulses corresponding to a negative increment of temperature on the cooling curve of said time interval discriminator, a counting input which is the clock pulse input of said time interval discriminator, and digit outputs;

a first switch unit having inputs and outputs;

a first coincidence circuit having a pulse input, a control input, potential inputs, and an output, said first coincidence circuit being connected through its potential inputs via the first switch unit to the digit outputs of said time interval counter, and through its pulse input to the counting input of said time interval counter;

a second switch unit having inputs and outputs;

a second coincidence circuit having a pulse input, a control input, potential inputs, and an output and being connected through its potential inputs via the second switch unit to the digit outputs of said time interval counter, and through its pulse input to the pulse input of said first coincidence circuit of said time interval discriminator;

a flip-flop of an overheating portion of the cooling curve having a first input, a first output, and a second input, and being connected through its first output to the control input of said first coincidence circuit of said time interval discriminator, through its second output to the control input of said second coincidence circuit of said time interval discriminator, and through its first input to the second initial setting input of said time interval counter, and a dividing circuit having a first input, second input, and an output which is the output of said time interval discriminator, said dividing circuit being connected through its first input to the output of said first coincidence circuit of said time interval discriminator, and through its second input to the output of said second coincidence circuit of said time interval discriminator.

41. A device as claimed in claim 23, wherein said time interval discriminator comprises:

a time interval counter having a first initial setting input which is the first input of code pulses corresponding to a positive increment of temperature on the cooling curve of said time interval discriminator, a second initial setting input which is the second input of code pulses corresponding to a negative increment of temperature on the cooling curve of said time interval discriminator, a counting input which is the clock pulse input of said time interval discriminator, an initial setting input which is the initial setting input of said time interval discriminator, and digit outputs;

a first switch unit having inputs and outputs;

a first coincidence circuit of said time interval discriminator having a pulse input, a control input, potential inputs, and an output, said first coincidence circuit of said time interval discriminator being connected through its potential inputs via the first switch unit to the digit outputs of said time interval counter, and through its pulse input to the counting input of said time interval counter;

a second switch unit having inputs and outputs;

a second coincidence circuit of said time interval discriminator having a pulse input, a control input, potential inputs, and an output and being connected through its petential inputs via the second switch unit to the digit outputs of said time interval counter, and through its pulse input to the pulse input of said first coincidence circuit of said time interval discriminator;

a flip-flop of an overheating portion of the cooling curve having a first input, an initial setting input, a first output, and a second output and being connected through its first output to the control input of said first coincidence circuit of said time interval discriminator, through its second output to the control input of said second coincidence circuit of said time interval discriminator, through its first input to the second initial setting input of said time interval counter, and through its initial setting input to the initial setting input of said time interval counter;

a dividing circuit having a first input, a second input, and an output which is the output of said time interval discriminator, said dividing circuit being connected through its first input to the output of said first coincidence circuit of said time interval discriminator, and through its second input to the output of said second coincidence circuit of said time interval discriminator.

42. A device as claimed in claim 2, wherein the unit for synchronizing code and clock pulses comprises:

a clock pulse distribution sub-unit;

a clock pulse distribution flip-flop of said clock pulse distribution sub-unit having a synchronization unit, a first output, and a second output;

a gate for forming synchronized clock pulses of said clock pulse distribution sub-unit having a control input, a pulse input, and an output which is the output of synchronized clock pulses of said unit for synchronizing code and clock pulses, said gate for forming synchronized clock pulses of said clock pulse distribution sub-unit being connected through its control input to the first output of said clock pulse distribution flip-flop;

a gate for forming synchronizing clock pulses of said clock pulse distribution sub-unit having a control input, a pulse input, and an output and being connected through its control input to the second output of said clock pulse distribution flip-flop, and being connected through its pulse input to the pulse input of said gate for forming synchronized clock pulses and to the counting input of said clock pulse distribution flip-flop;

a first sub-unit for synchronizing code pulses;

a flip-flop for storing code pulses of said first sub-unit for synchronizing code pulses having a first input which is the first input of said synchronization unit, a second input, and an output;

a buffer flip-flop of said first sub-unit for synchronizing code pulses having a first input, a second input, a first output, and a second output;

a gate for forming synchronized code pulses of said first sub-unit for synchronizing code pulses having a control input, an input, and an output which is the first output of synchronized code pulses of said unit for synchronizing code and clock pulses, said gate for forming synchronized code pulses of said first sub-unit for synchronizing code pulses being connected through its control input to the first output of said buffer flip-flop of said first sub-unit for synchronizing code pulses, through its input to the output of said gate for forming synchronizing clock pulses of said clock pulse distribution sub-unit, and through its output to the second input of said flip-flop for storing code pulses of said first sub-unit for synchronizing code pulses and to the first input of said buffer flip-flop of said first sub-unit for synchronizing code pulses;

a coincidence circuit of said first sub-unit for synchronizing code pulses having a first input, a second input, a third input, and an output and being connected through its first input to the second output of said buffer flip-flop of said first sub-unit for synchronizing code pulses, through its second input to the output of said flip-flop for storing code pulses of said first sub-unit for synchronizing code pulses, through its third input to the output of said gate for forming synchronizing clock pulses of said clock pulse distribution sub-unit, and through its output to the second input of said buffer flip-flop of said first sub-unit for synchronizing code pulses;

a second sub-unit for synchronizing code pulses;

a flip-flop for storing code pulses of said second sub-unit for synchronizing code pulses having a first input which is the second input of said unit for synchronizing code and clock pulses, a second input, and an output;

a buffer flip-flop of said second sub-unit for synchronizing code pulses having a first input, a second input, a first output, and a second output;

a gate for forming synchronized code pulses of said second sub-unit for synchronizing code pulses having a control unit, an input, and an output which is the second output of synchronized code pulses of said unit for synchronizing code and clock pulses, said gate for forming synchronized code pulses of said second sub-unit for synchronizing code pulses being connected through its control input to the first output of said buffer flip-flop of said second sub-unit for synchronizing code pulses, through its input to the output of said gate for forming synchronizing clock pulses of said clock pulse distribution sub-unit, and through its output to the second input of said flip-flop for storing code pulses of said second sub-unit for synchronizing code pulses and to the first input of said buffer flip-flop of said second sub-unit for synchronizing code pulses;

a coincidence circuit of said second sub-unit for synchronizing code pulses having a first input, a second input, a third input, and an output and being connected through its first input to the second output of said buffer flip-flop of said second sub-unit for synchronizing code pulses, through its second input to the output of said flip-flop for storing code pulses of said second sub-unit for synchronizing code pulses, through its third input to the output of said gate for forming synchronizing clock pulses of said clock pulse distribution sub-unit, and through its output to the second input of said buffer flip-flop of said second sub-unit for synchronizing code pulses.

43. A device as claimed in claim 7, wherein said unit for synchronizing code and clock pulses comprises:

a clock pulse distribution sub-unit;

a clock pulse distribution flip-flop of said clock pulse distribution sub-unit having a counting input which is the clock pulse input of said unit for synchronizing code and clock pulses, a first output, and a second output;

a gate for forming synchronized clock pulses of said clock pulse distribution sub-unit having a control input, a pulse input, and an output which is the output of synchronized clock pulses of said unit for synchronizing code and clock pulses, said gate for forming synchronized clock pulses of said clock pulse distribution sub-unit being connected through its control input to the first output of said clock pulse distribution flip-flop;

a gate for forming synchronizing clock pulses of said clock pulse distribution sub-unit having a control input, a pulse input, and an output and being connected through its control input to the second output of said clock pulse distribution flip-flop, and through its pulse input to the pulse input of said gate for forming synchronized clock pulses and to the counting input of said clock pulse distribution flip-flop;

a first sub-unit for synchronizing code pulses;

a first flip-flop for storing code pulses of said first sub-unit for synchronizing code pulses having a first input which is the first input of said unit for synchronizing code and clock pulses, a second input, and an output;

a buffer flip-flop of said first sub-unit for synchronizing code pulses having a first input, a second input, a first output, and a second output;

a gate for forming synchronized code pulses of said first sub-unit for synchronizing code pulses having a control input, an input, and an output which is the first output of synchronized code pulses of said unit for synchronizing code and clock pulses, said gate for forming synchronized code pulses of said first sub-unit for synchronizing code pulses being connected through its control input to the first output of said buffer flip-flop of said first sub-unit for synchronizing code pulses, through its input to the output of said gate for forming synchronizing clock pulses of said clock pulse distribution sub-unit, and through its output to the second input of said flip-flop for storing code pulses of said first sub-unit for synchronizing code pulses and to the first input of said buffer flip-flop of said first sub-unit for synchronizing code pulses;

a coincidence circuit of said first sub-unit for synchronizing code pulses having a first input, a second input, a third input, and an output and being connected through its first input to the second output of said buffer flip-flop of said first sub-unit for synchronizing code pulses, through its second input to the output of said flip-flop for storing code pulses of said first sub-unit for synchronizing code pulses, through its third input to the output of said gate for forming synchronizing clock pulses of said clock pulse distribution sub-unit, and through its output to the second input of said buffer flip-flop of said first sub-unit for synchronizing code pulses;

a second sub-unit for synchronizing code pulses;

a flip-flop for storing code pulses of said second sub-unit for synchronizing code pulses having a first input which is the second input of said unit for synchronizing code and clock pulses, a second input, and an output;

a buffer flip-flop of said second sub-unit for synchronizing code pulses having a first input, a second input, a first output, and a second output;

a gate for forming synchronized code pulses of said second sub-unit for synchronizing code pulses having a control input, an input, and an output which is the second output of synchronized code pulses of said unit for synchronizing code and clock pulses, said gate for forming synchronized code pulses of said second sub-unit for synchronizing code pulses being connected through its control input to the first output of said buffer flip-flop of said second sub-unit for synchronizing code pulses, through its input to the output of said gate for forming synchronizing clock pulses of said clock pulse distribution sub-unit, and through its output to the second input of said flip-flop for storing code pulses of said second sub-unit for synchronizing code pulses and to the first input of said buffer flip-flop of said second sub-unit for synchronizing code pulses;

a coincidence circuit of said second sub-unit for synchronizing code pulses having a first input, a second input, a third input, and an output and being connected through its first input to the second output of said buffer flip-flop of said second sub-unit for synchronizing code pulses, through its second input to the output of said flip-flop for storing code pulses of said second sub-unit for synchronizing code pulses, through its third input to the output of said gate for forming synchronizing clock pulses of said clock pulse distribution sub-unit, and through its output to the second input of said buffer flip-flop of said second sub-unit for synchronizing code pulses.

44. A device as claimed in claim 10, wherein the unit for synchronizing code and clock pulses comprises:

a clock pulse distribution sub-unit;

a clock pulse distribution flip-flop of said clock pulse distribution sub-unit having a counting input which is the clock pulse input of said unit for synchronizing code and clock pulses, a first output, and a second output;

a gate for forming synchronized clock pulses of said clock pulse distribution sub-unit having a control input, a pulse input, and an output which is the output of synchronized clock pulses of said unit for synchronizing code and clock pulses, said gate for forming synchronized clock pulses of said clock pulse distribution sub-unit being connected through its control input to the first output of said clock pulse distribution flip-flop;

a gate for forming synchronizing clock pulses of said clock pulse distribution sub-unit having a control input, a pulse input, and an output and being connected through its control input to the second output of said clock pulse distribution flip-flop, and through its pulse input to the pulse input of said gate for forming synchronized clock pulses and to the counting input of said clock pulse distribution flip-flop;

a first sub-unit for synchronizing code pulses;

a flip-flop for storing code pulses of said first sub-unit for synchronizing code pulses having a first input which is the first code pulse input of said unit for synchronizing code and clock pulses, a second input, and an output;

a buffer flip-flop of said first sub-unit for synchronizing code pulses having a first input, a second input, a first output, and a second output;

a gate for synchronized code pulses of said first sub-unit for synchronizing code pulses having a control input, an input, and an output which is the first output of synchronized code pulses of said unit for synchronizing code and clock pulses, said gate for forming synchronized code pulses of said first sub-unit for synchronizing code pulses being connected through its control input to the first output of said buffer flip-flop of said first sub-unit for synchronizing code pulses, through its input to the output of said gate for forming synchronizing clock pulses of said clock pulse distribution sub-unit, and through its output to the second input of said gate for storing code pulses of said first sub-unit for synchronizing code pulses and to the first input of said buffer flip-flop of said first sub-unit for synchronizing code pulses;

a coincidence circuit of said first sub-unit for synchronizing code pulses having a first input, a second input, a third input, and an output and being connected through its first input to the second output of said buffer flip-flop of said first sub-unit for synchronizing code pulses, through its second input to the output of said flip-flop for storing code pulses of said first sub-unit for synchronizing code pulses, through its third input to the output of said gate for forming synchronizing clock pulses of said clock pulse distribution sub-unit and through its output to the second input of said buffer flip-flop of said first sub-unit for synchronizing code pulses;

a second sub-unit for synchronizing code pulses;

a flip-flop for storing code pulses of said second sub-unit for synchronizing code pulses having a first input which is the second code pulse input of said unit for synchronizing code and clock pulses, a second input, and an output;

a buffer flip-flop of said second sub-unit for synchronizing code pulses having a first input, a second input, a first output, and a second output;

a gate for forming synchronized code pulses of said second sub-unit for synchronizing code pulses having a control input, an input, and an output which is the second output of synchronized code pulses of said unit for synchronizing code and clock pulses, said gate for forming synchronized code pulses of said second sub-unit for synchronizing code pulses being connected through its control input to the first output of said buffer flip-flop of said second sub-unit for synchronizing code pulses, through its second input to the output of said gate for forming synchronizing clock pulses of said clock pulse distribution sub-unit and through its output to the second input of said flip-flop for storing code pulses of said second sub-unit for synchronizing code pulses and to the first input of said buffer flip-flop of said second sub-unit for synchronizing code pulses;

a coincidence circuit of said second sub-unit for synchronizing code pulses having a first input, a second input, a third input, and an output and being connected through its first input to the second output of said buffer flip-flop of said second sub-unit for synchronizing code pulses, through its second input to the output of said flip-flop for storing code pulses of said second sub-unit for synchronizing code pulses, and through its third input to the output of said gate for forming synchronizing clock pulses of said clock pulse distribution sub-unit, and through its output to the second input of said buffer flip-flop of said second sub-unit for synchronizing code pulses.

45. A device as claimed in claim 15, wherein the unit for synchronizing code and clock pulses comprises:
a clock pulse distribution sub-unit;
a clock pulse distribution flip-flop of said clock pulse distribution sub-unit having a counting input which is the clock pulse input of said unit for synchronizing code and clock pulses, a first output, and a second output;
a gate for forming synchronized clock pulses of said clock pulse distribution sub-unit having a control input, a pulse input, and an output which is the output of synchronized clock pulses of said unit for synchronizing code and clock pulses, said gate for forming synchronized clock pulses of said clock pulse distribution sub-unit being connected through its control input to the first output of said clock pulse distribution flip-flop;
a gate for forming synchronizing clock pulses of said clock pulse distribution sub-unit having a control input, a pulse input, and an output and being connected through its control input to the second output of said clock pulse distribution flip-flop, and connected through its pulse input to the pulse input of said gate for forming synchronized clock pulses and to the counting input of said clock pulse distribution flip-flop;
a first sub-unit for synchronizing code pulses;
a flip-flop for storing code pulses of said first having a first input which is the first code pulse input of said unit for synchronizing code and clock pulses, a second input, and an output;
a buffer flip-flop of said first sub-unit for synchronizing code pulses having a first input, a second input, a first output, and a second output;
a gate for forming synchronized code pulses of said first sub-unit for synchronizing code pulses, having a control input, an input, and an output which is the first output of synchronized code pulses of said unit for synchronizing code and clock pulses, said gate for forming synchronized code pulses of said first sub-unit for synchronizing code pulses being connected through its control input to the first output of said buffer flip-flop of said first sub-unit for synchronizing code pulses, through its input to the output of said gate for forming synchronizing clock pulses of said clock pulse distribution sub-unit, and through its output to the second input of said flip-flop for storing code pulses of said first sub-unit for synchronizing code pulses and to the first input of said buffer flip-flop of said first sub-unit for synchronizing code pulses;
a coincidence circuit of said first sub-unit for synchronizing code pulses having a first input, a second input, a third input, and an output and being connected through its first input to the second output of said buffer flip-flop of said first sub-unit for synchronizing code pulses, through its second input to the output of said flip-flop for storing code pulses of said first sub-unit for synchronizing code pulses, and through its third input to the output of said gate for forming synchronizing clock pulses of said clock pulse distribution sub-unit and through its output to the second input of said buffer flip-flop of said first sub-unit for synchronizing code pulses;
a second sub-unit for synchronizing code pulses;
a flip-flop for storing code pulses of said second sub-unit for synchronizing code pulses having a first input which is the second code pulse input of said unit for synchronizing code and clock pulses, a second input, and an output;

a buffer flip-flop of said second sub-unit for synchronizing code pulses having a first input, a second input, a first output, and a second output;

a gate for forming synchronized code pulses of said second sub-unit for synchronizing code pulses, having a control input, an input, and an output which is the second output of synchronized code pulses of said unit for synchronizing code and clock pulses, said gate for forming synchronized code pulses of said second sub-unit for synchronizing code pulses being connected through its control input to the first output of said buffer flip-flop of said second sub-unit for synchronizing code pulses, through its second input to the output of said gate for forming synchronizing clock pulses of said clock pulse distribution sub-unit, and through its output to the second input of said flip-flop for storing code pulses of said second sub-unit for synchronizing code pulses and to the first input of said buffer flip-flop of said second sub-unit for synchronizing code pulses;

a coincidence circuit of said second sub-unit for synchronizing code pulses having a first input, a second input, a third input, and an output and being connected through its first input to the second output of said buffer flip-flop of said second sub-unit for synchronizing code pulses, through its second input to the output of said flip-flop for storing code pulses of said second sub-unit for synchronizing code pulses, and through its third input to the output of said gate for forming synchronizing clock pulses of said clock pulse distribution sub-unit, and through its output to the second input of said buffer flip-flop of said second sub-unit for synchronizing code pulses.

46. A digital device, for automatically checking the carbon content in a metal with reference to temperature stops on a cooling curve, comprising:

a converter, which converts the actual temperature of the metal into a numerical pulse code, having an input whereto there is applied a signal carrying information on the temperature of the metal, a first output of code pulses corresponding to a positive increment of temperature of the cooling curve, and a second output of code pulses corresponding to a negative increment of temperature on the cooling curve;

a reversible counter, for converting the numerical pulse code into a parallel code, having an add input, a subtract input, and digit outputs, said reversible counter being electrically connected through its add input and subtract input to the first and second outputs of said converter;

a time interval discriminator having a first input of code pulses corresponding to a positive increment of temperature on the cooling curve, a second input of code pulses corresponding to a negative increment of temperature on the cooling curve, a clock pulse input, and an output, said time interval discriminator being electrically connected through its first and second inputs to the first and second outputs of said converter;

a clock pulse generator having a clock pulse output and being electrically connected through its clock pulse output to the clock pulse input of said time interval discriminator;

a code storage register, for storing codes corresponding to temperature stops on the cooling curve, having information inputs, a control input, and digit outputs, said code storage register being electrically connected through its information inputs to the digit outputs of said reversible counter, and through its control input to the output of said time interval discriminator;

a digital display unit having information inputs and being electrically connected through its information inputs to the digit outputs of said register;

a gate for blocking the passage of clock pulses having a pulse input and an output and being electrically connected through its pulse input to the output of said clock pulse generator, and through its output to the clock pulse input of said time interval discriminator;

a unit for limiting the carbon content checking cycle having a first input and an output whereto there is applied a signal as to the end of the carbon content checking cycle, said unit for limiting the carbon content checking cycle being connected through its first input to the output of said gate for blocking the passage of clock pulses, and through its output to a control input of said gate for blocking the passage of clock pulses; and a counter for counting the duration of the carbon content checking cycle of said unit for limiting the carbon content checking cycle having a first counting input, which is the first input of said unit for limiting the carbon content checking cycle, and a top digit output which is the output of said unit for limiting the carbon content checking cycle, whereto there is applied a signal as to the end of the carbon content checking cycle.

47. A device as claimed in claim 6, wherein said unit for limiting the carbon content checking cycle comprises:

a counter for counting the duration of the carbon content checking cycle having a first counting input, which is the first input of said unit for limiting the carbon content checking cycle, and a top digit output which is the output of said unit for limiting the carbon content checking cycle, whereto there is applied a signal as to the end of the carbon contnet checking cycle.

48. A device as claimed in claim 25, wherein the unit for limiting the carbon content checking cycle comprises:

a counter for counting the duration of the carbon content checking cycle having a first counting input, which is the first input of said unit for limiting the carbon content checking cycle, an initial setting input, which is the initial setting input of said unit for limiting the carbon content checking cycle, and a top digit output which is the output of said unit for limiting the carbon content checking cycle, whereto there is applied a signal as to the end of the carbon content checking cycle.

49. A digital device, for automatically checking the carbon content of a metal with reference to temperature stops on a cooling curve, comprising:

a converter, which converts the temperature of the metal into a numerical pulse code, having an input whereto there is applied a signal carrying information on the temperature of the metal, a first output of code pulses corresponding to a positive increment of temperature on the cooling curve, and a second output of code pulses corresponding to a negative increment of temperature on the cooling curve;

a reversible counter, for converting the numerical pulse code into a parallel code, having an add input, a subtract input, and digit outputs, said reversible counter being electrically connected through its add input and subtract input to the first and second outputs of said converter;

a time interval discriminator having a first input of code pulses corresponding to a positive increment of temperature on the cooling curve, a second input of code pulses corresponding to a negative increment of temperature on the cooling curve, a clock pulse input, and an output, said time interval discriminator being electrically connected through its first and second inputs to the first and second outputs of said converter;

a clock pulse generator having a clock pulse output electrically connected to the clock pulse input of said time interval discriminator;

a code storage register, for storing codes corresponding to temperature stops on the cooling curve, having information inputs, a control input, and outputs, said code storage register being electrically connected through its information inputs to the digit outputs of said reversible counter, and through its control input to the output of said time interval discriminator;

a digital display unit having information inputs and being electrically connected through its information inputs to the digit outputs of said register;

a gate for blocking the passage of clock pulses having a pulse input and an output and being electrically connected through its pulse input to the output of said clock pulse generator, and through its output to the clock pulse input of said time interval discriminator;

a unit for limiting the carbon content checking cycle having a first input and an output whereto there is applied a signal as to the end of the carbon content checking cycle, said unit for limiting the carbon content checking cycle being connected through its first input to the output of said gate for blocking the passage of clock pulses;

a counter for counting the duration of the carbon content checking cycle having a first counting input, which is the first input of said unit for limiting the carbon content checking cycle, and digit outputs;

a switch unit of said unit for limiting the carbon content checking cycle having inputs and outputs; and a coincidence circuit of said unit for limiting the carbon content checking cycle having inputs and an output which is the output of said unit for limiting the carbon content checking cycle, said coincidence circuit being connected through its inputs via the switch unit to the digit outputs of said time counter for counting the duration of the carbon checking cycle.

50. A device as claimed in claim 6, wherein the unit for limiting the carbon content checking cycle comprises:

a time counter for counting the duration of the carbon content checking cycle having a first counting input, which is the first input of said unit for limiting the carbon content checking cycle, and digit outputs;

a switch unit having inputs and outputs; and a coincidence circuit having inputs and an output which is the output of said unit for limiting the carbon content checking cycle, said coincidence circuit being connected through its inputs via the switch unit to the digit outputs of said time counter for counting the duration of the carbon content checking cycle.

51. A device as claimed in claim 25, wherein the unit for limiting the duration of the carbon content checking cycle comprises:

a time counter for counting the duration of the carbon content checking cycle having a first counting input, which is the first input of said unit for limiting the carbon content checking cycle, an initial setting input, which is the initial setting input of said unit for limiting the carbon content checking cycle, and digit outputs;

a switch unit having inputs and outputs; and a coincidence circuit having inputs and an output which is the output of said unit for limiting the carbon content checking cycle, said coincidence circuit being connected through its inputs via the switch unit to the digit outputs of the time counter for counting the duration of the carbon content checking cycle.

52. A digital device, for automatically checking the carbon content in a metal with reference to temperature stops on a cooling curve, comprising:

a converter, which converts the actual temperature of the metal into a numerical pulse code, having an input whereto there is applied a signal carrying information on the temperature of metal, a first output of code pulses corresponding to a positive increment of temperature on the cooling curve, and a second output of code pulses corresponding to a negative increment of temperature on the cooling curve;

a first reversible counter, for converting the numerical pulse code into a parallel code, having an add input, a subtract input, and digit outputs, said first reversible counter being electrically connected through its add input and subtract input to the first and second outputs of said converter;

a discriminator of local temperature increments on the cooling curve having a first input, a second input, a first pulse output, whereto there are applied signals in case of a certain positive increment of temperature on the cooling curve, and a second pulse output, whereto there are applied signals in case of a certain negative increment of temperature on the cooling curve;

a reversible counter, for determining local temperature increments on the cooling curve; of said discriminator of local temperature increments on the cooling curve having an add input, which is the first input of said discriminator of local temperature increments on the cooling curve, whereto there are applied code pulses corresponding to a positive increment of temperature on the cooling curve, a subract input, which is the second input of said discriminator of local temperature increments on the cooling curve, whereto there are applied code pulses corresponding to a negative increment of temperature on the cooling curve, a first overflow output, which is the first pulse output of said discriminator of local temperature increments on the cooling curve, whereto there are applied signals in case of a certain positive increment of temperature on the cooling curve, and a second overflow output, which is the second pulse output of said discriminator of local temperature increments on the cooling curve, whereto there are applied signals in case of a certain negative increment of temperature on the cooling curve;

said discriminator of local temperature increments on the cooling curve being connected through its first and second inputs to the first and second outputs of said converter;

a time interval discriminator having a first input of code pulses corresponding to a positive increment of temperature on the cooling curve, a second input of code pulses corresponding to a negative increment of temperature on the cooling curve, a clock pulse input, and an output;

said time interval discriminator being connected through its first and second inputs to the first and second outputs of said discriminator of local temperature increments on the cooling curve;

a clock pulse generator having a clock pulse output electrically connected to the clock pulse input of said time interval discriminator;

a code storage register, for storing codes corresponding to temperature stops on the cooling curve, having information inputs, a control input, and digit outputs, said code storage register being electrically connected through its information inputs to the digit outputs of said reversible counter, and through its control input to the output of said time interval discriminator; and a digital display unit having information inputs and being electrically connected through its information inputs to the digit outputs of said register.

53. A device as claimed in claim 11, wherein the discriminator of local temperature increments on the cooling curve comprises:

a reversible counter, for determining local temperature increments on the cooling curve, having an add input which is the first input of said discriminator of local temperature increments on the cooling curve, whereto there are applied code pulses corresponding to a positive increment of temperature on the cooling curve, a subtract input which is the second input of said discriminator of local temperature increments on the cooling curve, whereto there are applied code pulses corresponding to a negative increment of temperature on the cooling curve, a first overflow output which is the first pulse output of said discriminator of local temperature increments on the cooling curve, whereto there are applied signals in case of a certain positive increment of temperature on the cooling curve, and a second overflow output which is the second pulse output of said discriminator of local temperature increments on the cooling curve, whereto there are applied signals in case of a certain negative increment of temperature on the cooling curve.

54. A device as claimed in claim 13, wherein the discriminator of local temperature increments on the cooling curve comprises:

a reversible counter, for determining local temperature increments on the cooling curve, having an add input which is the first input of said discriminator of local temperature increments on the cooling curve, whereto there are applied code pulses corresponding to a positive increment of temperature on the cooling curve, a second subtract input which is the input of said discriminator of local temperature increments on the cooling curve, whereto there are applied code pulses corresponding to a negative increment of temperature on the cooling curve, a first overflow output which is the first pulse output of said discriminator of local temperature increments on the cooling curve, whereto there are applied signals in case of a certain positive increment of temperature on the cooling curve, and a second overflow output which is the second pulse output of said discriminator of local temperature increments on the cooling curve, whereto there applied signals in case of a certain negative increment of temperature on the cooling curve.

55. A device as claimed in claim 26, wherein the discriminator of local temperature increments on the cooling curve comprises:

a reversible counter, for determining local temperature increments on the cooling curve, having an add input which is the first input of said discriminator of local temperature increments on the cooling curve, whereto there are applied code pulses corresponding to a positive increment of temperature on the cooling curve, a subtract input which is the second input of said discriminator of local temperature increments on the cooling curve, whereto there are applied code pulses corresponding to a negative increment of temperature on the cooling curve, an initial setting input which is the initial setting input of said discriminator of local temperature increments on the cooling curve, a first overflow output which is the first pulse output of said discriminator of local temperature increments on the cooling curve, whereto there are applied signals in case of a certain positive increment of temperature on the cooling curve, and a second overflow output which is the second pulse output of said discriminator of local temperature increments on the cooling curve, whereto there are applied signals in case of a certain negative increment of temperature on the cooling curve.

56. A ditigal device, for automatically checking the carbon content in metal with reference to temperature stops on a cooling curve, comprising:

a converter, which converts the actual temperature of the metal into a numerical pulse code, having an input whereto there is applied a signal carrying information on the temperature of metal, a first output of code pulses corresponding to a positive increment of temperature on the cooling curve, and a second output of code pulses corresponding to a negative increment of temperature on the cooling curve;

a first reversible counter, for converting the numerical pulse code into a parallel code, having an add input, a subtract input, and digit outputs, said first reversible counter being electrically connected through its add input and subtract input to the first and second outputs of said converter;

a discriminator of local temperature increments on the cooling curve having a first input, a second input, a first pulse output whereto there are applied signals in case of a certain positive increment of temperature on the cooling curve, and a second pulse output whereto there are applied signals in case of a certain negative increment of temperature on the cooling curve;

a first gate for blocking the count of code pulses, corresponding to a positive increment of temperature on the cooling curve, of said discriminator of local temperature increments on the cooling curve having a pulse input which is the first input of said discriminator of local temperature increments on the cooling curve, whereto there are applied code pulses corresponding to a positive increment of temperature on the cooling curve, a control input, and an output;

a second gate for blocking the count of code pulses, corresponding to a negative increment of temperature on the cooling curve, of said discriminator of local temperature increments on the cooling curve having a pulse input which is the second input of said discriminator of local temperature increments on the cooling curve, whereto there are applied code pulses corresponding to a negative increment of temperature on the cooling curve, a control input, and an output;

a reversible counter, for determining local temperature increments on the cooling curve with a sign digit, of said discriminator of local temperature increments on the cooling curve having an add input, a subtract input, a first initial setting input, a second initial setting input, a first sign digit output, a second sign digit output, and digit outputs, said reversible counter of said discriminator of local temperature increments on the cooling curve being connected through its add input to the output of said first gate for blocking the count of code pulses, and through its subtract input to the output of said second gate for blocking the count of code pulses;

a first switch unit of said discriminator of local temperature increments on the cooling curve having inputs and outputs;

a first coincidence circuit of said discriminator of local temperature increments on the cooling curve having inputs and an output whereat there are formed signals in case of a certain positive increment of temperature on the cooling curve, said first coincidence circuit being connected through its inputs to the first sign digit output and via said first switch unit to the digit outputs of said reversible counter of said discriminator of local temperature increments on the cooling curve, and through its output to the control input of said first gate for blocking code pulses;

a first output gate of said discriminator of local temperature increments on the cooling curve having a control input, a pulse input, and an output whereto there are applied signals in case of a certain positive increment of temperature on the cooling curve, said output being the first output of said discriminator of local temperature increments on the cooling curve, said first output gate of said discriminator of local temperature increments on the cooling curve being connected through its control input to the output of said first coincidence circuit, through its pulse input to the pulse input of said first gate for blocking code pulses, and through its putput to the first initial setting input of said reversible counter of said discriminator of local temperature increments on the cooling curve;

a second switch unit of said discriminator of local temperature increments on the cooling curve having inputs and outputs;

a second coincidence circuit of said discriminator of local temperature increments on the cooling curve having inputs and an output whereat there are formed signals in case of a certain negative increment of temperature on the cooling curve, said second coincidence circuit being connected through its inputs to the second sign digit output and via said second switch unit to the digit outputs of said reversible counter of said discriminator of local temperature increments on the cooling curve, and through its output to the control input of said second gate for blocking code pulses;

a second output gate of said discriminator of local temperature increments on the cooling curve having a control input, a pulse input, and an output whereto there are applied signals in case of a certain negative increment of temperature on the cooling curve, said output being the second output of said discriminator of local temperature increments on the cooling curve, said second output gate of said discriminator of local temperature increments on the cooling curve being connected through its control input to the output of said second coincidence circuit, through its pulse input to the pulse input of said second gate for blocking code pulses, and through its output to the second initial setting input of said reversible counter of said discriminator of local temperature increments on the cooling curve;

said discriminator of local temperature increments on the cooling curve being connected through its first and second inputs to the first and second outputs of said converter;

a time interval discriminator having a first input of code pulses corresponding to a positive increment of temperature on the cooling curve, a second input of code pulses corresponding to a negative increment of temperature on the cooling curve, a clock pulse input, and an output, said time interval discriminator being connected through its first and second inputs to the first and second outputs of said discriminator of local temperature increments on the cooling curve;

a clock pulse generator having a clock pulse output electrically connected to the clock pulse input of said time interval discriminator;

a code storage register, for storing code corresponding to temperature stops on the cooling curve, having information inputs, a control input, and digit outputs, said code storage register being electrically connected through its information inputs to the digit outputs of said reversible counter, and through its control input to the output of said time interval discriminator; and a digital display unit having information inputs and being electrically connected through its information inputs to the digit outputs of said register.

57. A device as claimed in claim 11, wherein said discriminator of local temperature increments on the cooling curve comprises:
- a first gate for blocking the count of code pulses, corresponding to a positive increment of temperature on the cooling curve, having a pulse input which is the first input of said discriminator of local temperature increments on the cooling curve, whereto there is applied a code pulse corresponding to a positive increment of temperature on the cooling curve, a control input, and an output;
- a second gate for blocking the count of code pulses, corresponding to a negative increment of temperature on the cooling curve, having a pulse input which is the second input of said discriminator of local temperature increments on the cooling curve, whereto there are applied code pulses corresponding to a negative increment of temperature on the cooling curve, a control input, and an output;
- a reversible counter, for determining local temperature increments on the cooling curve, of said discriminator of local temperature increments on the cooling curve having a sign digit, an add input, a subtract input, a first initial setting input, a second initial setting input, a first sign digit output, a second sign digit output, and digit outputs, said reversible counter of said discriminator of local temperature increments on the cooling curve being connected through its add input to the output of said first gate for blocking the count of code pulses, and through its subtract input to the output of said second gate for blocking the count of code pulses;
- a first switch unit having a inputs and outputs;
- a first coincidence circuit having inputs and an output whereat there are formed signals in case of a certain positive increment of temperature on the cooling curve, said first coincidence circuit being connected through its inputs to the first sign digit output and via said first switch unit to the digit outputs of said reversible counter of said discriminator of local increments of temperature on the cooling curve, and through its output to the control input of said first gate for blocking the count of code pulses;
- a first output gate having a first input, a pulse input, and an output whereto there are applied signals in case of a certain positive increment of temperature on the cooling curve, said output being the first output of said discriminator of local temperature increments on the cooling curve, said first output gate being connected through its control input to the output of said first coincidence circuit, through its pulse input to the pulse input of said first gate for blocking the count of code pulses, and through its output to the first initial setting input of said reversible counter of said discriminator of local temperature increments on the cooling curve;
- a second switch unit having inputs and outputs;
- a second coincidence circuit having inputs and an output whereat there are formed signals in the case of a certain negative increment of temperature on the cooling curve, said second coincidence circuit being connected through its inputs to the second sign digit output and via said second switch unit to the digit outputs of said reversible counter of said discriminator of local temperature increments on the cooling curve, and through its output to the control input of said second gate for blocking the count of code pulses;
- a second output gate having a control input, a pulse input, and an output whereto there are applied signals in case of a certain negative increment of temperature on the cooling curve, said output being the second output of said discriminator of local temperature increments on the cooling curve; said second output gate being connected through its control input to the output of said second coincidence circuit, through its pulse input to the pulse input of said second gate for blocking the count of code pulses, and through its output to the second initial setting input of said reversible counter of said discriminator of local temperature increments on the cooling curve.

58. A device as claimed in claim 13, wherein the discriminator of local temperature increments on the cooling curve comprises:
- a first gate for blocking the count of code pulses, corresponding to a positive increment of temperature on the cooling curve, having a pulse input which is the first input of said discriminator of local temperature increments on the cooling curve, whereto there are applied code pulses corresponding to a positive increment of temperature on the cooling curve, a control input, and an output;
- a second gate for blocking the count of code pulses, corresponding to a negative increment of temperature on the cooling curve, having a pulse input which is the second input of said discriminator of local temperature increments on the cooling curve, whereto there are applied code pulses corresponding to a negative increment of temperature on the cooling curve, a control input, and an output;
- a reversible counter, for determining local temperature increments on the cooling curve, of said discriminator of local temperature increments on the cooling curve having a sign digit, an add input, a subtract input, a first initial setting input, a second initial setting input, a first signal digit output, a second sign digit output, and digit outputs, said reversible counter of said discriminator of local temperature increments on the cooling curve being connected through its add input to the output of said first gate for blocking the count of code pulses, and through its subtract input to the output of said second gate for blocking the count of code pulses;
- a first switch unit having inputs and outputs;
- a first coincidence circuit having inputs and an output whereat there are formed signals in case of a certain positive increment of temperature on the cooling curve, said first coincidence circuit being connected through its inputs to the first sign digit output and via said first switch unit to the digit outputs of said reversible counter of said discriminator of local temperature increments on the cooling curve, and through its output to the control input of said first gate for blocking the count of code pulses;
- a first output gate having a control input, a pulse input, and an output whereto there are applied signals in case of a certain positive increment of temperature on the cooling curve, said output being the output of said discriminator of local temperature increments on the cooling curve, said first output gate being connected through its control input to the output of said first coincidence circuit, through its pulse input to the pulse input of said first gate for blocking the count to code pulses, and through its output to the first initial setting input of said reversible counter of said discriminator of local temperature increments on the cooling curve;

a second switch unit having inputs and outputs;

a second coincidence circuit having inputs and an output whereat there are formed signals in case of a certain negative increment of temperature on the cooling curve, said second coincidence circuit being connected through its inputs to the second sign digit output and via said second switch unit to the digit outputs of said reversible counter of said discriminator of local temperature increments on the cooling curve, and through its output to the control input of said second gate for blocking the count of code pulses;

a second output gate having a control input, a pulse input, and an output whereto there are applied signals in case of a certain negative increment of temperature on the cooling curve, said output being the second output of said discriminator of local temperature increments on the cooling curve, said second output gate being connected through its control input to the output of said second coincidence circuit, through its pulse input to the pulse input of said second gate for blocking the count of code pulses, and through its output to the second initial setting input of said reversible counter of said discriminator of local temperature increments on the cooling curve.

59. A device as claimed in claim 26, wherein the discriminator of local temperature increments on the cooling curve comprises:

a first gate for blocking the count of code pulses, corresponding to a positive increment of temperature on the cooling curve, having a pulse input which is the first input of said discriminator of local temperature increments on the cooling curve, whereto there are applied code pulses corresponding to a positive increment of temperature on the cooling curve, a control input, and an output;

a second gate for blocking the count of code pulses, corresponding to a negative increment of temperature on the cooling curve, having a pulse input which is the second input of said discriminator of local temperature increments on the cooling curve, whereto there are applied code pulses corresponding to a negative increment of temperature on the cooling curve, a control input, and an output;

a reversible counter, for determining local temperature increments on the cooling curve, of said discriminator of local temperature increments on the cooling curve having a sign digit, an add input, a subtract input, a first initial setting input, a second initial setting input, a third initial setting input which is the initial setting input of said discriminator of local temperature increments on the cooling curve, a first sign digit output, a second sign digit output, and digit output, said reversible counter of said discriminator of local temperature increments on the cooling curve being connected through its add input to the output of said first gate for blocking the count of code pulses, and through its subtract input to the output of said second gate or blocking the count of code pulses;

a first switch unit having inputs and outputs;

a first coincidence circuit having inputs and an output whereat there are formed signals in case of a certain positive increment of temperature on the cooling curve, said first coincidence circuit being connected through its inputs to the first sign digit output and via said first switch unit to the digit output of said reversible counter of said discriminator of local temperature increments on the cooling curve, and through its output to the control input of said first gate for blocking the count of code pulses;

a first output gate having a control input, a pulse input, and an output whereto there are applied signals in case of a certain positive increment of temperature on the cooling curve, said output being the first output of said first discriminator of local temperature increments on the cooling curve, said first output gate being connected through its control input to the output of said first coincidence circuit, through its pulse input to the pulse input of said first gate for blocking the count of code pulses, and through its output to the first initial setting input of said reversible counter of said discriminator of local temperature increments on the cooling curve;

a second switch unit having inputs and outputs;

a second coincidence circuit having inputs and an output whereat there are formed signals in case of a certain negative increment of temperature on the cooling curve, said second coincidence circuit being connected through its inputs via said second switch unit to the second sign digit output and via said second switch unit to the digit outputs of said reversible counter of said discriminator of local temperature increments on the cooling curve, and through its output to the control input of said second gate for blocking the count of code pulses;

a second output gate having a control input, a pulse input, and an output whereto there are applied signals in case of a certain negative increment of temperature on the cooling curve, said output being the second output of said discriminator of local temperature increments on the cooling curve, said second output gate being connected through its control input to the output of said second coincidence circuit through its pulse input to the pulse input of said second gate for blocking the count of code pulses, and through its output to the second initial setting input of said reversible counter of said discriminator of local temperature increments on the cooling curve.

60. A digital device, for automatically checking the carbon content in a metal with reference to temperature increments on a cooling curve, comprising:

a converter, which converts the actual temperature of the metal into a numerical pulse code, having an input whereto there is applied a signal carrying information on the temperature of metal, a first output of code pulses corresponding to a positive increment of temperature on the cooling curve, and a second output of code pulses corresponding to a negative increment of temperature on the cooling curve;

a first reversible counter, for converting the numerical pulse code into a parallel code, having an add input, a subtract input, and digit outputs, said first reversible counter being electrically connected through its add input and subtract input to the first and second pulse outputs of said converter;

a discriminator of local temperature increments on the cooling curve having a first input, a second input, a first pulse output whereto there are applied signals in case of a certain positive increment of temperature on the cooling curve, and a second pulse output whereto there are applied signals in case of a certain negative increment of temperature on the cooling curve;

a first threshold unit of said discriminator of local temperature increments on the cooling curve;

a first gate for blocking the count of code pulses, corresponding to a positive increment of temperature on the cooling curve, of said first threshold unit having a pulse input whereto there are applied code pulses corresponding to a positive increment of temperature on the cooling curve, which input is the first input of said discriminator of local temperature increments on the cooling curve, a control input, and an output;

a second gate for blocking the count of code pulses corresponding to a negative increment of temperature on the cooling curve, of said first threshold unit having a pulse input, a control input, and an output;

a reversible counter, for determining local temperature increments on the cooling curve, of said first threshold unit having an add input, a subtract input, a first initial setting input, and digit outputs, said reversible counter of said first threshold unit being connected through its add input to the output of said first gate for blocking the count of code pulses of said first threshold unit, and through its subtract input to the output of said second gate for blocking the count of code pulses of said first threshold unit;

a switch unit of said first threshold unit having inputs and outputs;

a coincidence circuit of said first threshold unit having inputs and an output whereat there are formed signals in case of a certain positive increment of temperature on the cooling curve, said coincidence circuit of said first threshold unit being connected through its inputs via said switch unit of said first threshold unit to the digit outputs of said reversible counter for determining local temperature increments on the cooling curve of said first threshold unit, and through its output to the control input of said first gate for blocking the count of code pulses of said first threshold unit;

a zero decoder of said first threshold unit having inputs and an output, said zero decoder of said first threshold unit being connected through its inputs to the digit outputs of said reversible counter for determining local temperature increments on the cooling curve of said first threshold unit, and through its output to the control input of said second gate for blocking the count of code pulses of said first threshold unit;

an output gate of said first threshold unit having a pulse input, a control input, and an output which is the pulse output of said discriminator of local temperature increments on the cooling curve, whereto there is applied a signal in case of a certain positive increment of temperature on the cooling curve, said output gate of said first threshold unit being connected through its pulse input to the pulse input of said first gate for blocking the count of code pulses of said first threshold unit, through its control input to the output of said coincidence circuit of said first threshold unit, and through its output to the initial setting input of said reversible counter for determining local temperature increments on the cooling curve of said first threshold unit;

a second threshold unit of said discriminator of local temperature increment on the cooling curve;

a first gate for blocking the count of code pulses, corresponding to a positive increment of temperature on the cooling curve, of said second threshold unit having a pulse input, a control input, and an output, said first gate of said second threshold unit being connected through its pulse input to the pulse input of said first gate for blocking the count of code pulses of said first threshold unit;

a second gate for blocking the count of code pulses, corresponding to a negative increment of temperature on the cooling curve, of said second threshold unit having a pulse input whereto there are applied code pulses corresponding to a negative increment of temperature on the cooling curve, which input is the second input of said discriminator of local temperature increments on the cooling curve, a control input, and an output, said second gate of said second threshold unit being connected through its pulse input to the pulse input of said second gate for blocking the count of code pulses of said first threshold unit;

a reversible counter, for determining local temperature increments on the cooling curve, of said second threshold unit having an add input, a subtract input, an initial setting input, and digit outputs, said reversible counter of said second threshold unit being connected through its add input to the output of said first gate for blocking the count of code pulses of said second threshold unit, and through its subtract input to the output of said second gate for blocking the count of code pulses of said second threshold unit;

a switch unit of said second threshold unit having inputs and outputs;

a coincidence circuit of said second threshold unit having inputs and an output whereat there are formed signals in case of a certain negative increment of temperature on the cooling curve, said coincidence circuit of said second threshold unit being connected through its inputs via said switch unit of said second threshold unit to the digit outputs of said reversible counter for determining local temperature increments on the cooling curve of said second threshold unit, and through its output to the control input of said second gate for blocking the count of code pulses of said second threshold unit;

a zero decoder of said second threshold unit having inputs and an output, said zero decoder of said second threshold unit being connected through its input to the digit outputs of said reversible counter for determining local temperature increments on the cooling curve of said second threshold unit, and through its output to the control input of said first gate for blocking the count of code pulses of said second threshold unit;

an output gate of said second threshold unit having a pulse input, a control input, and an output which is the pulse output of said discriminator of local temperature increments on the cooling curve, whereto there is applied a signal in case of a certain negative increment of temperature on the cooling curve, said output gate of said second threshold unit being connected through its pulse input to the pulse input of said second gate for blocking the count of code pulses of said second threshold unit, through its control input to the output of said coincidence circuit of said second threshold unit, and through its output to the initial setting input of said reversible counter for determining local temperature increments on the cooling curve of said second threshold unit;

said discriminator of local temperature increments on the cooling curve being connected through its first and second inputs to the first and second outputs of said converter;

a time interval discriminator having a first input of code pulses corresponding to a positive increment of temperature on the cooling curve, a second input of code pulses corresponding to a negative increment of temperature on the cooling curve, a clock pulse input, and an output, said time interval discriminator being connected through its first and second inputs to the first and second outputs of said discriminator of local temperature increments on the cooling curve;

a clock pulse generator having a clock pulse output and being electrically connected through its clock pulse output to the clock pulse input of said time interval discriminator;

a code storage register, for storing codes corresponding to temperature stops in the cooling curve, having information inputs, a control input, and digit outputs, said code storage register being electrically connected through its information inputs to the digit outputs of said reversible counter, and through its control input to the output of said time interval discriminator; and a digital display unit having information inputs and being electrically connected through its information inputs to the digit outputs of said register.

61. A device as claimed in claim 11, wherein the discriminator of local temperature increments on the cooling curve comprises:

a first threshold unit;

a first gate for blocking the count of code pulses, corresponding to a positive increment of temperature on the cooling curve, of said first threshold unit having a pulse input whereto there are applied code pulses corresponding to a positive increment of temperature on the cooling curve, which input is the first input of said discriminator of local temperature increments on the cooling curve, a control input, and an output;

a second gate for blocking the count of code pulses, corresponding to a negative increment of temperature on the cooling curve, of said first threshold unit pulse having a input, a control input, and an output;

a reversible counter, for determining local temperature increments on the cooling curve, of said first threshold unit having an add input, a subtract input, an initial setting input, and digit outputs, said reversible counter of said first threshold unit being connected through its add input to the output of said first gate for blocking the count of code pulses of said first threshold unit, and through its subtract input to the output of said second gate for blocking the count of code pulses of said first threshold unit;

a switch unit of said first threshold unit having inputs and outputs;

a coincidence circuit of said first threshold unit having inputs and an output whereat there are formed signals in case of a certain positive increment of temperature on the cooling curve, said coincidence circuit of said first threshold unit being connected through its inputs via said switch unit of said first threshold unit to the digit outputs of said reversible counter for determining local temperature increments on the cooling curve of said first threshold unit, and through its output to the control input of said first gate for blocking the count of code pulses of said first threshold unit;

a zero decoder of said first threshold unit having inputs and an output, said zero decoder of said first threshold unit being connected through its inputs to the digit outputs of said reversible counter for determining local temperature increments on the cooling curve of said first threshold unit, and through its output to the control input of said second gate for blocking the count of code pulses of said first threshold unit;

an output gate of said first threshold unit having a pulse input, a control input, and an output which is the output of said discriminator of local temperature increments on the cooling curve whereto there is applied a signal in case of a certain positive increment of temperature on the cooling curve, said output gate of said first threshold unit being connected through its pulse input to the pulse input of said first gate for blocking the count of code pulses of said first threshold unit, through its control unit to the output of said coincidence circuit of said first threshold unit, and through its output to the initial setting input of said reversible counter for determining local temperature increments on the cooling curve of said first threshold unit;

a second threshold unit;

a first gate for blocking the count of code pulses, corresponding to a positive increment of temperature on the cooling curve, of said second threshold unit having a pulse input, a control input, and an output, said first gate for blocking the count of code pulses of said second threshold unit being connected through its pulse input to the pulse input of said first gate for blocking the count of code pulses of said first threshold unit;

a second gate for blocking the count of code pulses, corresponding to a negative increment of temperature on the cooling curve, of said second threshold unit having a pulse input whereto there are applied code pulses corresponding to a negative increment of temperature on the cooling curve, which input is the second input of said discriminator of local temperature increments on the cooling curve, a control input, and an output, said second gate for blocking the count of code pulses of said second threshold unit being connected through its pulse input to the pulse input of said second gate for blocking the count of code pulses of said first threshold unit;

a reversible counter, for determining local temperature increments on the cooling curve, of said second threshold unit having an add input, a subtract input, an initial setting input, and digit outputs, said reversible counter of said second threshold unit being connected through its add input to the output of said first gate for blocking the count of code pulses of said second threshold unit, and through its subtract input to the output of said second gate for blocking the count of code pulses of said second threshold unit;

a switch unit of said second threshold unit having inputs and outputs;

a coincidence circuit of said second threshold unit having inputs and an output whereat there are formed signals in case of a certain negative increment of temperature on the cooling curve, said coincidence circuit of said second threshold unit being connected through its inputs via said switch unit of said second threshold unit to the digit outputs of said reversible counter for determining local temperature increments on the cooling curve of said second threshold unit, and through its output to the control input of said second gate for blocking the count of code pulses of said second theshold unit;

a zero decoder of said second threshold unit having inputs and an output, said zero decoder of said second threshold unit being connected through its inputs to the digit outputs of said reversible counter for determining local temperature increments on the cooling curve of said second threshold unit, and through its output to the control input of said first gate for blocking the count of code pulses of said second threshold unit;

an output gate of said second threshold unit having a pulse input, a control input, and an output which is the pulse output of said discriminator of local temperature increments on the cooling curve, whereto there is applied a signal in case of a certain negative increment of temperature on the cooling curve, said output gate of said second threshold unit being connected through its pulse input to the pulse input of said second gate for blocking the count of code pulses of said second threshold unit, through its control input to the output of said coincidence circuit of said second threshold unit, and through its output to the initial setting input of said reversible counter for determining local temperature increments on the cooling curve of said second threshold unit.

62. A device as claimed in claim 13, wherein the discriminator of local temperature increments on the cooling curve comprises:

a first threshold unit;

a first gate for blocking the count of code pulses, corresponding to a positive increment of temperature on the cooling curve, of said first threshold unit having a pulse input where there are applied code pulses corresponding to a positive increment of temperature on the cooling curve, which input is the first input of said discriminator of local temperature increments on the cooling curve, a control input, and an output;

a second gate for blocking the count of code pulses, corresponding to a negative increment of temperature on the cooling curve, of said first threshold unit having a pulse input, a control input, and an output;

a reversible counter, for determining local temperature increments on the cooling curve, of said first threshold unit having an add input, a subtract input, an initial setting input, and digit outputs, said reversible counter of said first threshold unit being connected through its add input to the output of said first gate for blocking the count of code pulses of said first threshold unit, and through its subteact input to the output of said second gate for blocking the count of code pulses of said first threshold unit;

a switch unit of said first threshold unit having inputs and outputs;

a coincidence circuit of said first threshold unit having inputs and an output whereat there are formed signals in case of a certain positive increment of temperature on the cooling curve, said coincidence circuit of said first threshold unit being connected through its inputs via said switch unit of said first threshold unit to the digit outputs of said reversible counter for determining local temperature increments on the cooling curve of said first threshold unit, and through its output to the control input of said first gate for blocking the count of code pulses of said first threshold unit;

a zero decoder of said first threshold unit having inputs and output, said zero decoder of said first threshold unit being connected through its inputs to the digit outputs of said reversible counter for determining local temperature increments on the cooling curve of said first threshold unit, and through its output to the control input of said second gate for blocking the count of code pulses of said first threshold unit;

an output gate of said first threshold unit, said output gate of said first threshold unit being connected through a pulse input to the pulse input of said first gate for blocking the count of code pulses of said first threshold unit, through a control input to the output of said coincidence circuit of said first threshold unit, and through an output to the initial setting input of said reversible counter for determining local temperature increments on the cooling curve of said first threshold unit;

a second threshold unit;

a first gate for blocking the count of code pulses, corresponding to a positive increment of temperature on the cooling curve, of said second threshold unit having a pulse input, a control input, and an output, said first gate for blocking the count of code pulses of said second threshold unit being connected through its pulse input to the pulse input of said first gate for blocking the count of code pulses of said first threshold unit;

a second gate for blocking the count of code pulses, corresponding to a negative increment of temperature on the cooling curve, of said second threshold unit having a pulse input whereto there are applied code pulses corresponding to a negative increment of·temperature on the cooling curve, which input is the second input of said discriminator of local temperature increments on the cooling curve, a control input, and an output, said second gate for blocking the count of code pulses of said second threshold unit being connected through its pulse input to the pulse input of said second gate for blocking the count of code pulses of said first threshold unit;

a reversible counter, for determining local temperature increments on the cooling curve, of said second threshold unit having an add input, a subtract input, an initial setting input, and digit outputs, said reversible counter of said second threshold unit being connected through its add input to the output of said first gate for blocking the count of code pulses of said second threshold unit, and through its subtract input to the output of said second gate for blocking the count of code pulses of said second threshold unit;

a switch unit of said second threshold unit having inputs and outputs;

a coincidence circuit of said second threshold unit having inputs and an output whereat there are formed signal in case of a certain negative increment of temperature on the cooling curve, which output is the information output of said discriminator of local temperature increments on the cooling curve, said coincidence circuit of said second threshold unit being connected through its inputs via said switch units of said second threshold unit to the digit outputs of said reversible counter for determining local temperature increments on the cooling curve of said second threshold unit, and through its output to the control input of said second gate for blocking the count of code pulses of said second threshold unit;

a zero decoder of said second threshold unit having inputs and an output and being connected through its inputs to the digit outputs of said reversible counter for determining local temperature increments on the cooling curve of said second threshold unit, and through its output to the input of said first gate for blocking the count of code pulses of said second threshold unit;

an output gate of said second threshold unit having a pulse input, a control input, and an output which is the pulse output of said discriminator of local temperature increments on the cooling curve, whereto there is applied a signal in case of a certain negative increment of temperature on the cooling curve, said output gate of said second threshold unit being connected through its pulse input to the pulse input of said second gate for blocking the count of code pulses of said second threshold unit, through its control input to the output of said coincidence circuit of said second threshold unit, and through its output to the initial setting input of said reversible counter for determining local temperature increments on the cooling curve of said second threshold unit.

63. A device as claimed in claim 26, wherein the discriminator of local temperature increments on the cooling curve comprises:

a first threshold unit;

a first gate for blocking the count of code pulses, corresponding to a positive increment of temperature on the cooling curve, of said first threshold unit having a pulse input whereto there are applied code pulses corresponding to a positive increment of temperature on the cooling curve, which input is the first input of said discriminator of local temperature increments on the cooling curve, a control input, and an output;

a second gate for blocking the count of code pulses, corresponding to a negative increment of temperature on the cooling curve, of said first threshold unit, having a pulse input, a control input, and an output;

a reversible counter, for determining local temperature increments on the cooling curve, of said first threshold unit having an add input, a subtract input, a first initial setting input, a second initial setting input, and digit outputs, said reversible counter of said first threshold unit being connected through its add input to the output of said first gate for blocking the count of code pulses of said first theshold unit, and through its subtract unit to the output of said second gate for blocking the count of code pulses of said first threshold unit;

a switch unit of said first threshold unit having inputs and outputs;

a coincidence circuit of said first threshold unit having inputs and an output whereat there are formed signals in case of a certain positive increment of temperature on the cooling curve, said coincidence circuit of said first threshold unit being connected through its inputs via said switch unit of said first threshold unit to the digit outputs of said reversible counter for determining local temperature increments on the cooling curve of said first theshold unit, and through its output to the control input of said first gate for blocking the count of code pulses of said first threshold unit;

a zero decoder of said first threshold unit having inputs and an output and being connected through its inputs to the digit outputs of said reversible counter for determining local temperature increments on the cooling curve of said first threshold unit, and through its output to the control input of said second gate for blocking the count of code pulses of said first threshold unit;

an output gate of said first threshold unit connected through a pulse input to the pulse input of said first gate for blocking the count of code pulses of said first threshold unit, through a control input to the output of said coincidence circuit of said first threshold unit, and through its output to the first initial setting input of said reversible counter for determining local temperature increments on the cooling curve of said first threshold unit;

a second threshold unit;

a first gate for blocking the count of code pulses, corresponding to a positive increment of temperature on the cooling curve, of said second threshold unit having a pulse input, a control input, and an output, said first gate for blocking the count of code pulses of said second threshold unit being connected through its pulse input to the pulse input of said first gate for blocking the count of code pulses of said first threshold unit;

a second gate for blocking the count of code pulses, corresponding to a negative increment of temperature on the cooling curve, of said second threshold unit having a pulse input whereto there are applied code pulses corresponding to a negative increment of temperature on the cooling curve, which input is the second input of said discriminator of local temperature increments on the cooling curve, a control input, and an output, said second gate for blocking the count of code pulses of said second threshold unit being connected through its pulse input to the pulse input of said second gate for blocking the count of code pulses of said first threshold unit;

a reversible counter, for determining local temperature increment on the cooling curve, of said second threshold unit having an add input, a subtract input, a first initial setting input, a second initial setting input which is the initial setting input of said discriminator of local temperature increments on the cooling curve, and digit outputs, said reversible counter of said second theshold unit being connected through its add input to the output of said first gate for blocking the count of code pulses of said second threshold unit, through its subtract input to the output of said second gate for blocking the count of code pulses of said second threshold unit, and through its second initial setting input to the second initial setting input of said reversible counter for determining local temperature increments on the cooling curve of said first threshold unit;

a switch unit of said second threshold unit having inputs and outputs;

a coincidence circuit of said second threshold unit having inputs and an output whereat there are formed signals in case of a certain negative increment of temperature on the cooling curve, said coincidence circuit of said second threshold unit being connected through its inputs via said switch unit of said second threshold unit to the digit outputs of said reversible counter for determining local temperature increments on the cooling curve of said second threshold unit, and through its output to the control input of said second gate for blocking the count of code pulses of said second threshold unit;

a zero decoder of said second threshold unit having inputs and an output and being connected through its inputs to the digit outputs of said reversible counter for determining local temperature increments on the cooling curve of said second threshold unit, and through its output to the control input of said first gate for blocking the count of code pulses of said second threshold unit;

an output gate of said second threshold unit having a pulse input, a control input, and an output which is the pulse output of said discriminator of local temperature increments on the cooling curve, whereto there is applied a signal in case of a certain negative increment of temperature on the cooling curve, said output gate of said second threshold unit being connected through its pulse input to the pulse input of said second gate for blocking the count of code pulses of said second threshold unit, through its control input to the output of said coincidence circuit of said second threshold unit, and through its output to the first initial setting input of said reversible counter for determining local temperature increments on the cooling curve of said second threshold unit.

* * * * *

UNITED STATES PATENT OFFICE
CERTIFICATE OF CORRECTION

PATENT NO. : 4,088,974
DATED : May 9, 1978
INVENTOR(S) : Leonid Sergeevich Zhitetsky, et al It is certified that error appears in the above–identified patent and that said Letters Patent are hereby corrected as shown below:

On the front page, left-hand column, line [30], change "210027" to --2100227--.

Signed and Sealed this

Fourteenth Day of November 1978

[SEAL]

Attest:

RUTH C. MASON
Attesting Officer

DONALD W. BANNER
Commissioner of Patents and Trademarks